(12) United States Patent
Chin et al.

(10) Patent No.: US 10,016,341 B2
(45) Date of Patent: Jul. 10, 2018

(54) SYSTEMS AND DEVICES FOR CONTROLLING DELIVERY OF BREAST MILK SUPPLEMENTATION

(71) Applicant: Elwha LLC, Bellevue, WA (US)

(72) Inventors: Hon Wah Chin, Palo Alto, CA (US); Roderick A. Hyde, Redmond, WA (US); Elizabeth A. Sweeney, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 345 days.

(21) Appl. No.: 14/673,456

(22) Filed: Mar. 30, 2015

(65) Prior Publication Data

US 2016/0287481 A1 Oct. 6, 2016

(51) Int. Cl.
*A61J 9/00* (2006.01)
*A61J 7/00* (2006.01)
(Continued)

(52) U.S. Cl.
CPC .............. *A61J 9/00* (2013.01); *A61J 7/0015* (2013.01); *A61J 7/0076* (2013.01); *A61J 13/00* (2013.01); *A61J 17/006* (2015.05); *G06F 19/3456* (2013.01); *G16H 40/63* (2018.01); *A61B 10/0051* (2013.01); *A61J 11/0005* (2013.01);
(Continued)

(58) Field of Classification Search
CPC ........ A61M 1/06–1/068; A61M 1/007; A61M 2210/1007; A61J 13/00; A61J 9/00; A61J 17/006; A61J 17/001; A61J 7/0015; A61J 7/0076; A61J 11/0005; A61J 15/0011; A61J 2200/70; G06F 19/3406
See application file for complete search history.

(56) References Cited

U.S. PATENT DOCUMENTS 4,384,288 A  5/1983  Walton
4,687,466 A  8/1987  Larsson
(Continued)

OTHER PUBLICATIONS

"8mm Diaphragm Isolation"; ASCO; accessed on Feb. 24, 2015, pp. 1-2.
(Continued)

*Primary Examiner* — Bradley J Osinski
*Assistant Examiner* — Nilay Shah

(57) ABSTRACT

Systems and devices for controlling delivery of a breast milk supplement are described which include a nipple component including aperture; a guard component attached to the nipple component; a supplement reservoir including a port with a controllable valve, the supplement reservoir adapted to contain one or more breast milk supplements, a flow conduit disposed within at least a portion of the nipple component and having a first end in fluid communication with the aperture and a second end in fluid communication with the port; a data storage component including a breast milk supplement regimen; and a control unit operably coupled to the controllable valve and the data storage component and including a microprocessor and circuitry, the circuitry including actuation circuitry configured to actuate the controllable valve to module release of the one or more breast milk supplements based on the breast milk supplement regimen.

35 Claims, 33 Drawing Sheets

(51) Int. Cl.

| | | |
|---|---|---|
| A61J 13/00 | (2006.01) | |
| A61J 17/00 | (2006.01) | |
| G06F 19/00 | (2018.01) | |
| G16H 40/63 | (2018.01) | |
| A61B 10/00 | (2006.01) | |
| A61J 11/00 | (2006.01) | |
| A61J 15/00 | (2006.01) | |

(52) U.S. Cl.
CPC ........ *A61J 15/0011* (2013.01); *A61J 2200/30* (2013.01); *A61J 2200/42* (2013.01); *A61J 2200/70* (2013.01); *A61J 2200/74* (2013.01); *A61J 2205/60* (2013.01); *A61M 2210/1007* (2013.01); *Y02A 90/26* (2018.01)

(56) References Cited

U.S. PATENT DOCUMENTS

| | | | |
|---|---|---|---|
| 4,951,032 | A | 8/1990 | Langsam |
| 5,361,070 | A | 11/1994 | McEwan |
| 5,475,096 | A | 12/1995 | Gold et al. |
| 5,573,012 | A | 11/1996 | McEwan |
| 5,774,091 | A | 6/1998 | McEwan |
| 5,932,262 | A | 8/1999 | Little |
| 6,033,367 | A * | 3/2000 | Goldfield ............... A61B 5/087 215/11.1 |
| 6,248,378 | B1 * | 6/2001 | Ganan-Calvo ....... A61K 9/1694 424/439 |
| 6,693,513 | B2 | 2/2004 | Tuttle |
| 7,101,565 | B2 | 9/2006 | Monte |
| 7,411,505 | B2 | 8/2008 | Smith et al. |
| 7,479,886 | B2 | 1/2009 | Burr |
| 7,569,051 | B2 | 8/2009 | Shachar |
| 7,632,406 | B2 | 12/2009 | Wilson et al. |
| 7,731,988 | B2 | 6/2010 | Thomas et al. |
| 8,672,877 | B2 | 3/2014 | Gust |
| 9,561,002 | B2 | 2/2017 | Lau |
| 2003/0152612 | A1 | 8/2003 | Pugliese et al. |
| 2005/0277912 | A1 | 12/2005 | John |
| 2005/0283327 | A1 | 12/2005 | Bowman et al. |
| 2006/0138371 | A1 | 6/2006 | Garnier |
| 2006/0226108 | A1 | 10/2006 | Dahan et al. |
| 2007/0031486 | A1 * | 2/2007 | Squashic ............... A61K 31/385 424/451 |
| 2007/0250119 | A1 * | 10/2007 | Tyler .................. A61N 1/36014 607/2 |
| 2008/0041859 | A1 * | 2/2008 | Teglbjarg ............. A47J 36/2411 220/592.16 |
| 2008/0167579 | A1 | 7/2008 | Ezra et al. |
| 2008/0287037 | A1 | 11/2008 | Solberg |
| 2009/0198275 | A1 * | 8/2009 | Godown ............... A61J 17/005 606/236 |
| 2010/0127196 | A1 | 5/2010 | Sawada et al. |
| 2011/0087078 | A1 | 4/2011 | Zemel et al. |
| 2011/0126770 | A1 | 6/2011 | Mulder et al. |
| 2012/0252924 | A1 * | 10/2012 | Mahoney ................. C08K 3/36 523/105 |
| 2012/0277794 | A1 * | 11/2012 | Kountotsis ........... A61B 5/6802 606/234 |
| 2013/0270140 | A1 | 10/2013 | Tronson |
| 2014/0199680 | A1 | 7/2014 | Min et al. |
| 2014/0276167 | A1 | 9/2014 | Dasgupta et al. |
| 2014/0288466 | A1 | 9/2014 | Alvarez et al. |
| 2015/0011858 | A1 | 1/2015 | Caluser |
| 2015/0088304 | A1 * | 3/2015 | Ameye ................. A47J 31/404 700/233 |
| 2015/0160212 | A1 | 6/2015 | Maehana et al. |
| 2015/0245737 | A1 | 9/2015 | Chigusa et al. |
| 2015/0283311 | A1 * | 10/2015 | Alvarez ............. A61M 1/0031 604/514 |
| 2016/0120763 | A1 | 5/2016 | Conner et al. |

OTHER PUBLICATIONS

Argentiere et al.; "Smart Microfluidics: The Role of Stimuli-Responsive Polymers in Microfluidic Devices"; Advances in Microfluidics; bearing a date of Mar. 7, 2012; pp. 127-154; InTech.

Ballard et al.; "Human Milk Composition: Nutrients and Bioactive Factors"; National Institute of Health—Pediatr Clin North Am.; Feb. 2013; pp. 1-24; vol. 60, No. 1; Elsevier Inc.

Barzilay et al.; "Micro-Processor based Improved Ultrasonic Direction and Range Finder"; International Journal of Computer Science and Information Technologies; accessed on Mar. 5, 2015; pp. 303-308; vol. 1, No. 4.

Beauchamp et al.; "Flavor Perception in Human Infants: Development and Functional Significance"; Digestion; bearing a date of Mar. 10, 2011; pp. 1-6; vol. 83; S. Karger AG, Basel.

Bosch et al.; "Recent Development in Optical Fiber Biosensors"; Sensors; bearing a date of May 21, 2007; pp. 797-859; vol. 7; MDPI.

Böttner et al.; "New Thermoelectric Components Using Microsystem Technologies"; Journal of Microelectromechanical Systems; Jun. 2004; pp. 414-420; vol. 13, No. 3; IEEE.

Cabrera-Rubio et al.; "The human milk microbiome changes over lactation and is shaped by maternal weight and mode of delivery"; The American Journal of Clinical Nutrition; downloaded on Feb. 23, 2015; pp. 544-551; vol. 96; American Society for Nutrition.

Chawla et al.; "An Overview of Passive RFID"; IEEE Applications & Practice; Sep. 2007; pp. 11-17; IEEE.

Chen et al.; "Metamaterials Application in Sensing"; Sensors; bearing a date of Jan. 5, 2012; pp. 2742-2765; vol. 12.

Chiappin et al.; "Saliva specimen: A new laboratory tool for diagnostic and basic investigation"; Clinica Chimica Acta; bearing a date of Oct. 31, 2006; pp. 30-40; vol. 383; Elsevier B.V.

Collins et al.; "Microfluidic flow transducer based on the measurement of electrical admittance"; Lab on a Chip; bearing a date of Aug. 27, 2003; 12 pages; vol. 4; The Royal Society of Chemistry 2003.

"Compact 2-way Pinch Valves"; ASCO; pp. 32-35; accessed Feb. 24, 2015.

"Conductivity Sensor for various conductivity measurement applications"; Innovative Sensor Technology; downloaded Feb. 24, 2015; pp. 1-2.

Costello et al.; "A review of the volatiles from the healthy human body"; Journal of Breath Research; bearing a date of Jun. 3, 2013; pp. 1-29; vol. 8; IOP Publishing Ltd.

"Drug delivery device solutions"; PEP microPEP; downloaded on Feb. 24, 2015; pp. 1-2; located at http://www.pepmicropep.com/markets/medical-surgical/drug-delivery-device-solutions/; Precision Engineered Products LLC.

Eidelman et al.; "Breastfeeding and the Use of Human Milk"; Pediatrics; Mar. 2012; pp. e827-e841; vol. 129; No. 3; American Academy of Pediatrics.

Fairney et al.; "Studies on the measurement of 25-hydroxy vitamin D in human saliva"; British Journal of Nutrition; bearing a date of Jul. 18, 1986; pp. 13-25; vol. 57.

Finkenzeller, Klaus; "Fundamental Operating Principles"; RFID Handbook: Fundamentals and Applications in Contactless Smart Cards and Identification; downloaded Mar. 4, 2015; pp. 29-59; John Wiley & Sons, Ltd.

Flaga et al.; "Pneumatic Valves Based on Magnetic Shape Memory Alloys: Potential Applications"; 2011 12th International Carpathian Control Conference (ICCC); downloaded Mar. 4, 2015; pp. 111-114; IEEE.

Fu et al.; "TiNi-based thin films in MEMS applications: a review"; Sensors and Actuators a Physical; bearing a date of Feb. 12, 2004; pp. 395-408; vol. 112; Elsevier B.V.

Futagawa et al.; "A Miniature Integrated Multimodal Sensor for Measuring pH, EC and Temperature for Precision Agriculture"; Sensors; bearing a date of Apr. 30, 2012; pp. 8338-8354; vol. 12.

Gutierrez et al.; "Electrochemically-Based Dose Measurement for Closed-Loop Drug Delivery Applications"; Transducers' 11, Beijing, China, Jun. 5-9, 2011; pp. 2839-2842; IEEE.

Hagleitner et al.; "Smart single-chip gas sensor microsystem"; Nature; Nov. 15, 2001; pp. 293-296; vol. 414; Macmillan Magazines Ltd.

(56) References Cited

OTHER PUBLICATIONS

Hardy et al.; "Probiotics, Prebiotics and Immunomodulation of Gut Mucosal Defences: Homeostasis and Immunopathology"; Nutrients; bearing a date of Mar. 5, 2013; pp. 1869-1912; vol. 5.
Hunt et al.; "Characterization of the Diversity and Temporal Stability of Bacterial Communities in Human Milk"; Plos One; Jun. 2011; pp. 1-8; vol. 6, Issue 6.
Innis, Sheila M.; "Human milk: maternal dietary lipids and infant development"; Proceedings of the Nutrition Society; accessed on Mar. 4, 2015; pp. 397-404; vol. 66.
"Interactive DRI for Healthcare Professionals"; USDA National Agricultural Library; printed on Feb. 18, 2015; pp. 1-3; located at: http://fnic.nal.usda.gov/fnic/interactiveDRI/dri_results.php.
Ionov, Leonid; "Hydrogel-based actuators: possibilities and limitations"; Materials Today; Dec. 10, 2014; pp. 494-503; vol. 17, No. 10; Elsevier Ltd.
Järvinen et al.; "Does Low IgA in Human Milk Predispose the Infant to Development of Cow's Milk Allergy?"; Pediatric Research; bearing a date of Aug. 19, 1999; pp. 457-462; vol. 48, No. 4; International Pediatric Research Foundation, Inc.
Joensen et al.; "Exhaled Breath Analysis Using Electronic Nose in Cystic Fibrosis and Primary Ciliary Dyskinesia Patients with Chronic Pulmonary Infections"; Plos One; Dec. 26, 2014; pp. 1-15.
Koletzko et al.; "Global Standard for the Composition of Infant Formula: Recommendations of an ESPGHAN Coordinated International Expert Group"; Journal of Pediatric Gastroenterology and Nutrition; Nov. 2005; pp. 584-599; vol. 41, No. 5; Nov. 2005 ESPGHAN Committee on Nutrition.
Ladabaum et al.; "Miniature drumheads: microfabricated ultrasonic transducers"; Ultrasonics; 1998; accessed on Mar. 4, 2015; pp. 25-29; vol. 36; Elsevier Science B.V.
Lee et al.; "Aptamers as molecular recognition elements for electrical nanobiosensors"; Anal Bioanal Chem; bearing a date of Jul. 3, 2007; pp. 1023-1032; vol. 390; Springer-Verlag.
Li et al.; "A low power, on demand electrothermal valve for wireless drug delivery applications"; Lab on a Chip; bearing a date of May 27, 2009; pp. 101-110; vol. 10; The Royal Society of Chemistry 2010.
Lien et al.; "Microfluidic flow rate detection based on integrated optical fiber cantilever"; Lab on a Chip; bearing a date of May 9, 2007; pp. 1352-1356; vol. 7; The Royal Society of Chemistry 2007.
Lou et al.; "Microfiber Optical Sensors: A Review"; Sensors; bearing a date of Jan. 6, 2014; pp. 5823-5844; vol. 14.
Mamta et al.; "Oral fluid: Biochemical composition and functions: A Review"; Journal of Pharmaceutical and Biomedical Sciences; Dec. 2013; pp. 1932-1941, vol. 37.

Miller et al.; "Controversies Concerning Vitamin K and the Newborn"; Pediatrics; Jul. 2003; pp. 191-192; vol. 112, No. 1; American Academy of Pediatrics.
"MTCH6301 Projected Capacitive Touch Controller"; Microchip; uploaded Feb. 24, 2015; pp. 1-32; 2012 Microchip Technology Inc.
Nisar et al.; "MEMS-based micropumps in drug delivery and biomedical applications"; Sensors and Actuators B Chemical; bearing a date of Jul. 21, 2007; pp. 917-942; vol. 130; Elsevier B.V.
Price et al.; "Development of membrane systems based on conducting polymers"; Synthetic Metals; 1999; accessed Feb. 24, 2015; pp. 1338-1341; vol. 102; Elsevier Science S.A.
Prieto et al.; "Sucking pressure and its relationship to milk transfer during breastfeeding in humans"; Journal of Reproduction and Fertility; bearing a date of Feb. 5, 1996; pp. 69-74; vol. 108; Journals of Reproduction and Fertility Ltd.
Qiu et al.; "Environment-sensitive hydrogels for drug delivery"; Advanced Drug Delivery Reviews; bearing a date of Aug. 14, 2001; pp. 321-339; vol. 53; Elsevier Science B.V.
Rodriguez et al.; "Edited by WFB Safety and efficacy of cyproheptadine for treating dyspeptic symptoms in children"; J Pediatr.; bearing a date of Jul. 1, 2014; pp. 1-16; vol. 163 No. 1; Mosby, Inc.
Sample et al.; Design of an RFID-Based Battery-Free Programmable Sensing Platform; IEEE Transactions on Instrumentation and Measurement; Nov. 2008; pp. 2608-2615; vol. 57, No. 11; IEEE.
Sánchez et al.; "The possible role of human milk nucleotides as sleep inducers"; Nutritional Neuroscience; 2009; bearing a date of Mar. 25, 2008; pp. 2-8; vol. 12, No. 1; W.S. Maney & Son Ltd.
Sharma et al.; "Miniature Radar for Mobile Devices"; uploaded Mar. 5, 2015; 8 pages; IEEE.
So et al.; Single-Walled Carbon Nanotube Biosensors Using Aptamers as Molecular Recognition Elements; JACS Communications, J. Am. Chem. Soc.; bearing a date of Aug. 6, 2005; pp. 11906-11907; vol. 127, No. 34; American Chemical Society.
Tao et al.; "Metamaterials on Paper as a Sensing Platform"; Advanced Materials; bearing a date of Jan. 15, 2011; 12 pages; WILEY-VCH Verlag GmbH & Co.
Vashist, Sandeep Kumar; "A Review of Microcantilevers for Sensing Applications"; AZojono Journal of Nanotechnology Online; Jun. 2007; pp. 1-15; vol. 3.
Ventura et al.; "Early Influences on the Development of Food Preferences"; Current Biology; May 6, 2013; pp. R401-R408; vol. 23, No. 9; Elsevier Ltd.
Wagner et al.; "Prevention of Rickets and Vitamin D Deficiency in Infants, Children, and Adolescents"; American Academy of Pediatrics; Nov. 2008; pp. 1142-1152; vol. 122, No. 5; American Academy of Pediatrics.
Wilson et al.; "Advances in Electronic-Nose Technologies Developed for Biomedical Applications"; Sensors; bearing a date of Sep. 30, 2010; pp. 1105-1176; vol. 11.

\* cited by examiner

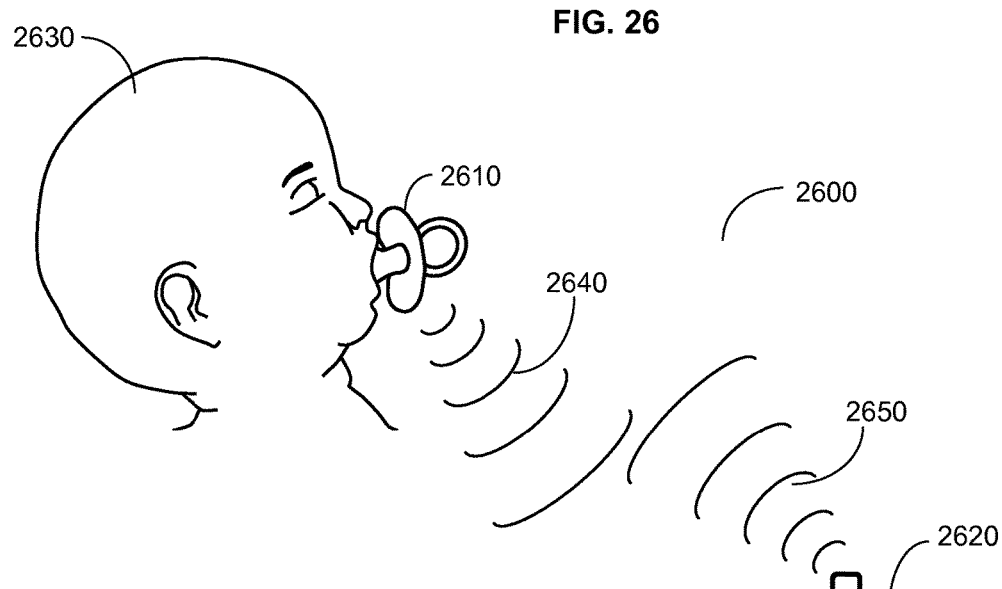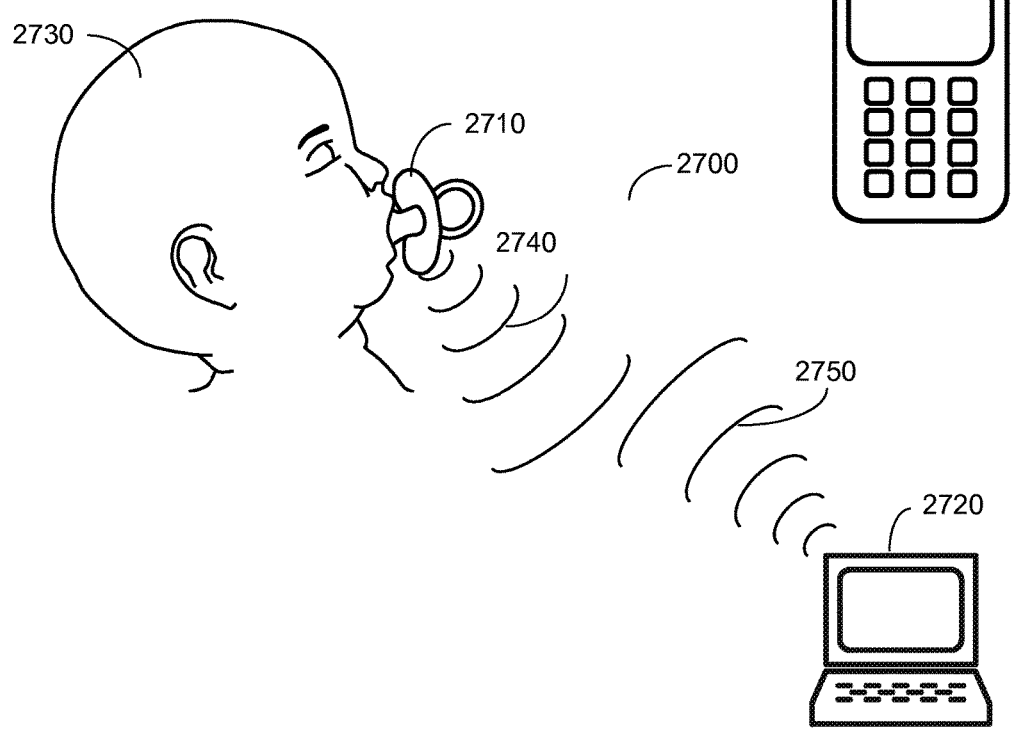

2810 Receiving information associated with a breast milk supplement regimen with a breast milk supplement delivery device, the breast milk supplement delivery device including a substrate sized for placement on a surface of a breast region of a lactating female, at least one supplement reservoir associated with the substrate and adapted to contain one or more breast milk supplements, the at least one supplement reservoir including a port with a controllable valve, a data storage component configured to store the breast milk supplement regimen, and a control unit including a microprocessor and circuitry, the control operably coupled to the data storage component and to the controllable valve of the at least one supplement reservoir 2820 Actuating the controllable valve of the at least one supplement reservoir to modulate release of the one or more breast milk supplements based on the received breast milk supplement regimen

2810 Receiving information associated with a breast milk supplement regimen with a breast milk supplement delivery device > 2900 Wirelessly receiving the information associated with the breast milk supplement regimen > 2910 Receiving the information associated with the breast milk supplement regimen from a removable data storage component > 2920 Receiving the information associated with the breast milk supplement regimen through a user interface associated with the breast milk supplement delivery device

2820 Actuating the controllable valve of the at least one supplement reservoir to modulate release of one or more breast milk supplements based on the received breast milk supplement regimen > 2930 Actuating the controllable valve to at least partially open or close the controllable valve > 2940 Actuating the controllable valve to at least one of open the controllable valve, close the controllable valve, change a pressure threshold of the controllable valve, increase an opening size of the controllable valve, decrease an opening size of the controllable valve, or alter a permeability or porosity of the controllable valve > 2950 Actuating the controllable valve to modulate release of a specified amount of the one or more breast milk supplements during a feeding event > 2960 Actuating the controllable valve to modulate release of a specified cumulative amount of the one or more breast milk supplements over a plurality of feeding events > 2970 Actuating the controllable valve to modulate release of a specified cumulative amount of the one or more breast milk supplements over a plurality of feeding events within a specified time period > 2980 Actuating the controllable valve to cease release of the one or more breast milk supplements once a specified amount of the one or more breast milk supplements has been delivered

| 2810 Receiving information associated with a breast milk supplement regimen with a breast milk supplement delivery device |

3000 Recording a delivery event with at least one delivery event sensor

3005 Recording at least one of a breast milk supplement type, a dosage, an infant identifier, a time, or a date 3010 Reporting a delivery event 3015 Reporting at least one of a breast milk supplement type, a dosage, an infant identifier, a time, or a date 3020 Reporting the delivery event through at least one of a radiofrequency transmission, a radiofrequency identification transmission, an optical transmission, or an audio transmission 3025 Reporting the delivery event through at least one of an electrical wire, an optical fiber, or a removable storage medium 3030 Reporting the delivery event to a computing device 3035 Reporting the delivery event to a personal electronic device 3040 Reporting the delivery event to a user interface associated with the breast milk supplement delivery device 3045 Adjusting the breast milk supplement regimen 3050 Adjusting the breast milk supplement regimen based on attributes of an infant 3055 Adjusting the breast milk supplement regimen based on at least one of age, weight, genome, gender, ethnicity, medical condition, or nutritional need of the infant 3060 Adjusting the breast milk supplement regimen based on a quality of breast milk of the lactating female 3065 Adjusting the breast milk supplement regimen based on at least one of a nutritional quality, microbial quality, or immunological quality of the breast milk of the lactating female

| 2820 Actuating the controllable valve of the at least one supplement reservoir to modulate release of one or more breast milk supplements based on the received breast milk supplement regimen |

2810 Receiving information associated with a breast milk supplement regimen with a breast milk supplement delivery device 3100 Receiving information associated with at least one analyte from an analyte sensor associated with the breast milk supplement delivery device 3110 Receiving information associated with at least one saliva analyte, at least one breast milk analyte, or at least one exhaled breath analyte 3120 Receiving the information associated with the at least one analyte from at least one of a saliva analyte sensor, a breast milk analyte sensor, or an exhaled breath analyte sensor 3130 Adjusting the breast milk supplement regimen in response to the received information associated with the at least one analyte 3140 Actuating the controllable valve of the at least one supplement reservoir to modulate release of the one or more breast milk supplements based on the adjusted breast milk supplement regimen 3150 Receiving information associated with a proximity of an infant to the breast milk supplement delivery device with an infant presence detector and actuating the controllable valve of the at least one supplement reservoir in response to the received information associated with the proximity of the infant.

3160 Vibrating at least a portion of the breast milk supplement delivery device

3170 At least one of heating and cooling at least a portion of the breast milk supplement delivery device 3000 Recording a delivery event with at least one delivery event sensor 3010 Reporting a delivery event 2820 Actuating the controllable valve of the at least one supplement reservoir to modulate release of one or more breast milk supplements based on the received breast milk supplement regimen

3210 Receiving information associated with at least one analyte from an analyte sensor incorporated into a breast milk supplement delivery device, the breast milk supplement delivery device including the analyte sensor, a substrate sized for placement on a surface of a breast region of a lactating female, at least one supplement reservoir associated with the substrate and adapted to contain one or more breast milk supplements, the at least one supplement reservoir including a port with a controllable valve, and a control unit including a microprocessor and circuitry, the control unit operably coupled to the analyte sensor and the controllable valve of the at least one supplement reservoir 3220 Actuating the controllable valve of the at least one supplement reservoir to modulate release of the one or more breast milk supplements in response to the received information associated with the at least one analyte

3210 Receiving information associated with at least one analyte from an analyte sensor 3300 Receiving information associated with at least one breast milk analyte from a breast milk analyte sensor 3305 Receiving information associated with at least one saliva analyte from a saliva analyte sensor 3310 Receiving information associated with at least one exhaled breath analyte from an exhaled breath analyte sensor 3315 Recording a delivery event with at least one delivery event sensor 3320 Recording at least one of a breast milk supplement type, a dosage, an infant identifier, a time, or a date 3325 Reporting a delivery event 3330 Reporting the delivery event through at least one of a radiofrequency transmission, a radiofrequency identification (RFID) transmission, an optical transmission, or an audio transmission 3335 Reporting the delivery event through at least one of an electrical wire, an optical fiber, or a removable storage medium 3340 Reporting the delivery event to a computing device 3345 Reporting the delivery event to a personal electronic device 3350 Reporting the delivery event to a user interface associated with the breast milk supplement delivery device 3220 Actuating the controllable valve of the at least one supplement reservoir to modulate release of the one or more breast milk supplements in response to the received information associated with the at least one analyte 3355 Actuating the controllable valve to at least partially open or close the controllable valve 3360 Actuating the controllable valve to at least one of open the controllable valve, close the controllable valve, change a pressure threshold of the controllable valve, increase an opening size of the controllable valve, decrease an opening size of the controllable valve, or alter a permeability or porosity of the controllable valve

| 3210 Receiving information associated with at least one analyte from an analyte sensor |

> 3400 Receiving information associated with a breast milk supplement regimen
>
>> 3410 Wirelessly receiving the information associated with the breast milk supplement regimen
>>
>> 3420 Receiving the information associated with the breast milk supplement regimen from a removable data storage component
>>
>> 3430 Receiving the information associated with the breast milk supplement regimen through a user interface associated with the breast milk supplement delivery device
>>
>> 3440 Receiving information associated with a breast milk supplement regimen personalized for attributes of at least one infant
>>
>> 3450 Receiving information associated with a breast milk supplement regimen personalized for a quality of breast milk of the lactating female
>>
>> 3460 Modifying the breast milk supplement regimen in response to the received information associated with the at least one analyte; and actuating the controllable valve of at least one of the one or more supplement reservoirs to modulate release of the one or more breast milk supplements in response to the modified breast milk supplement regimen > 3470 Receiving information associated with a proximity of an infant to the breast milk supplement delivery device with an infant presence detector and actuating the controllable valve of the at least one supplement reservoir in response to the received information associated with the proximity of the infant > 3480 Vibrating at least a portion of the breast milk supplement delivery device > 3490 At least one of heating or cooling at least a portion of the breast milk supplement delivery device

| 3220 Actuating the controllable valve of the at least one supplement reservoir to modulate release of the one or more breast milk supplements in response to the received information associated with the at least one analyte |

FIG. 35

| |
|---|
| 3500 A system for controlling delivery of breast milk supplementation to an infant |
| 3510 Circuitry for receiving information associated with a breast milk supplement regimen |
| 3520 Circuitry for actuating a controllable valve of at least one of one or more supplement reservoirs associated with a breast milk supplement delivery device to modulate release of one or more breast milk supplements from the at least one of the one or more supplement reservoirs based on the received breast milk supplement regimen |

FIG. 36

3500 A system for controlling delivery of breast milk supplementation to an infant 3510 Circuitry for receiving information associated with a breast milk supplement regimen 3610 Circuitry for wirelessly receiving the information associated with the breast milk supplement regimen 3600 Computing Component

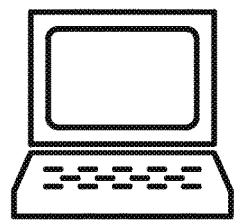

3620 Circuitry for receiving information from a delivery event sensor

3630 Circuitry for recoding a delivery event with a delivery event sensor

3640 Circuitry for reporting a delivery event

3660 Circuitry for receiving information associated with at least one analyte from an analyte sensor 3670 Circuitry for modifying the breast milk supplement regimen in response to the received information associated with the at least one analyte; and circuitry for actuating the controllable valve of at least one of the one or more supplement reservoirs associated with the breast milk supplement delivery device to modulate release of one or more breast milk supplements based on the modified breast milk supplement regimen 3520 Circuitry for actuating a controllable valve of at least one of one or more supplement reservoirs associated with a breast milk supplement delivery device to modulate release of one or more breast milk supplements from the at least one of the one or more supplement reservoirs based on the received breast milk supplement regimen

FIG. 37

| 3700 A system for controlling delivery of breast milk supplementation to an infant |
|---|
| 3710 Circuitry for receiving information associated with at least one analyte from an analyte sensor incorporated into a breast milk supplement delivery device |
| 3720 Circuitry for actuating a controllable valve of at least one of one or more supplement reservoirs associated with the breast milk supplement delivery device to modulate release of one or more breast milk supplements in response to the received information associated with the at least one analyte |

FIG. 38

3700 A system for controlling delivery of breast milk supplementation to an infant 3710 Circuitry for receiving information associated with at least one analyte from an analyte sensor incorporated into a breast milk supplement delivery device 3810 Circuitry for receiving information associated with at least one saliva analyte from a saliva analyte sensor 3820 Circuitry for receiving information associated with at least one breast milk analyte from a breast milk analyte sensor 3830 Circuitry for receiving information associated with at least one exhaled breath analyte from an exhaled breath analyte sensor

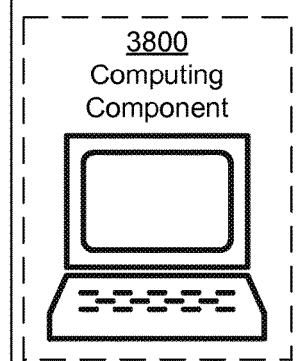

3800 Computing Component

3840 Circuitry for receiving information from a delivery event sensor

3850 Circuitry for recoding a delivery event with a delivery event sensor

3860 Circuitry for reporting a delivery event

3870 Circuitry for receiving information associated with a breast milk supplement regimen 3720 Circuitry for actuating a controllable valve of at least one of one or more supplement reservoirs associated with a breast milk supplement delivery device to modulate release of one or more breast milk supplements in response to the received information associated with the at least one analyte

SYSTEMS AND DEVICES FOR CONTROLLING DELIVERY OF BREAST MILK SUPPLEMENTATION

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority application(s)).

PRIORITY APPLICATIONS

NONE

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a breast milk supplement delivery device includes, but is not limited to, a substrate sized for placement on a surface of a breast region of a lactating female; one or more supplement reservoirs associated with the substrate, at least one of the one or more supplement reservoirs including a port with a controllable valve; a data storage component including a breast milk supplement regimen; and a control unit including a microprocessor and circuitry, the control unit operably coupled to the data storage component and to the controllable valve of the at least one of the one or more supplement reservoirs, the circuitry including actuation circuitry configured to actuate the controllable valve of the at least one of the one or more supplement reservoirs based on the breast milk supplement regimen. In addition to the foregoing, other aspects of a breast milk supplement delivery device are described in the claims, drawings, and text forming a part of the present disclosure.

In an aspect, a breast milk supplement delivery device includes, but is not limited to, a substrate sized for placement on a surface of a breast region of a lactating female in proximity to at least one nipple; and at least one flavoring associated with the substrate, the at least one flavoring intended to acclimate an infant to a food associated with the at least one flavoring. In addition to the foregoing, other aspects of a breast milk supplement delivery device are described in the claims, drawings, and text forming a part of the present disclosure.

In an aspect, a breast milk supplement delivery system includes, but is not limited to, a reusable component including a substrate sized for placement on a surface of a breast region of a lactating female, a data storage component configured to store a breast milk supplement regimen, and a control unit including a microprocessor and circuitry, the control unit operably coupled to the data storage component, the circuitry including actuation circuitry; and at least one disposable component configured to reversibly attach to the reusable component, the at least one disposable component including one or more supplement reservoirs, at least one of the one or more supplement reservoirs including a port with a controllable valve; wherein the actuation circuitry is configured to actuate the controllable valve of the at least one of the one or more supplement reservoirs based on the breast milk supplement regimen. In addition to the foregoing, other aspects of a breast milk supplement delivery system are described in the claims, drawings, and text forming a part of the present disclosure.

In an aspect, a breast milk supplement delivery device includes, but is not limited to, a substrate sized for placement on a surface of a breast region of a lactating female; one or more supplement reservoirs associated with the substrate, at least one of the one or more supplement reservoirs including a port with a controllable valve, the one or more supplement reservoirs adapted to contain one or more breast milk supplements; one or more analyte sensors associated with the substrate; and a control unit operably coupled to the controllable valve of the at least one of the one or more supplement reservoirs and to the one or more analyte sensors, the control unit including a microprocessor and circuitry, the circuitry including circuitry configured to receive analyte information from the one or more analyte sensors; and actuate the controllable valve of the at least one of the one or more supplement reservoirs to modulate release of the one or more breast milk supplements in response to the received analyte information. In addition to the foregoing, other aspects of a breast milk supplement delivery device are described in the claims, drawings, and text forming a part of the present disclosure.

In an aspect, a breast milk supplement delivery device includes, but is not limited to, a housing sized for placement on a surface near a breast region of a lactating female, the housing including one or more supplement reservoirs, at least one of the one or more supplement reservoirs including a port with a controllable valve; a data storage component including a breast milk supplement regimen; and a control unit including a microprocessor and circuitry, the control unit operably coupled to the data storage component and to the controllable valve of the at least one of the one or more supplement reservoirs, the circuitry including actuation circuitry configured to actuate the controllable valve of the at least one of the one or more supplement reservoirs based on the breast milk supplement regimen; and at least one delivery tube having a first end and a second end, the first end of the at least one delivery tube in fluid communication with the port with the controllable valve, the second end of the at least one delivery tube configured for placement in proximity to a nipple of the lactating female. In addition to the foregoing, other aspects of a breast milk supplement delivery device are described in the claims, drawings, and text forming a part of the present disclosure.

In an aspect, a breast milk supplement delivery device includes, but is not limited to, a housing including one or more supplement reservoirs, at least one of the one or more supplement reservoirs including a port with a controllable valve; and a control unit including a microprocessor and circuitry, the control unit operably coupled to the controllable valve of the at least one of the one or more supplement reservoirs, the circuitry including actuation circuitry configured to actuate the controllable valve of the at least one of the one or more supplement reservoirs; a flexible delivery tube including a first end and a second end, the first end of the flexible delivery tube in fluid communication with the port, the second end of the flexible delivery tube configured for placement in proximity to a nipple of a lactating female; and at least one analyte sensor associated with the second end of the flexible delivery tube and operably coupled to the control unit. In addition to the foregoing, other aspects of a breast milk supplement delivery device are described in the claims, drawings, and text forming a part of the present disclosure.

In an aspect, a breast milk supplement delivery device includes, but is not limited to, a nipple component sized for placement in an infant's mouth, the nipple component having a first end and a second end, the first end of the nipple component including an aperture; a guard component attached to the second end of the nipple component; a supplement reservoir including a port with a controllable valve, the supplement reservoir adapted to contain one or more breast milk supplements; a flow conduit disposed within at least a portion of the nipple component, a first end of the flow conduit in fluid communication with the aperture on the first end of the nipple component and a second end of the flow conduit in fluid communication with the port of the supplement reservoir; a data storage component including a breast milk supplement regimen; and a control unit including a microprocessor and circuitry, the control unit operably coupled to the controllable valve and to the data storage component, the circuitry including actuation circuitry configured to actuate the controllable valve to modulate release of the one or more breast milk supplements from the supplement reservoir based on the breast milk supplement regimen. In addition to the foregoing, other aspects of a breast milk supplement delivery device are described in the claims, drawings, and text forming a part of the present disclosure.

In an aspect, a breast milk supplement delivery device includes, but is not limited to, a nipple component sized for placement in an infant's mouth, the nipple component having a first end and a second end, the first end of the nipple component including an aperture; a guard component attached to the second end of the nipple component; a supplement reservoir including a port with a controllable valve, the supplement reservoir adapted to contain one or more breast milk supplements; a flow conduit disposed within at least a portion of the nipple component, a first end of the flow conduit in fluid communication with the aperture on the first end of the nipple component and a second end of the flow conduit in fluid communication with the port of the supplement reservoir; one or more analyte sensors associated with at least one of the nipple component and the guard component; and a control unit including a microprocessor and circuitry, the control unit operably coupled to the controllable valve and to the one or more analyte sensors, the circuitry including actuation circuitry configured to actuate the controllable valve. In addition to the foregoing, other aspects of a breast milk supplement delivery device are described in the claims, drawings, and text forming a part of the present disclosure.

In an aspect, a breast milk supplement delivery system includes, but is not limited to, a delivery unit including a nipple component sized for placement in an infant's mouth, the nipple component having a first end and a second end, the first end of the nipple component including an aperture; a guard component attached to the second end of the nipple component; a supplement reservoir including a port with a controllable valve, the supplement reservoir adapted to contain one or more breast milk supplements; and a flow conduit disposed within at least a portion of the nipple component, a first end of the flow conduit in fluid communication with the aperture on the first end of the nipple component and a second end of the flow conduit in fluid communication with the port of the supplement reservoir; a breast milk supplement regimen; and a control unit including a microprocessor and circuitry, the control unit including actuation circuitry configured to wirelessly actuate the controllable valve of the supplement reservoir to modulate release of the one or more breast milk supplements based on the breast milk supplement regimen. In addition to the foregoing, other aspects of a breast milk delivery system are described in the claims, drawings, and text forming a part of the present disclosure.

In an aspect, a method for controlling delivery of breast milk supplementation includes, but is not limited to, receiving information associated with a breast milk supplement regimen with a breast milk supplement delivery device, the breast milk supplement delivery device including a substrate sized for placement on a surface of a breast region of a lactating female, at least one supplement reservoir associated with the substrate and adapted to contain one or more breast milk supplements, the at least one supplement reservoir including a port with a controllable valve, a data storage component configured to store the breast milk supplement regimen, and a control unit including a microprocessor and circuitry, the control unit operably coupled to the data storage component and to the controllable valve of the at least one supplement reservoir; and actuating the controllable valve of the at least one supplement reservoir to modulate release of the one or more breast milk supplements based on the received breast milk supplement regimen. In addition the foregoing, other aspects of a method are described in the claims, drawings, and text forming a part of the present disclosure.

In an aspect, a method for controlling delivery of breast milk supplementation includes, but is not limited to, receiving information associated with at least one analyte with an analyte sensor incorporated into a breast milk supplement delivery device, the breast milk supplement delivery device including the analyte sensor, a substrate sized for placement on a surface of a breast region of a lactating female, at least one supplement reservoir associated with the substrate and adapted to contain one or more breast milk supplements, the at least one supplement reservoir including a port with a controllable valve, and a control unit including a microprocessor and circuitry, the control unit operably coupled to the analyte sensor and to the controllable valve of the at least one supplement reservoir; and actuating the controllable valve of the at least one supplement reservoir to modulate release of the one or more breast milk supplements in response to the received information associated with the at least one analyte. In addition to the foregoing, other aspects of a method are described in claims, drawings, and text forming a part of the present disclosure.

In an aspect, a system for controlling delivery of breast milk supplementation to an infant includes, but is not limited to, circuitry for receiving information associated with a breast milk supplement regimen; and circuitry for actuating a controllable valve of at least one of one or more supplement reservoirs associated with a breast milk supplement delivery device to modulate release of one or more breast milk supplements from the at least one of the one or more supplement reservoirs based on the received breast milk supplement regimen. In addition to the foregoing, other aspects of a system are described in claims, drawings, and text forming a part of the present disclosure.

In an aspect, a system for controlling delivery of breast milk supplementation to an infant includes, but is not limited to, circuitry for receiving information associated with at least one analyte from an analyte sensor incorporated into a breast milk supplement delivery device; and circuitry for actuating a controllable valve of at least one of one or more supplement reservoirs associated with the breast milk supplement delivery device to modulate release of one or more breast milk supplements in response to the received information associated with the at least one analyte. In addition to the foregoing, other aspects of a system are described in claims, drawings, and text forming a part of the present disclosure.

In an aspect, a system for controlling delivery of breast milk supplementation includes, but is not limited to, a control unit including a processor; and non-transitory signal-bearing medium bearing one or more instructions for controllable delivery of breast milk supplementation to a nursing infant, the non-transitory signal-bearing medium including one or more instructions for receiving information associated with a breast milk supplement regimen; and one or more instructions for actuating a controllable valve of at least one of one or more supplement reservoirs associated with a breast milk supplement delivery device to modulate release of one or more breast milk supplements from the at least one of the one or more supplement reservoirs based on the received breast milk supplement regimen. In addition to the foregoing, other aspects of a system are described in claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 26 illustrates an embodiment of a breast milk supplement delivery system including a delivery unit and a personal electronic device.

FIG. 27 illustrates an embodiment of a breast milk supplement delivery system including a delivery unit and computing device.

FIG. 28 is a flow diagram of an embodiment of a method for delivery of breast milk supplementation.

FIG. 29 illustrates further aspects of a method such as shown in FIG. 28.

FIG. 30 shows further aspects of a method such as depicted in FIG. 28.

FIG. 31 shows further aspects of a method such as depicted in FIG. 28.

FIG. 32 is a flow diagram of an embodiment of a method for delivery of breast milk supplementation.

FIG. 33 illustrates further aspects of a method such as shown in FIG. 32.

FIG. 34 shows further aspects of a method such as depicted in FIG. 32.

FIG. 35 illustrates an embodiment of a system for controlling delivery of breast milk supplementation to an infant.

FIG. 36 illustrates further aspects of a system such as shown in FIG. 35.

FIG. 37 illustrates an embodiment of a system for controlling delivery of breast milk supplementation to an infant.

FIG. 38 illustrates further aspects of a system such as shown in FIG. 37.

DETAILED DESCRIPTION

Figure 1A:
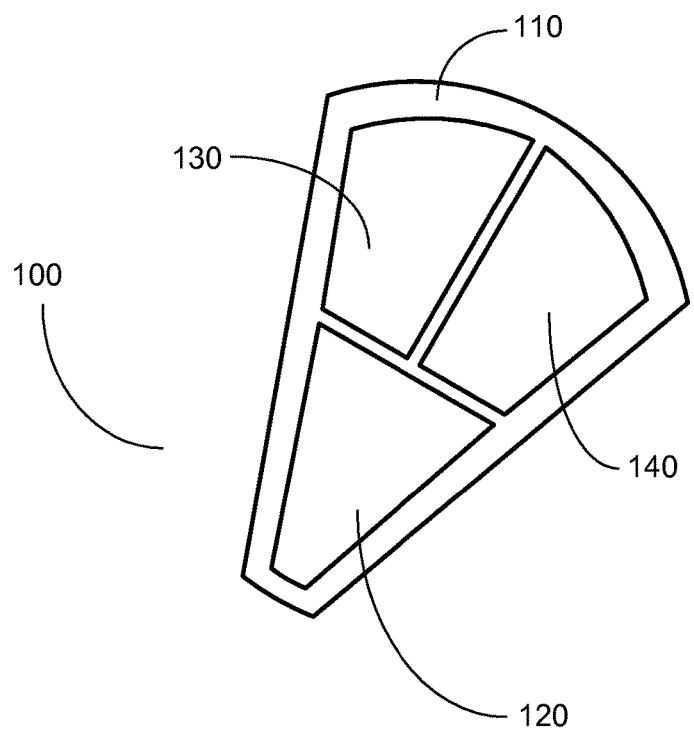
FIG. 1A illustrates an embodiment of a breast milk supplement delivery device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Breastfeeding and human milk are considered the normative standards for infant feeding and nutrition. See, e.g., American Academy of Pediatrics (2012) "Breastfeeding and Use of Human Milk," Pediatrics 129:e827-e841, which is incorporated herein by reference. Short- and long-term benefits of breastfeeding on health have been documented and include reduction in the incidence of gastrointestinal tract infections, respiratory tract infections, otitis media, necrotizing enterocolitis, sudden infant death syndrome, allergic disease, celiac disease, inflammatory bowel disease, obesity, and diabetes. However, in some instances, breast milk may not provide the optimal nutrition to the infant. In such cases, supplementation may be recommended or required.

Described herein are devices, systems, and methods for providing supplements to a nursing infant during breastfeeding.

With reference now to FIG. 1A, shown is an example of a breast milk supplement delivery device 100, which can serve as a context for introducing one or more processes and/or devices described herein. Breast milk supplement delivery device 100 includes substrate 110 sized for placement on a surface of a breast region of a lactating female. In this non-limiting example, substrate 110 comprises a planar wedge-like structure. Breast milk supplement delivery device 100 includes one or more supplement reservoirs 120 associated with substrate 110, at least one of the one or more supplement reservoirs 120 including a port with a controllable valve. Breast milk supplement delivery device 100 further includes a data storage component 130 including a breast milk supplement regimen. In an aspect, the breast milk supplement regimen includes a listing of one or more breast milk supplements and dosing and timing information for each of said one or more breast milk supplements. Breast milk supplement delivery device 100 includes control unit 140 including a microprocessor and circuitry. Control unit 140 is operably coupled to data storage component 130 and to the controllable valve of the at least one of the one or more supplement reservoirs 120. The circuitry of control unit 140 includes actuation circuitry configured to actuate the controllable valve of the at least one of the one or more supplement reservoirs 120 based on the breast milk supplement regimen.

Figure 1B:
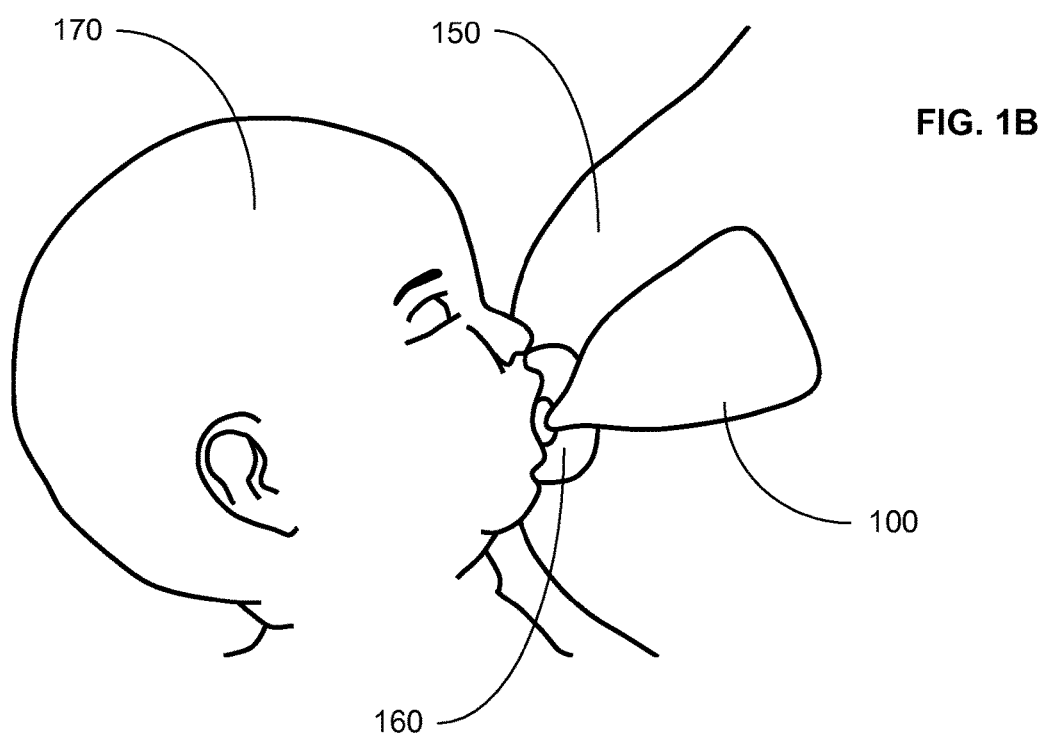
FIG. 1B illustrates placement of an embodiment of a breast milk supplement delivery device such as shown in FIG. 1A on a breast region of a lactating female.

FIG. 1B illustrates a non-limiting example of placement of a breast milk supplement delivery device on a surface of a breast region of a lactating female. Breast milk supplement delivery device 100 is shown placed on the surface of breast 150 of a lactating female. At least a portion of breast milk supplement delivery device 100 is in close proximity to nipple 160. In some embodiments, placement of the breast milk supplement delivery device on the breast region of the lactating female brings at least a portion of the breast milk supplement delivery device in direct contact with the nipple of the lactating female. Also shown is infant 170 suckling nipple 160. The mouth of the infant 170 as he/she suckles is in close proximity to at least a portion of the breast milk supplement delivery device 100. In an aspect, the nursing infant ingests one or more breast milk supplements released from the breast milk supplement delivery device while suckling on the nipple of the lactating female.

The breast milk supplement delivery device is configured to controllably release one or more breast milk supplements to a breastfeeding infant according to the breast milk supplement regimen. In some embodiments, the breast milk supplement delivery device is configured for single use, e.g., during a single nursing event. In some embodiments, the breast milk supplement delivery device is configured for multiple uses during the course of a set number of hours or during the course of a day. In some embodiments, the breast milk supplement delivery device is configured for use over a longer period of time, e.g., several days, a week, several weeks, a month, etc. In some embodiments, one or more components of the breast milk supplement delivery device are reusable while one or more other components of the breast milk supplement delivery device are disposable. For example, the data storage component and/or the control unit attached to a substrate may be reusable while the one or more supplement reservoirs are replaced as needed.

Substrate

In some embodiments, a breast milk supplement delivery device includes a substrate sized for placement on a surface of a breast region of a lactating female. In an aspect, the substrate comprises a substantially two-dimensional structure. In an aspect, the substrate comprises a substantially planar structure. In an aspect, the substrate comprises a flexible substrate. In an aspect, the substrate comprises a patch-like structure. For example, the substrate can take the form of a patch, an applique, a dressing, or a covering. In an aspect, the substrate is sized for placement on a surface of a breast region of a lactating female in close proximity to a nipple. In an aspect, at least one edge of the substrate is adapted for positioning in proximity to the nipple of the lactating female. In an aspect, the at least one edge of the substrate abuts an edge of the nipple. In an aspect, the substrate is configured for placement over at least a portion of the areola of a breast.

Figure 2A:
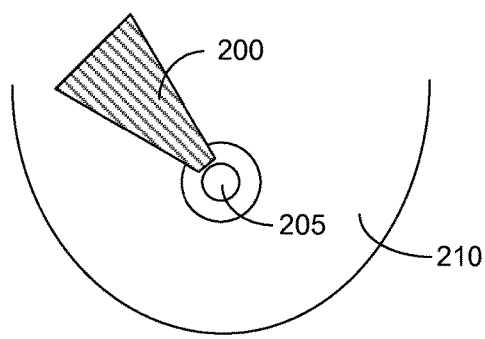
FIG. 2A illustrates an embodiment of a breast milk supplement delivery device.
Figure 2B:
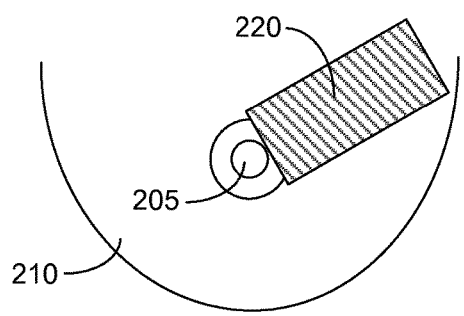
FIG. 2B illustrates an embodiment of a breast milk supplement delivery device.
Figure 2C:
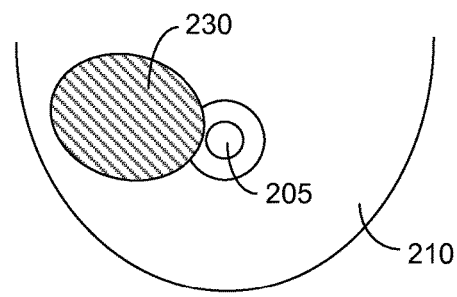
FIG. 2C illustrates an embodiment of a breast milk supplement delivery device.

In an aspect, the substrate can include any of a number of sides or shapes. For example, the substrate can be a circle, an oval, a triangle, a rectangle, a square, a trapezoid, a wedge, or a polygon. In an aspect, the substrate includes three or more edges. In an aspect, the substrate includes three or more straight edges. In an aspect, the substrate includes a combination one or more straight edges and one or more curved edges. FIGS. 2A-2H illustrate non-limiting examples of shapes and sizes. In an aspect, the substrate is a wedge or triangular shape. As illustrated in FIG. 2A, the substrate can take the form of a wedged substrate 200. The wedged substrate 200 is shown placed on a breast region 210, an edge of which is in close proximity to nipple 205. In this non-limiting example, the shortest edge of the substrate is positioned adjacent to the nipple. However, the substrate can be configured such that any edge of the substrate can be positioned adjacent to the nipple. In an aspect, the substrate can take the form of a rectangle or a square. As illustrated in FIG. 2B, the substrate can take the form of a rectangular substrate 220. Rectangular substrate 220 is shown placed on a breast region 210, an edge of the rectangular substrate in close proximity to nipple 205. In an aspect, the substrate can take the form of a circle or oval. As illustrated in FIG. 2C, the substrate can take the form of an oval substrate 230. Oval substrate 230 is shown placed on a breast region 210, an edge of the oval substrate in close proximity to nipple 205.

Figure 2D:
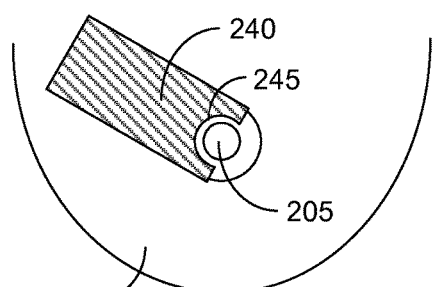
FIG. 2D illustrates an embodiment of a breast milk supplement delivery device.
Figure 2E:
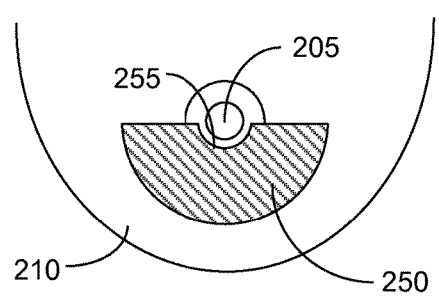
FIG. 2E illustrates an embodiment of a breast milk supplement delivery device.

In an aspect, the substrate includes an edge formed to provide greater contact with the nipple when the substrate is placed on the surface of the breast region of the lactating female. In an aspect, the substrate includes at least one curved edge. In an aspect, the substrate includes a curved edge that at least partially surrounds the nipple when the substrate is placed on the surface of the breast region of the lactating female. In an aspect, the substrate includes a notch, e.g., a semi-circular notch, that allows the substrate to fit snuggly around at least a portion of the nipple. In an aspect, the substrate includes a shape with two or more straight edges and a curved edge configured to at least partially surround the nipple. For example, the substrate can include a rectangle, one edge of which includes a curved edge configured to at least partially surround a nipple. A non-limiting example is illustrated in FIG. 2D. Shown is a rectangular substrate 240 with a curved edge 245. Rectangular substrate 240 is configured for placement on a breast region 210. The curved edge 245 of rectangular substrate 240 is shown at least partially surrounding nipple 205. In an aspect, the substrate includes at least a portion of a circle that includes a curved edge configured to at least partially surround the nipple. For example, the substrate can include a curved wedge shape, one edge of which includes a curved edge configured to at least partially surround a nipple. A non-limiting example is illustrated in FIG. 2E. Curved wedge 250 is configured for placement on a breast region 210. The curved edge 255 of curved wedge 250 is shown at least partially surrounding nipple 205.

Figure 2F:
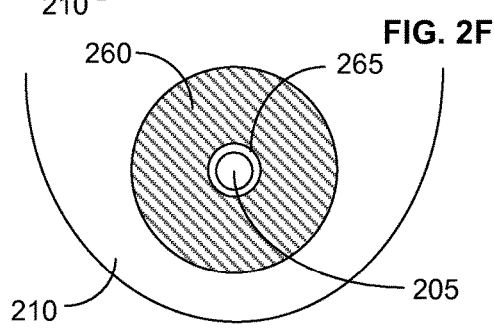
FIG. 2F illustrates an embodiment of a breast milk supplement delivery device.
Figure 2G:
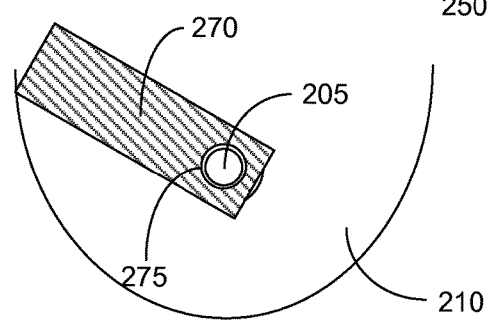
FIG. 2G illustrates an embodiment of a breast milk supplement delivery device.
Figure 2H:
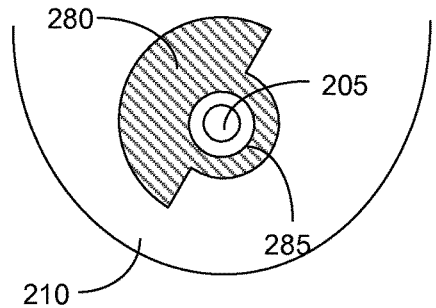
FIG. 2H illustrates an embodiment of a breast milk supplement delivery device.

In an aspect, the substrate completely surrounds the nipple. In an aspect, the substrate completely surrounds the nipple without otherwise covering the nipple. In an aspect, the substrate includes a circular or oval structure including an opening defined by the substrate, the opening sized to accommodate a nipple. In an aspect, the substrate includes a toroid shape. For example, the substrate can be toroid in shape and include a central opening configured to allow exposure of a nipple through an otherwise covered breast. A non-limiting example is illustrated in FIG. 2F. Toroid substrate 260 is configured for placement on a breast region 210. The opening 265 defined by the toroid is shown surrounding nipple 205. In an aspect, the substrate includes a rectangular structure including an opening defined by the substrate, the opening sized to accommodate a nipple. A non-limiting example is illustrated in FIG. 2G. Rectangular substrate 270 is configured for placement on a breast region 210. The opening 275 defined by the rectangle is shown surrounding nipple 205. FIG. 2H illustrates another example of a substrate including an opening configured to surround a nipple. Substrate 280, a modified toroid structure, is configured for placement on a breast region 210. The opening 285 defined by the modified toroid structure is shown surrounding nipple 205.

In an aspect, the substrate is formed from any of a number of biocompatible materials. Non-limiting examples of biocompatible materials include synthetic polymers (e.g., thermoplastic elastomers, polyvinyl chloride, fluoropolymers, polyurethane, polycarbonate, silicone, acrylic compounds, thermoplastic polyesters, polypropylene, low density polyethylenes, nylon, sulfone resins), natural polymers (e.g., cellulose polymers, collagen, hyalurinc acid, alginates, carrageenan), biocompatible metals (e.g., gold, silver, stainless steel, titanium), or biocompatible ceramics (e.g., porcelain, alumina, hydroxyapatite, zirconia). In an aspect, at least a portion of one or more of the other components of the breast milk supplement delivery device are formed from a biocompatible material. For example, any surface of the breast milk supplement delivery device adapted to come in contact with either the infant's skin or mouth or the lactating female's skin can be formed from a biocompatible material.

The thickness of the substrate is generally about 100-3000 microns. The thickness of the substrate is preferably 500-2000 microns.

In an aspect, the substrate comprises a flexible substrate. In an aspect, the substrate is formed from a flexible material. For example, the substrate may be formed from a flexible material allowing the substrate to substantially conform to the contours of a skin surface, e.g., the skin surface of a mammalian breast. In an aspect, the substrate is formed from a flexible material, e.g., a fabric. In an aspect, the substrate is formed from a woven fabric, non-woven fabric, or a knitted fabric. In an aspect, the fabric is formed from synthetic resin. For example, the substrate may be formed from one or more of viscose rayon, copper ammonia rayon, diacetate, triacetate, promix, nylon, vinylon, vinylidene, polyvinylchloride, polyethylene terephthalate, acrylic resin, polyethylene, polypropylene, polyolein, polyurethane, benzoate, polychlal and the like. In an aspect, the substrate is formed from at least one of polyesters (e.g., polyethylene terephthalate), polyamides (e.g., nylon), polyolefin (e.g., polyethylene or polypropylene), polyvinyl chloride, plasticized polyvinyl chloride, plasticized vinyl acetate-vinyl chloride copolymer, polyvinylidene chloride, ethylene-vinyl acetate copolymer, cellulose acetate, ethylcellulose, ethylene-ethyl acrylate copolymer, polytetrafluoroethylene, polyurethane, ionomer resin, metal foils, and the like.

In some embodiments, the substrate comprises a rigid substrate. In an aspect, the malleable surface of the breast region conforms to the surface of the rigid substrate. In aspect, the rigid substrate includes curvature that allows the rigid substrate to substantially conform to the surface of the breast region of the lactating female. In an aspect, the rigid substrate is formed from a rigid material. For example, the substrate can be formed from a rigid plastic material. For example, the substrate can be formed from a biocompatible metal material, e.g., gold, silver, stainless steel, or titanium. For example, the substrate can be formed from a biocompatible ceramic material, e.g., porcelain, alumina, hydroxyapatite, or zirconia. Non-limiting examples of material for forming a rigid substrate include acrylic, nylon, plastic, ceramic, resin, rubber, epoxy, thermoplastic, photopolymer, polyurethane, silicone, latex. In some embodiments, the substrate is formed from a rigid material but is flexible. For example, the substrate may be formed from a series of articulated segments, each segment formed from rigid material.

Figure 3A:
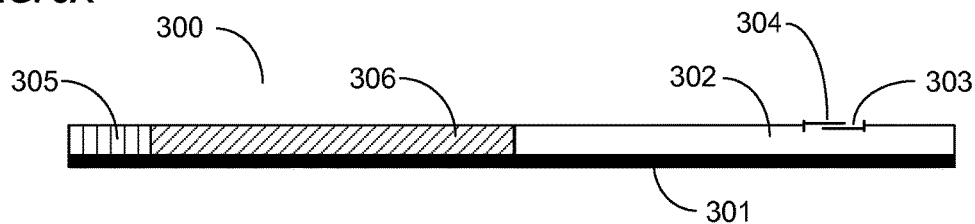
FIG. 3A illustrates a cross-section through an embodiment of a breast milk supplement delivery device.
Figure 3B:
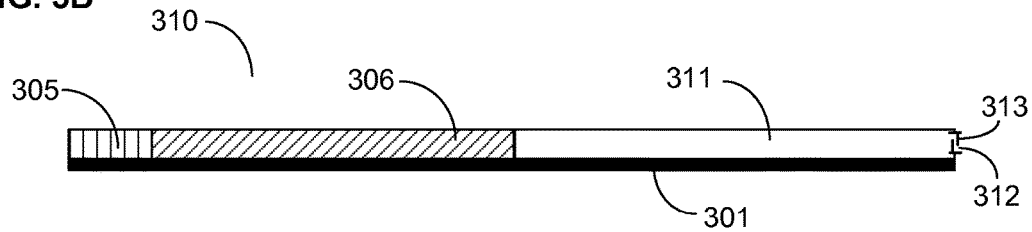
FIG. 3B illustrates a cross-section through an embodiment of a breast milk supplement delivery device.

FIGS. 3A-3F illustrate further aspects of a breast milk supplement delivery device. FIG. 3A shows a longitudinal cross-section through an embodiment of a breast milk supplement delivery device. Breast milk supplement delivery device 300 includes substrate 301 sized for placement on a surface of a breast region of a lactating female. Breast milk supplement delivery device 300 includes a supplement reservoir 302 associated with substrate 301. Supplement reservoir 302 includes at least one pore 303 with a controllable valve 304. Breast milk supplement delivery device 300 includes data storage component 305 including a breast milk supplement regimen. Breast milk supplement delivery device 300 includes control unit 306 including a microprocessor and circuitry, the control unit 306 operably coupled to the data storage component 305 and to the controllable valve 304 of supplement reservoir 302, the circuitry including actuation circuitry configured to actuate the controllable valve 304 of supplement reservoir 302 based on the breast milk supplement regimen. In this non-limiting embodiment, reservoir 302, data storage component 305, and control unit 306 are shown associated with a surface of substrate 301. In an aspect, the pore and controllable valve of the supplement reservoir are incorporated into a top surface of the supplement reservoir, as exemplified in FIG. 3A. In other embodiments, the pore and controllable valve of the supplement reservoir are incorporated into a side surface of the supplement reservoir, a non-limiting example of which is shown in FIG. 3B. FIG. 3B shows a longitudinal cross-section through breast milk supplement delivery device 310. Breast milk supplement delivery device 310 includes substrate 301, data storage component 305, and control unit 306. Breast milk supplement delivery device 310 further includes supplement reservoir 311 in which pore 312 and controllable valve 313 are incorporated into a side surface of supplement reservoir 311.

A breast milk supplement delivery device includes one or more supplement reservoirs. In an aspect, at least one of the one or more supplement reservoirs is adapted to contain one or more breast milk supplements. In an aspect, at least one of the one or more supplement reservoirs is attached to a surface of the substrate. In an aspect, at least one of the one or more supplement reservoirs is detachable from the substrate. In an aspect, the one or more supplement reservoirs comprise a single supplement reservoir having at least one port with a controllable valve. For example, the breast milk supplement delivery device can include a single reservoir having a port with a controllable valve and adapted to contain one or more breast milk supplements, the release of the one or more breast milk supplements through the port controlled by the controllable valve. In an aspect, the one or more supplement reservoirs include multiple small reservoirs, each of the multiple small reservoirs including a port with a controllable valve. For example, the breast milk supplement delivery device can include a series of supplement reservoirs adapted to contain one or more breast milk supplements, each of the series of supplement reservoirs having a controllable mechanism, e.g., a controllable valve, for controlled release of the one or more breast milk supplements. In an aspect, the one or more supplement reservoirs include two or more supplement reservoirs, the two or more supplement reservoirs sharing a common port with a controllable valve. For example, each of the two or more supplement reservoirs may include an outlet, the outlet of each of the two or more supplement reservoirs merging into a common reservoir or flow conduit that includes a common port with a controllable valve.

Figure 3C:
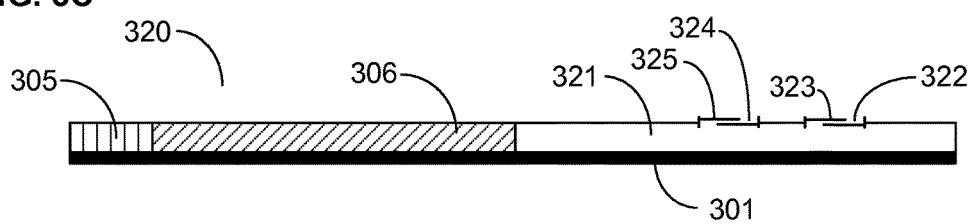
FIG. 3C illustrates a cross-section through an embodiment of a breast milk supplement delivery device.

In some embodiments, the breast milk supplement delivery device includes at least one reservoir with one or more ports, each port including a controllable valve. FIG. 3C illustrates a non-limiting example of a breast milk supplement delivery device including a supplement reservoir with two ports, each of the two ports including a controllable valve. FIG. 3C shows a longitudinal cross-section through breast milk supplement delivery device 320 including substrate 301, data storage component 305, and control unit 306. Breast milk supplement delivery device 320 includes supplement reservoir 321 including a first port 322 with a first controllable valve 323 and a second port 324 with a second controllable valve 325.

Figure 3D:
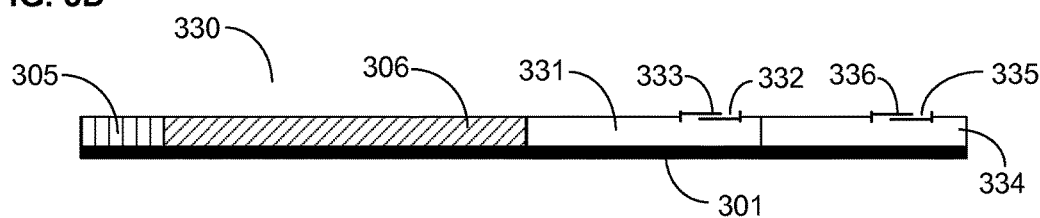
FIG. 3D illustrates a cross-section through an embodiment of a breast milk supplement delivery device.

In some embodiments, the breast milk supplement delivery device includes two or more supplement reservoirs, each of the two or more supplement reservoirs including at least one port with a controllable valve. FIG. 3D shows a longitudinal cross-section through a non-limiting example of a breast milk supplement delivery device including two supplement reservoirs, each of the two supplement reservoirs including a port with a controllable valve. Breast milk supplement delivery device 330 includes substrate 301, data storage component 305, and control unit 306. Breast milk supplement delivery device 330 includes first reservoir 331 having a port 332 with controllable valve 333 and second reservoir 334 having a port 335 with controllable valve 336. In an aspect, first reservoir 331 includes a first set of one or more breast milk supplements and second reservoir 334 includes a second set of one or more breast milk supplements. In an aspect, first reservoir 331 and second reservoir 334 include the same set of one or more breast milk supplements. In an aspect, the actuation circuitry of control unit 306 includes circuitry configured to actuate controllable valve 333 and controllable valve 336 simultaneously. In an aspect, the actuation circuitry of control unit 306 includes circuitry configured to actuate controllable valve 333 and controllable valve 336 independently.

Figure 3E:
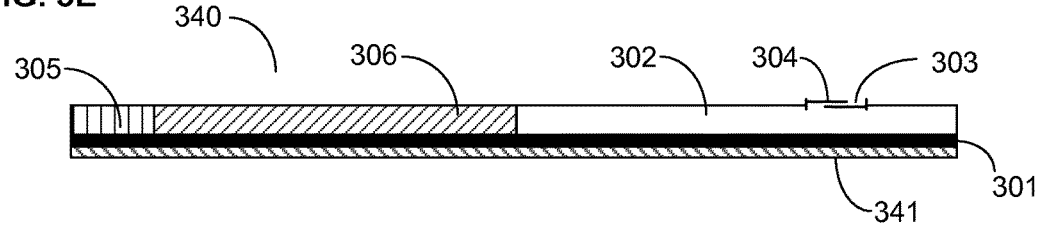
FIG. 3E illustrates a cross-section through an embodiment of a breast milk supplement delivery device.

In some embodiments, a breast milk supplement delivery device includes an adhesive layer configured to adhere the breast milk supplement delivery device to the surface of the breast region of the lactating female. In an aspect, the substrate includes an adhesive on a surface conforming to the surface of the breast region of the lactating female. FIG. 3E illustrates a longitudinal cross-section through an embodiment of a breast milk supplement delivery device including an adhesive layer. Breast milk supplement delivery device 340 includes substrate 301, supplement reservoir 302 having a port 303 with controllable valve 304, data storage component 305, and control unit 306. Breast milk supplement delivery device 340 includes adhesive layer 341 associated with at least a portion of substrate 301.

In an aspect, the breast milk supplement delivery device is configured to adhere to the surface of the breast region of the lactating female. In an aspect, the substrate of the breast milk supplement delivery device is configured to reversibly attach to a skin surface of the breast region. In an aspect, at least one surface of the substrate includes an adhesive. In an aspect, the substrate includes an adhesive on a surface conforming to the surface of the breast region of the lactating female. In an aspect, the adhesive layer includes, but is not limited to, an acrylic adhesive, a natural rubber adhesive, synthetic rubber adhesive, silicone adhesive, vinyl ester adhesive, vinyl ether adhesive, acrylic or vinyl water-containing adhesive and the like conventionally used for medical applications. The thickness of the adhesive layer is generally 5-2000 microns, preferably 10-1000 microns.

In an aspect, the substrate is configured to reversibly attach to the surface of the breast region of the lactating female. In an aspect, at least one surface of the substrate includes a reversible adhesive. In an aspect, the adhesive includes a pressure-sensitive adhesive. In an aspect, the pressure-sensitive adhesive includes a rubber based pressure-sensitive adhesive, an acrylic pressure-sensitive adhesive, a silicone based pressure-sensitive adhesive, or the like. For example, a surface of the substrate intended for placement on the breast region of the lactating female can include a pressure sensitive adhesive. In some embodiments, the reversible adhesive can be one or more pressure sensitive adhesives, e.g., adhesive tape, applicable for skin contact. For example, the breast milk supplement delivery device can be adhered to the surface of the breast region of the lactating female with one or more strips of medical-rated double-stick tape. As another example, the breast milk supplement delivery device can be adhered to the surface of the breast region of the lactating female with a coating of adhesive, e.g., URO-Bond® IV Silicone Skin Adhesive (from, UROCARE Products, Pomona, Calif.). Non-limiting examples of adhesives designed for healthcare use include any of a number of silicone-based pressure sensitive adhesives from, for example, Dow Corning, Midland, Mich. or 3M, St. Paul, Minn.

In some embodiments, the adhesive can be applied to at least a portion of the surface of the breast region of the lactating female prior to placement of the breast milk supplement delivery device on the surface of the breast region. In an embodiment, the adhesive is simply a gel, e.g., a skin lotion or petroleum jelly, which causes the breast milk supplement delivery device to stay in one place on the surface of the breast region.

In an aspect, the adhesive includes a pressure-sensitive adhesive coating on the surface of a thin film. In an aspect, the pressure-sensitive adhesive coating covers at least a portion of at least one surface of the thin film. In an aspect, the one or more thin films are stackable. In an aspect, peeling away a thin film on the top of a stack of thin films reveals an underlying thin film including a pressure-sensitive adhesive coating. For example, the substrate can include a stack of peelable thin films, each thin film including an adhesive (e.g., a pressure-sensitive adhesive coating) on a surface of the thin film intended to be in contact with the breast region of the female subject.

In some embodiments, the breast milk supplement delivery device is immobilized, e.g., adhered, to the breast region of the lactating female for only a short period of time, e.g., during a single nursing event, and then removed. In some embodiments, the breast milk supplement delivery device is adhered to the breast region of the lactating female for a prolonged period of time, e.g., hours, days or weeks.

Figure 3F:
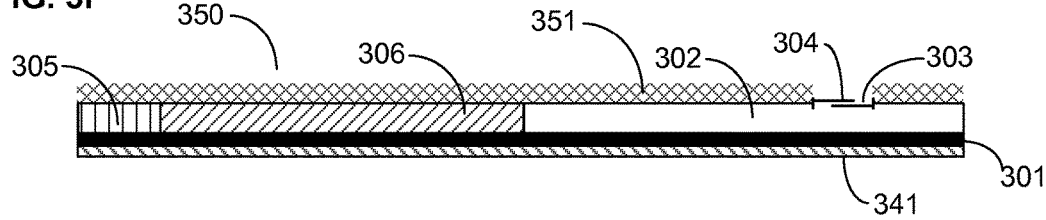
FIG. 3F illustrates a cross-section through an embodiment of a breast milk supplement delivery device.

In some embodiments, a breast milk supplement delivery device includes at least one textured surface. In an aspect, the at least one textured surface is configured for the comfort of the nursing infant and/or the lactating female. In an aspect, the at least one textured surface is associated with at least one of the substrate, the one or more supplement reservoirs, the control unit, and the data storage component. In an aspect, the at least one textured surface forms an outer layer on at least a portion of the breast milk supplement delivery device. FIG. 3F illustrates a longitudinal cross-section through a non-limiting example of a breast milk supplement delivery device including a textured surface. Breast milk supplement delivery device 350 includes substrate 301, supplement reservoir 302 having a port 303 with controllable valve 304, data storage component 305, and control unit 306. Substrate 301 further includes an adhesive 341 on a surface conforming to the surface of the breast region of the lactating female. Breast milk supplement delivery device 350 further includes a textured surface 351 covering at least a portion of supplement reservoir 302, data storage component 305, and/or control unit 306. In some embodiments, textured surface 351 covers that portion of supplement reservoir 302 including port 303. In an aspect, port 303 extends through textured surface 351. For example, the textured surface can include an aperture aligned with the port associated with the supplement reservoir to allow fluid flow out of the supplement reservoir.

In an aspect, the breast milk supplement delivery device includes at least one textured surface. In an aspect, the breast milk supplement delivery device includes a textured surface on at least a portion of at least one surface of the breast milk supplement delivery device. In an aspect, at least a portion of at least one surface of the substrate includes a textured surface. In an aspect, at least a portion of at least one surface the one or more supplement reservoirs, the data storage component, and/or the control unit includes a textured surface. In an aspect, at least a portion of a surface of the breast milk supplement delivery device configured to come in contact with a nursing infant includes a textured surface. In an aspect, the textured surface includes a soft surface. For example, the textured surface can include a soft, comfortable, comfy, fluffy, silky, velvety, cozy, downy, furry, satiny, and/or snug surface. For example, at least a portion of at least one surface of the breast milk supplement delivery device can include a soft material or fabric, e.g., flannel, velvet, satin, fleece, or fur. In an aspect, the textured surface is configured to simulate the surface of a mammalian breast. For example, in the case of a human breast, the textured surface may include a smooth surface formed from a smooth material or fabric. For example, in the case of a non-human breast, the textured surface may include a furry surface formed from real or faux fur.

In some embodiments, the one or more supplement reservoirs of a breast milk supplement delivery device are incorporated into the substrate. In an aspect, the substrate comprises two or more layers. In an aspect, at least one of the one or more supplement reservoirs is disposed between the two or more layers of the substrate. For example, the breast milk delivery device can include a top substrate layer and a bottom substrate layer with at least one supplement reservoir disposed between the top and bottom substrate layers. FIGS. 4A-4E illustrate non-limiting examples of breast milk supplement delivery devices including multiple substrate layers.

Figure 4A:
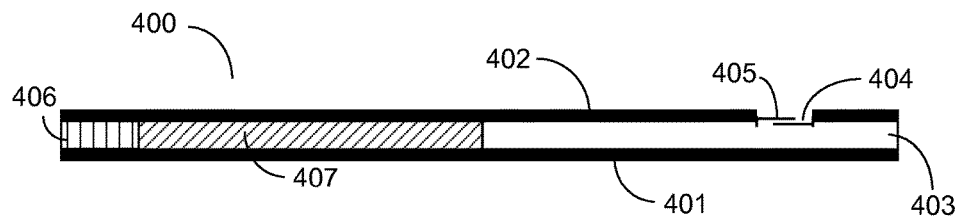
FIG. 4A illustrates a cross-section through an embodiment of a breast milk supplement delivery device.

FIG. 4A illustrates a longitudinal cross-section through a non-limiting example of a breast milk supplement delivery device. Breast milk supplement delivery device 400 includes a bottom substrate layer 401 and a top substrate layer 402. Bottom substrate layer 401 is configured for placement on the surface of the breast region of the lactating female. Disposed between bottom substrate layer 401 and top substrate layer 402 is supplement reservoir 403 having a port 404 extending through top substrate layer 402. Port 404 includes controllable valve 405. Breast milk supplement delivery device 400 includes data storage component 406 disposed between bottom substrate layer 401 and top substrate layer 402. Data storage component 406 includes a breast milk supplement regimen. Breast milk supplement delivery device 400 includes control unit 407 including a microprocessor and circuitry is disposed between bottom substrate layer 401 and top substrate layer 402. Control unit 407 is operably coupled to data storage component 406 and controllable valve 405 of supplement reservoir 403 and includes actuation circuitry configured to actuate the controllable valve 405 of supplement reservoir 403 based on the breast milk supplement regimen.

Figure 4B:
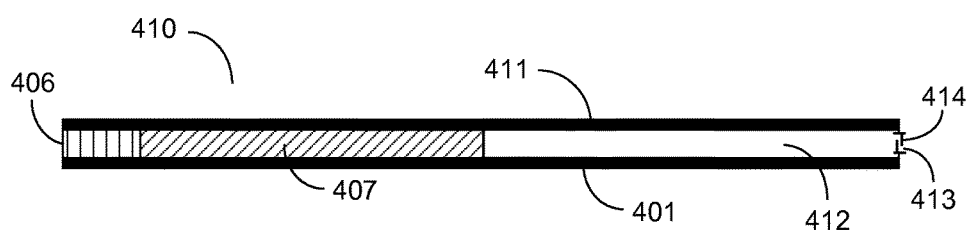
FIG. 4B illustrates a cross-section through an embodiment of a breast milk supplement delivery device.

In some embodiments, the port and controllable valve are positioned on top of the breast milk supplement delivery device, e.g., on top of that portion of the breast milk supplement delivery device not placed on the surface of the breast region of the lactating female. In other embodiments, the port and controllable valve are positioned on a side of the breast milk supplement delivery device, as illustrated in FIG. 4B. FIG. 4B shows a longitudinal cross-section through a non-limiting example of a breast milk supplement delivery device. Breast milk supplement delivery device 410 includes a bottom substrate layer 401 and a top substrate layer 411. Disposed between bottom substrate layer 401 and top substrate layer 411 is supplement reservoir 412 having a port 413 positioned on the side of supplement reservoir 412. Port 413 includes controllable valve 414. Breast milk supplement delivery device 410 includes data storage component 406 and control unit 407. Control unit 407 includes actuation circuitry configured to actuate controllable valve 414.

Figure 4C:
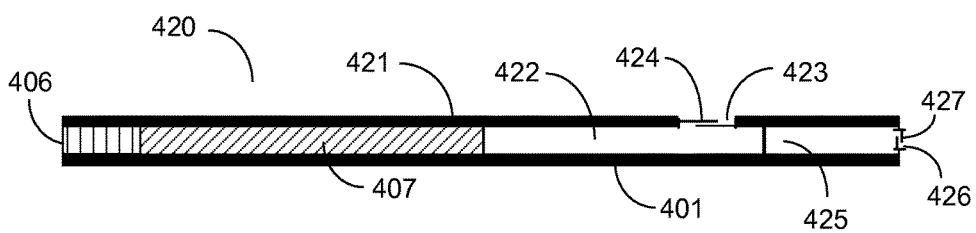
FIG. 4C illustrates a cross-section through an embodiment of a breast milk supplement delivery device.

In some embodiments, the breast milk supplement delivery device includes two or more supplement reservoirs disposed between two or more layers of the substrate. FIG. 4C illustrates a longitudinal cross-section through a non-limiting example of a breast milk supplement delivery device including two supplement reservoirs. Breast milk supplement delivery device 420 includes bottom substrate layer 401 and top substrate layer 421. First supplement reservoir 422 and second supplement reservoir 425 are shown disposed between bottom substrate layer 401 and top substrate layer 421. First supplement reservoir 422 includes port 423 extending through top substrate layer 421. Port 423 includes controllable valve 424. Second supplement reservoir 425 includes port 426 positioned on the side of second supplement reservoir 425. Port 426 includes controllable valve 427. Breast milk supplement delivery device 420 includes data storage component 406 and control unit 407 disposed between bottom substrate layer 401 and top substrate layer 421. Control unit 407 includes actuation circuitry configured to actuate controllable valve 424 and controllable valve 427 based on a breast milk supplement regimen.

Figure 4D:
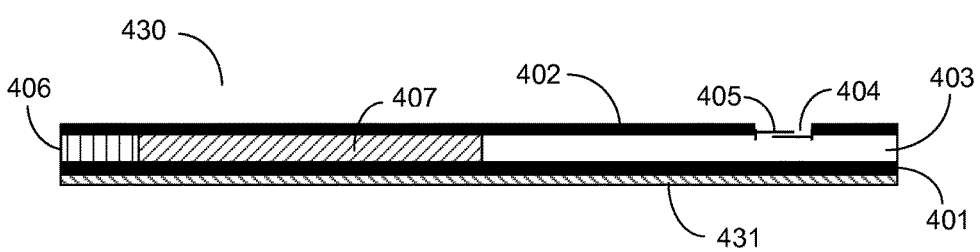
FIG. 4D illustrates a cross-section through an embodiment of a breast milk supplement delivery device.

In some embodiments, a breast milk supplement delivery device including two or more substrate layers includes an adhesive layer. FIG. 4D illustrates a longitudinal cross-section through a non-limiting example of a breast milk supplement delivery device including an adhesive layer. Breast milk supplement delivery device 430 includes bottom substrate layer 401 and top substrate layer 402. Supplement reservoir 403, data storage component 406, and control unit 407 are shown disposed between bottom substrate layer 401 and top substrate layer 402. Supplement reservoir 403 includes port 404 extending out through the top substrate layer 402 and includes controllable valve 405. At least a portion of a surface of bottom substrate layer 401 includes adhesive layer 431. For example, the adhesive layer can include a layer of pressure sensitive adhesive which when pressed onto the surface of the breast region reversibly adheres the breast milk supplement delivery device in place. Non-limiting examples of adhesives have been described above herein.

Figure 4E:
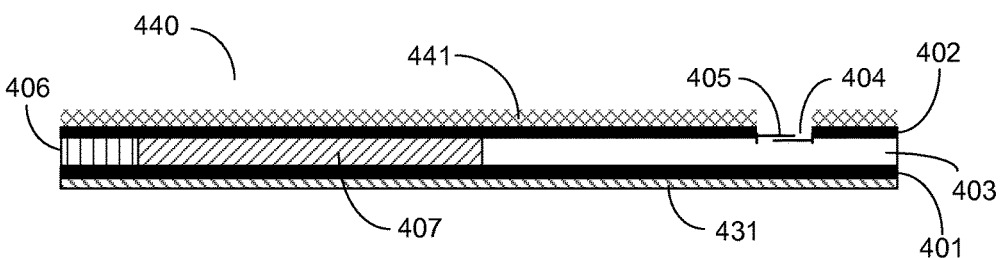
FIG. 4E illustrates a cross-section through an embodiment of a breast milk supplement delivery device.

In some embodiments, a breast milk supplement delivery device including two or more substrate layers includes at least one textured surface. FIG. 4E illustrates a longitudinal cross-section through a non-limiting example of a breast milk supplement delivery device including a textured surface. Breast milk supplement delivery device 440 includes bottom substrate layer 401 and top substrate layer 402. Breast milk supplement delivery device further includes textured surface 441 associated with an outer surface of top substrate layer 402. For example, the breast milk supplement delivery device can include a textured surface that is comfortable and/or comforting to a nursing infant. For example, the breast milk supplement delivery device can include a piece of flannel, faux fur, or other piece of soft fabric attached to a top surface of the breast milk supplement delivery device. Non-limiting examples of materials for a textured surface are described above herein. Supplement reservoir 403, data storage component 406, and control unit 407 are shown disposed between bottom substrate layer 401 and top substrate layer 402. Supplement reservoir 403 includes port 404 extending out through the top substrate layer 402 and textured layer 441 and includes controllable valve 405. Breast milk supplement delivery device 440 further includes adhesive layer 431 associated with bottom substrate layer 401.

Supplements

In an aspect, at least one of the one or more supplement reservoirs is adapted to contain one or more breast milk supplements. For example, the breast milk supplement delivery device can include one or more breast milk supplements stored and controllably released from the one or more supplement reservoirs associated with the breast milk supplement delivery device. In an aspect, the one or more breast milk supplements include a high caloric component intended to boost the weight of an underweight and/or non-thriving infant. In an aspect, at least one of the one or more breast milk supplements comprises a lipid, a protein, an oligosaccharide, a fatty acid, a carbohydrate, or a nucleotide, or any combination thereof. In an aspect, at least one of the one or more breast milk supplements comprises a nutrient, a micronutrient, a vitamin, an amino acid, or a mineral. In an aspect, at least one of the one or more breast milk supplements comprises a therapeutic agent, an antimicrobial agent, a prebiotic, or a probiotic. In an aspect, at least one of the one or more breast milk supplements comprises an appetite stimulator or an appetite suppressant. In an aspect, the one or more breast milk supplements include one or more components of a recommended infant formula composition. See, e.g., Koletzko et al. (2005) "Global Standard for the Composition of Infant Formula: Recommendations of an ESPGHAN Coordinated International Expert Group" *J. Ped. Gastroentrol. Nutr.* 41:584-599, which is incorporated herein by reference.

In an aspect, at least one of the one or more breast milk supplements includes a protein. In an aspect, the protein includes a protein derived from breast milk. In an aspect, the protein is derived from breast milk matched with the species of the lactating female. In an aspect, the protein is derived from human breast milk. In an aspect, the protein is derived from cow's milk. In an aspect, the protein is derived from soy protein extract or other plant-based protein source. In an aspect, the protein includes casein, lactalbumin, bovine serum albumin, immunoglobulin, proteose-peptone, or para-casein. In an aspect, the protein includes protein fractions derived from breast milk, e.g., milk fat globule membrane, acid whey, or rennet whey.

In an aspect, at least one of the one or more breast milk supplements includes a lipid or a fat. In an aspect, the lipid or fat includes linoleic acid, alpha-linoleic acid, lauric acid, myristic acid, and/or trans fatty acids. In an aspect, the lipid or fat includes an n–3 or n–6 fatty acid. In an aspect, the lipid or fat includes omega-3 or omega-6 fatty acids. In an aspect, the lipid or fat includes a long-chain polyunsaturated fatty acid, non-limiting examples of which include docosahexaenoic acid (DHA) and arachidonic acid. In an aspect, the lipid or fat includes a phospholipid, non-limiting examples of which include phosphatidyl choline.

In an aspect, at least one of the one or more breast milk supplements includes a carbohydrate. In an aspect, the carbohydrates includes at least one of glucose, sucrose and/or fructose. In an aspect, the carbohydrate includes a starch.

In an aspect, at least one of the one or more breast milk supplements includes a nucleotide. In an aspect, the nucleotide includes at least one of adenosine, guanosine, or uridine. In an aspect, delivery of the at least one nucleotide is timed with a sleep pattern of the infant. See, e.g., Sanchez et al. (2009) "The possible role of human milk nucleotides as sleep inducers," Nutr. Neurosci. 12:1-8, which is incorporated herein by reference.

In an aspect, at least one of the one or more breast milk supplements comprises one or more nutrients, micronutrients, vitamins, amino acids, or minerals. In an aspect, at least one of the one or more breast milk supplements includes a lipid soluble vitamin, non-limiting examples of which include vitamin A, vitamin D, vitamin E, and vitamin K. In an aspect, at least one of the one or more breast milk supplements includes a water soluble vitamin, non-limiting examples of which include thiamin (vitamin B1), riboflavin (vitamin B2), niacin (vitamin B3), pantothenic acid (vitamin B5), pyridoxine (vitamin B6), cobalamin (vitamin B12), folic acid, L-ascorbic acid (vitamin C), and biotin.

In an aspect, at least one of the one or more breast milk supplements comprises an amino acid. In an aspect, the amino acid includes at least one essential amino acid. In an aspect, the amino acid includes at least one of arginine, cysteine, histidine, isoleucine, leucine, lysine, methionine, phenylalanine, threonine, tryptophan, tyrosine, and/or valine.

In an aspect, at least one of the one or more breast milk supplements includes a mineral or trace element. Non-limiting examples of minerals or trace elements include iron, calcium, phosphorus, magnesium, sodium, potassium, chloride, manganese, fluoride, iodine, selenium, copper, and zinc. In an aspect, at least one of the one or more breast milk supplements includes choline, myo-inositol, L-carnitine, taurine, nucleotides, and/or carrageenan.

In an aspect, at least one of the one or more breast milk supplements comprise a therapeutic agent, an antimicrobial agent, a prebiotic, or a probiotic. In an aspect, at least one of the one or more breast milk supplements includes a therapeutic agent designed to treat a condition of an infant. In an aspect, the therapeutic agent is designed to treat a general condition of an infant, e.g., pain or constipation. For example, the therapeutic agent can include pain relievers (e.g., ibuprofen, acetaminophen, opioids) and stool softeners (e.g., polyethylene glycol, lactulose). In an aspect, the therapeutic agent is designed to treat a specific disease or condition of an infant. For example, the therapeutic agent can include an agent designed to prevent and/or treat a disease or condition of infancy or early childhood (e.g., cerebral palsy, cystic fibrosis, jaundice, spina bifida, hypoglycemia, hypocalcemia, birth defects, and seizure disorders). For example, the therapeutic agent can include an agent designed to prevent and/or treat an infectious disease (e.g., asthma, chicken pox, conjunctivitis, cytomegalovirus infection, congenital toxoplasmosis, congenital syphilis, tuberculosis, sepsis, pneumonia, meningitis, congenital rubella, herpes, diphtheria, influenza, group B streptococcal bacteria, HFMD (hand, foot, and mouth disease), hepatitis, *Haemophilus* influenza, pertussis, and rotavirus).

In an aspect, at least one of the one or more breast milk supplements includes an antimicrobial agent designed to treat a microbial infection, e.g., a bacterial, viral, or fungal infection. In an aspect, the antimicrobial includes an antibiotic, an antiviral, or an antifungal agent. In an aspect, the antimicrobial includes an antiviral agent. In an aspect, the antiviral agent is designed to treat human immunodeficiency virus (HIV), herpes simplex virus, cytomegalovirus, influenza, rotavirus, hepatitis A, hepatitis B, varicella-zoster virus, coxsackievirus, and/or enterovirus. Non-limiting examples of antiviral agents for use in infants include oseltamivir (for influenza), valganciclovir (cytomegalovirus), acyclovir (chickenpox, herpes simplex), AZT (zidovudine), lamivudine, abacavir, lopinavir, nevirapine. For example, the antiviral agent can include AZT plus one or more antiretroviral agents designed to treat HIV. For example, the antiviral agent can include nevirapine for use as a prophylaxis in breastfeeding infants with an HIV seropositive mother. In an aspect, the antimicrobial agent includes an antibiotic. For example, the antibiotic can include ampicillin, gentamicin, cephalosporins, carbanepems, glycopeptides, erythromycin, and/or azithromycin. In an aspect, the antimicrobial agent includes an antifungal agent. For example, the antifungal agent can include a polyene antifungal agent (e.g., amphotericin B), a triazole antifungal agent (e.g., fluconazole, voriconazole), a imidazole antifungal agent (e.g., miconazole, ketoconazole), or an echinocandins antifungal agent (e.g., caspofungin, micafungin, anidulafungin). For example, a antifungal agent can be used to treat thrush associated with *Candida* infection. For example, the antifungal agent amphotericin B can be used to treat invasive *Candida* fungal infection.

In an aspect, at least one of the one or more breast milk supplements includes a prebiotic. In an aspect, the prebiotic includes an agent configured to promote attraction, colonization, and/or growth of one or more probiotic microorganisms. In an aspect, the prebiotic agent promotes growth and/or maintenance of microbes, e.g., bacteria, resident in the gastrointestinal tract of the infant. For example, the prebiotic agent can include dietary fiber (e.g., polysaccharides and oligosaccharides) that promote the growth of at least one type of endogenous microbe, e.g., a probiotic microbe. For example, the prebiotic agent can induce endogenous or administered microbes to generate short chain fatty acids (SCFAs). For example, the prebiotic agent can induce endogenous or administered microbes to excrete an end product inhibitory to pathogenic bacteria. For example, the prebiotic agent can promote a host-mediated attack against tumor sites and/or promote certain strains of *Lactobacillus* that have immune-modulating activity, enhancing phagocyte activity in the blood. See, e.g., U.S. Pat. No. 7,101,565 to Monte titled "Probiotic/Prebiotic Composition and Delivery Method," which is incorporated herein by reference.

In an aspect, the prebiotic agent includes at least one of a mucopolysaccharide, a chitin, a carrageenan, arabinogalactin, a starch polysaccharide, an oligosaccharide, a fructo-oligosaccharide, or inulin. In an aspect, the prebiotic agent includes one or more of an oligosaccharide, a fructo-oligosaccharide (e.g., soy fructo-oligosaccharide, inulin or banana fiber), a pectin or pectic polysaccharide, a mannan (e.g., guar gum, locust bean gum, konjac, or xanthan gum), a pentosan, beta-glucan, arabinan and galactan, such as larch arabinogalactan, and/or mixtures thereof. For example, the prebiotic agent can include a long-chain polysaccharide comprised primarily of fructose monosaccharides (e.g., soy fructo-oligosaccharide, inulin or banana fiber), non-limiting sources of which include honey, beer, onion, asparagus, maple sugar, oats, and Jerusalem artichoke. For example, the prebiotic agent can include pectin and/or pectic polysaccharides including galacturonans or rhamnogalacturonans having various side chains (e.g., D-galactose, L-arabinose, D-xylose, and, less frequently, L-frucose and D-glucuronic acid). For example, the prebiotic agent can include a polysaccharides including neutral pectic polymers such as galactans and arabinans, xyloglucans, and galactomannans. In an aspect, the prebiotic agent includes a form a non-starch polysaccharide, e.g., an arabingalactans. Additional non-limiting examples of prebiotic agents are described in U.S. Pat. No. 7,101,565 to Monte titled "Probiotic/Prebiotic Composition and Delivery Method," which is incorporated herein by reference.

In an aspect, at least one of the one or more breast milk supplements includes a probiotic. In an aspect, the probiotic includes at least one type of microorganism of benefit to the infant. For example, the probiotic can include one or more microorganisms of benefit to the gastrointestinal health of the infant. For example, the probiotic can include one or more microorganisms of benefit to the immunological health of the infant. For example, representatives types of *Lactobacillus* and *Bifidobacterium* significantly influence human health through a range of effects including, but not limited to, detoxification of xenobiotics, biosynthesis of vitamin K, metabolic effects of fermentation of indigestible dietary fiber, positive influence on transit of gastrointestinal contents by peristalsis, competition with pathogenic microbes for nutrients and binding sites on mucosal epithelial cells, and modulation of the host immune response. See, e.g., Hardy et al. (2013) *Nutrients* 5:1869-1912, which is incorporated herein by reference.

In an aspect, the probiotic includes at least one type of *Bifidobacterium*. In an aspect, the at least one type of *Bifidobacterium* includes at least one type of *B. adolescentis*. In an aspect, the at least one type of *Bifidobacterium* includes at least one of *B. laterosporus, B. breve, B. subtilus, B. infantis, B. longum, B. thermophilum, B. animalis,* or *B. bifidum*. In an aspect, the probiotic includes at least one type of *Bacteroides*. In an aspect, the probiotic includes at least one type of *Lactobacillus*. In an aspect, the at least one type of *Lactobacillus* includes at least one of *L. acidophilus*, *L. casei*, *L. fermentum*, *L. salivaroes*, *L. brevis*, *L. leichmannii*, *L. plantarum*, or *L. cellobiosius*. Other non-limiting examples of *Lactobacillus* include *L. reuteri*, *L. curvatus*, *L. bulgaricus*, *L. gasseri*, *L. caveasicus*, *L. helveticus*, *L. lactis*, *L. salivarius*, *L. rhamnosus*, or *L. buchneri*.

Other non-limiting examples of probiotics include *Streptococcus thermphilius*, *Lactococcus lactis cremoris*, *S. diacetylactis* and *S. intermedius*, *L. sporogenes* (also known as *Bacillus coagulans*), *Pediococcus acidilactici* and *Pediococcus pentosaceus*, and *Enterococcus faecium*.

In some embodiments, at least one probiotic is added to a breast milk supplement regimen that includes an antibiotic treatment. For example, the breast milk supplement regimen may include dosing with both an antibiotic, e.g., ampicillin, in combination with a probiotic, e.g., Bifodobacteria and/or Lactobacilli, to prevent disruption of beneficial flora in the infant's gut.

In an aspect, at least one of the one or more breast milk supplements includes an appetite stimulant. In an aspect, the appetite stimulant includes an orexigenic. In an aspect, the appetite stimulant includes a drug, hormone, or other compound that increases appetites. In an aspect, the appetite stimulant includes a naturally occurring neuropeptide, e.g., ghrelin, orexin, or neuropeptide Y. In an aspect, the appetite stimulant includes a receptor antagonist, e.g., a histamine, dopamine, or adrenergic receptor antagonist. In an aspect, the appetite stimulant includes a steroid, e.g., corticosteroids, megestrol acetate, medroxyprogesterone acetate, or anabolic steroids. In an aspect, the appetite stimulant includes an antidiabetic drug, e.g., glibenclamide or chlorpropamide. In an aspect, the appetite stimulant includes pregabalin or insulin. For example, the appetite stimulant can include cyproheptadine. See, e.g., Rodriguez et al. (2014) "Safety and efficacy of cyproheptadine for treating dyspeptic symptoms in children," J. Pediatr. 163:261-267, which is incorporated herein by reference.

In an aspect, at least one of the one or more breast milk supplements includes an appetite suppressant. In an aspect, the appetite suppressant includes an anorectic, anorexigenic, anorexic, or anorexiant compound. In an aspect, the appetite suppressant includes a member of the phenethylamine family, e.g., phentermine.

In an aspect, at least one of the one or more breast milk supplements includes at least one component of a food type associated with an allergic reaction. For example the one or more breast milk supplements can include components of peanuts or tree nuts that are gradually introduced to the nursing infant in low levels to acclimate the infant to potential peanut or tree nut allergens and attenuate or prevent allergic responses when peanuts or tree nuts are introduced into the growing child's diet. Other examples of food types associated with allergic reactions include eggs, cow's milk, fish, shellfish, wheat, and soy.

In an aspect, at least one of the one or more breast milk supplements includes a flavoring. In an aspect, at least one of the one or more breast milk supplements includes a flavoring configured to induce an infant to more readily consume the one or more breast milk supplements. In an aspect, the flavoring includes a flavoring preferred by the infant. In an aspect, the flavoring includes a taste preferred by the infant. In an aspect, the flavoring includes a sweet flavoring. In an aspect, the flavoring includes a salty flavoring.

In an aspect, the flavoring includes an odorant. In an aspect, the flavoring includes components of an aroma preferred by the infant, e.g., an aroma familiar to the baby from either prenatal experience (in utero exposure to amniotic fluid flavored by mother's diet) or postnatal experience (exposure to breast milk flavored by mother's diet). In an aspect, the flavoring is coordinated with a mother's prenatal and/or postnatal diet. For example, an infant may prefer a flavoring similar to an aroma of the amniotic fluid that he or she experienced in utero. For example, an infant may prefer a flavoring similar to a taste and/or aroma associated with a mother's breast milk. See, e.g. Venture & Worobey (2013) "Early Influences on the Development of Food Preferences," Current Biology 23:R401-R408, which is incorporated herein by reference.

In an aspect, the flavoring comprises a flavoring associated with a specific food type, the flavoring intended to acclimate the infant to the specific food type. For example, the flavoring can include flavors associated with vegetables, e.g., broccoli or carrots. For example, the flavoring can include flavors associated with a specific ethnic diet, e.g., the ethnic diet of the infant's family or culture. For example, the flavoring can be used to acclimate the infant to a specific food type prior to introducing the infant to said food type. For example, the infant can be exposed to a flavoring associated with a vegetable prior to introducing the vegetable to the infant, with the goal of increasing the likelihood that the infant will have a favorable response to the vegetable. For example, the infant can be exposed to a flavoring associated with a type of ethnic cooking prior to introducing the cooking style to the infant, with the goal of increasing the likelihood that the infant will have a favorable response to the ethnic cooking.

In an aspect, the flavoring includes a spice. In an aspect, the spice is associated with a food or cooking style. In an aspect, the spice is associated with an ethnic food or ethnic cooking style. In an aspect, the spice is associated with or preferred by the lactating female and/or her community or the community in which the infant will be raised. In an aspect, the spice is derived from a seed, a fruit, a root, a bark, or a vegetable substance. Non-limiting examples of spices include absinthe, ajwain, akudjura, alexanders, alkanet, alligator pepper, allspice, angelica, anise, annatto, apple mint, artemisia, asafetida, asarabacca, avens, avocado leaf, barberry, basil, bay leaf, bee balm, boldo, borage, caraway, cardamom, catnip, cassia, cayenne, celery seed, chervil, chicory, chili pepper, chives, cicely, cilantro, cinnamon, clary, clove, coriander, costmary, cubeb pepper, cudweed, cumin, curry, dill, elderflower, epazote, fennel, fenugreek, file powder, fingerroot, galangal, galingale, garlic, ginger, golpar, grains of paradise, grains of selim, horseradish, huacatay, hyssop, jasmine, jimbu, juniper berry, kaffir lime, kawakawa, kencur, keluak, kinh gioi, kokam, korarima, koseret, lavender, lemon balm, lemongrass, lemon ironbark, lemon myrtle, lemon verbena, leptotes bicolor, calamint, licorice, lime flower, lovage, mace, mahlab, marjoram, mastic, mint, horopito, musk mallow, mustard, nigella, njangsa, nutmeg, olida, oregano, orris root, pandan, paprika, paracress, parsley, pepper, peppermint, perilla, quassia, rosemary, rue, safflower, saffron, sage, salad burnet, salep, sassafras, savory, silphium, shiso, sorrel, spearmint, spikenard, sumac, sweet woodruff, tarragon, thyme, turmeric, vanilla, voatsiperifery, wasabi, watercress, wattleseed, willow herb, wintergreen, wood avens, woodruff, wormwood, za'atar, zedoary.

In an aspect, the flavoring can include a mixture of spices. In an aspect, the mixture of spices includes advieh or adwiya (Persian cuisine), baharat (Ethiopia, Eritrea), bumbu (Indonesia), chaat masala (India, Pakistan), chili powder, curry powder, five-spice powder, garam masala (South Asia), harissa (North Africa), Hawaij (Yemen), jerk spice (Jamaica), Khmeli suneli (Georgia, former USSR), masala, panch phoron (India, Bangladesh), quatre epices (France), ras el hanout (North Africa), shichimi togarashi (Japan), vegeta (Croatia), and/or za'atar (Middle East).

Valves

In an aspect, a breast milk supplement delivery device includes one or more supplement reservoirs, at least one of the one or more supplement reservoirs having a port with a controllable valve. In an aspect, a breast milk supplement delivery device includes two or more supplement reservoirs having a common port with a controllable valve. In an aspect, a breast milk supplement delivery device includes one or more supplement reservoirs, each of the one or more reservoirs having at least one port including a controllable valve. In an aspect, the port includes an opening defined by the walls of the reservoir. In an aspect, the controllable valve is configured to at least partially open and close in response to an actuation signal. In an aspect, the controllable valve is responsive to an actuation signal transmitted by or from the actuation circuitry. In an aspect, the actuation circuitry includes circuitry configured to at least partially open or close the controllable valve. In an aspect, the actuation circuitry includes circuitry configured to at least one of open the controllable valve, close the controllable valve, change a pressure threshold of the controllable valve, increase an opening size of the controllable valve, decrease an opening size of the controllable valve, or alter a permeability or porosity of the controllable valve.

In an aspect, the controllable valve is formed from an electroactive polymer. For example, the controllable valve can include a metal portion, e.g., platinum, and a thin film of electroactive polymer, e.g., Parylene, which when energized melts to open the valve. See, e.g., Li et al. (2010) "A low power, on demand electrothermal valve for wireless drug delivery applications," Lab Chip 10:101-110, which is incorporated herein by reference.

In an aspect, the controllable valve is formed from a stimulus responsive hydrogel. In an aspect, the controllable valve is formed from a hydrogel material that swells and/or shrinks in response to a stimulus, e.g., light, pH, temperature, electric field, magnetic field, chemical analytes and/or biological components. For example, the controllable valve can be formed from any of a number of stimulus responsive hydrogels, non-limiting examples of which include poly(2-hydroxyethyl methacrylate) co-acrylic acid, poly methacrylic acid-triethylene glycol dimethacrylate, and poly(N-isopropylacrylamide). Non-limiting examples of valves formed from stimulus responsive hydrogels are described in Argentiere et al. (2012) "Smart Microfluidics: The role of stimuli-responsive polymers in microfluidic devices," Advances in Microfluidics, R. Kelly (Ed.), ISBN:978-953-51-0106-2, InTech; Ionov (2014) "Hydrogel-based actuators" possibilities and limitations," Materials Today 17:494-503; and Qui & Park (2001) "Environment-sensitive hydrogels for drug delivery," Adv Drug Delivery Rev 53:321-339, which are incorporated herein by reference.

In an aspect, the controllable valve is formed from a shape-memory alloy. For example, the controllable valve can include a nickel-titanium alloy responsive to a thermal stimulus. See, Fu et al. (2004) "TiNi-based thin films in MEMS applications: a review," Sensors and Actuators A 112:395-408, which is incorporated herein by reference. In an aspect, the controllable valve includes a shape memory alloy responsive to a magnetic field. See, e.g., Flaga et al. (2011) "Pneumatic valves based on magnetic shape memory alloys: Potential applications." 2011 $12^{th}$ International Carpathian Control Conference (ICCC; January 2011; DOI: 10.1109/CarpathianCC.2011. 5945827), which is incorporated herein by reference.

In an aspect, the controllable valve includes a piezoelectric valve. In an aspect, the piezoelectric valve can include a ceramic material which undergoes a mechanical deformation, e.g., a bending moment, in response to an applied voltage. For example, the controllable valve can include a piezoelectric ceramic material, e.g., barium-titanate or lead-zirconate-titanate, that covers the pore of the supplement reservoir and is reversibly bent away from the pore in response to an applied voltage. See, e.g., U.S. Pat. No. 7,569,051 to Shachar titled "Apparatus for piezoelectric layer-wise pump and valve for use in local administration of biological response modifiers and therapeutic agents," which is incorporated herein by reference.

In an aspect, at least one of the one or more supplement reservoirs of the breast milk supplement delivery device includes a port. In an aspect, the port comprises an opening. In an aspect, the port comprises an opening defined by a wall of the at least one supplement reservoir. The port is in fluid communication with a space outside the interior of the one or more supplement reservoirs. In an aspect, the port is in fluid communication with an absorbent layer. For example, the controllable valve of the port can control flow of fluid from a supplement reservoir, through the port, and into an absorbent layer associated with an exterior portion of the breast milk supplement delivery device.

Figure 5A:
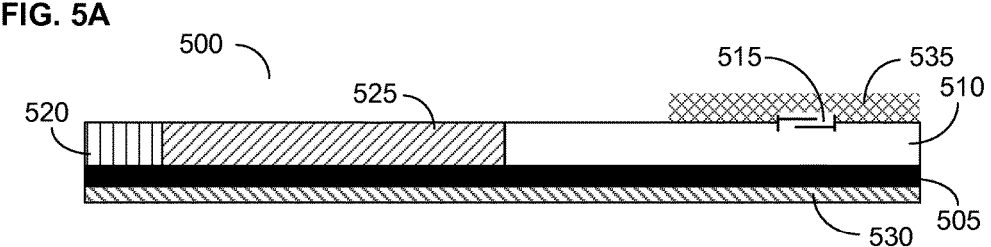
FIG. 5A illustrates a cross-section through an embodiment of a breast milk supplement delivery device with an absorbent layer.
Figure 5B:
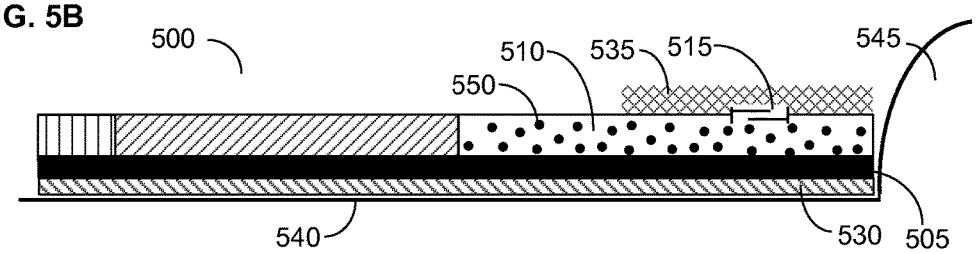
FIG. 5B illustrates a cross-section through an embodiment of a breast milk supplement delivery device such as shown in FIG. 5A and including a breast milk supplement.
Figure 5C:
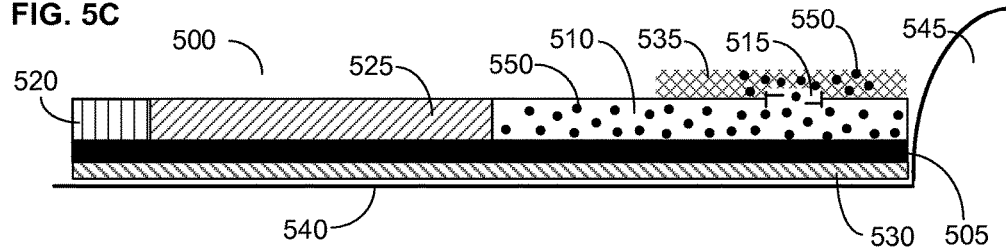
FIG. 5C illustrates a cross-section through an embodiment of a breast milk supplement delivery device such as shown in FIG. 5B and including releasing the breast milk supplement into the absorbent layer.

In an aspect, the absorbent layer covers at least a portion of the one or more supplement reservoirs. FIGS. 5A-5C illustrate aspects of an embodiment of a breast milk supplement delivery device including an absorbent layer covering at least a portion of a reservoir. FIG. 5A shows a longitudinal cross-section through an embodiment of a breast milk supplement delivery device. Breast milk supplement delivery device 500 includes substrate 505 sized for placement on a surface of a breast region of a lactating female. Breast milk supplement delivery device 500 includes supplement reservoir 510 associated with substrate 505, supplement reservoir 510 including a port with a controllable valve 515. Supplement reservoir 510 is adapted to contain one or more breast milk supplements. Breast milk supplement delivery device 500 includes data storage component 520 including a breast milk supplement regimen. Breast milk supplement delivery device 500 includes control unit 525 including a microprocessor and circuitry. Control unit 525 includes actuation circuitry configured to actuate the controllable valve 515 of supplement reservoir 510 based on the breast milk supplement regimen. Breast milk supplement delivery device 500 includes adhesive layer 530 associated with substrate 505. Breast milk supplement delivery device 500 further includes absorbent layer 535 positioned over supplement reservoir 510.

FIG. 5B shows a longitudinal cross-section through breast milk supplement delivery device 500 placed on a surface of a breast region of a lactating female. Substrate 505 of breast milk supplement delivery device 500 is shown adhered through adhesive layer 530 on the skin surface 540 of a breast region. At least one edge of breast milk supplement delivery device 500 is shown in close proximity to nipple 545. Supplement reservoir 510 contains one or more breast milk supplements 550. Controllable valve 515 of supplement reservoir 510 is shown in a closed position. Breast milk supplement delivery device 500 further includes absorbent layer 535 positioned over supplement reservoir 510.

FIG. 5C shows a longitudinal cross-section through breast milk supplement delivery device 500 placed on a surface of a breast region of a lactating female. Substrate 505 of breast milk supplement delivery device 500 is shown adhered through adhesive layer 530 on the skin surface 540 of a breast region. At least one edge of breast milk supplement delivery device 500 including absorbent layer 535 is shown in close proximity to nipple 545. Supplement reservoir 510 contains one or more breast milk supplements 550. Controllable valve 515 of supplement reservoir 510 is shown in an open position in response to an actuation signal from control unit 525. Actuation of controllable valve 515, i.e., at least partially opening and/or closing the controllable valve, is based on the breast milk supplement regimen stored in data storage component 520. The one or more breast milk supplements 550 are shown flowing out of supplement reservoir 510 and soaking into absorbent layer 535.

Figure 6A:
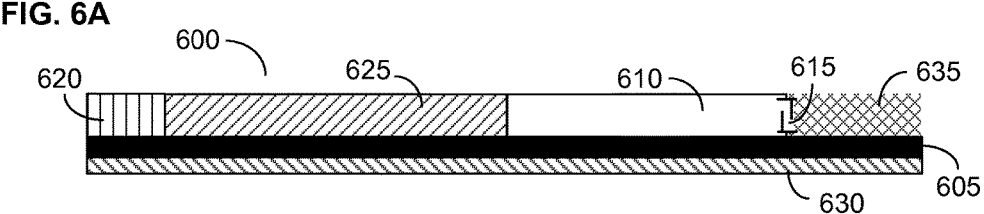
FIG. 6A illustrates a cross-section through an embodiment of a breast milk supplement delivery device with an absorbent layer.
Figure 6B:
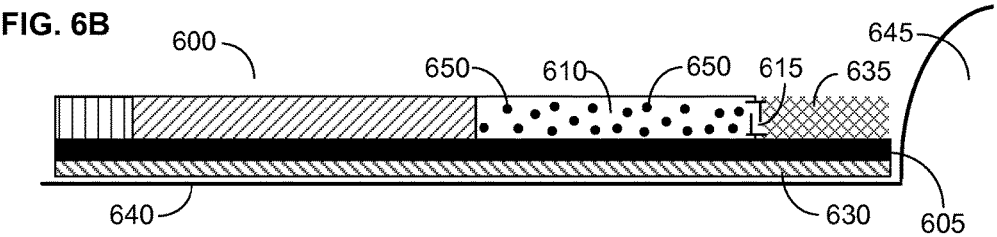
FIG. 6B illustrates a cross-section through an embodiment of a breast milk supplement delivery device such as shown in FIG. 6A and including a breast milk supplement.
Figure 6C:
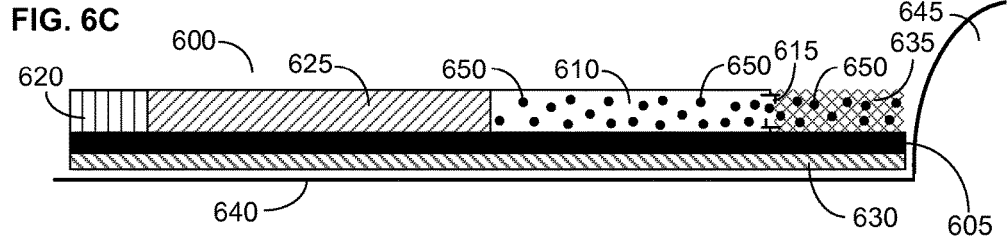
FIG. 6C illustrates a cross-section through an embodiment of a breast milk supplement delivery device such as shown in FIG. 6B and including releasing the breast milk supplement into the absorbent layer.

In an aspect, the absorbent layer comprises an outer layer on a surface of the substrate. FIGS. 6A-6C illustrate aspects of an embodiment of a breast milk supplement delivery device including an absorbent layer that comprises an outer layer on a surface of the substrate. FIG. 6A shows a longitudinal cross-section through an embodiment of a breast milk supplement delivery device. Breast milk supplement delivery device 600 includes substrate 605 sized for placement on a surface of a breast region of a lactating female. Breast milk supplement delivery device 600 includes supplement reservoir 610 associated with substrate 605, supplement reservoir 610 including a port with a controllable valve 615. In this non-limiting example, the port with the controllable valve is positioned on the side of the supplement reservoir. Supplement reservoir 610 is adapted to contain one or more breast milk supplements. Breast milk supplement delivery device 600 includes data storage component 620 including a breast milk supplement regimen. Breast milk supplement delivery device 600 includes control unit 625 including a microprocessor and circuitry. Control unit 625 includes actuation circuitry configured to actuate the controllable valve 615 of supplement reservoir 610 based on the breast milk supplement regimen. Breast milk supplement delivery device 600 includes adhesive layer 630 associated with substrate 605. Breast milk supplement delivery device 600 further includes absorbent layer 635 forming an outer layer on a surface of substrate 605 and positioned proximal to controllable valve 615.

FIG. 6B shows a longitudinal cross-section through breast milk supplement delivery device 600 placed on a surface of a breast region of a lactating female. Substrate 605 of breast milk supplement delivery device 600 is shown adhered through adhesive layer 630 on the skin surface 640 of a breast region. At least one edge of breast milk supplement delivery device 600 including absorbent layer 635 is shown in close proximity to nipple 645. Supplement reservoir 610 contains one or more breast milk supplements 650. Controllable valve 615 of supplement reservoir 610 is shown in a closed position.

FIG. 6C shows a longitudinal cross-section through breast milk supplement delivery device 600 placed on a surface of a breast region of a lactating female. Substrate 605 of breast milk supplement delivery device 600 is shown adhered through adhesive layer 630 on the skin surface 640 of a breast region. At least one edge of breast milk supplement delivery device 600 is shown in close proximity to nipple 645. Supplement reservoir 610 contains one or more breast milk supplements 650. Controllable valve 615 of supplement reservoir 610 is shown in an open position in response to an actuation signal from control unit 625. Actuation of controllable valve 615, i.e., at least partially opening and/or closing the controllable valve, is based on the breast milk supplement regimen stored in data storage component 620. The one or more breast milk supplements 650 are shown flowing out of supplement reservoir 610 and soaking into absorbent layer 635.

Figure 7A:
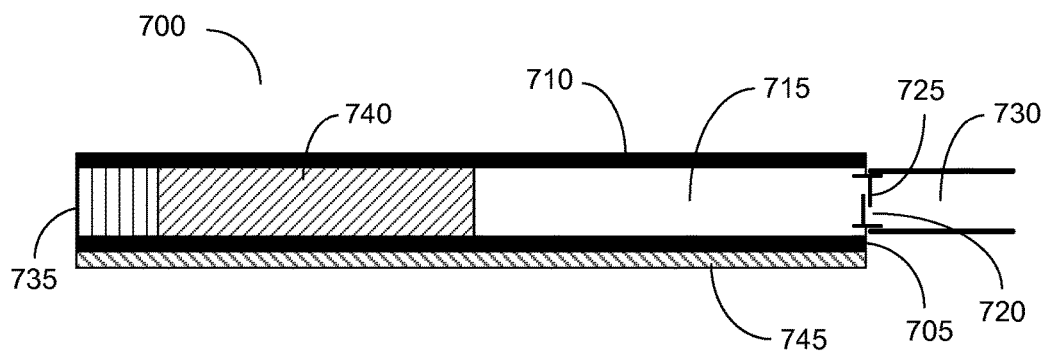
FIG. 7A illustrates a cross-section through an embodiment of a breast milk supplement delivery device a flow conduit.
Figure 7B:
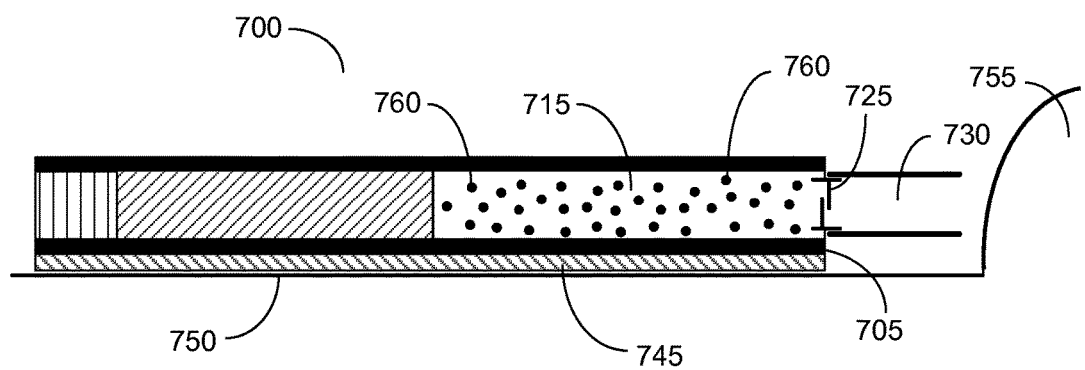
FIG. 7B illustrates a cross-section through an embodiment of a breast milk supplement delivery device such as shown in FIG. 7A and including a breast milk supplement.
Figure 7C:
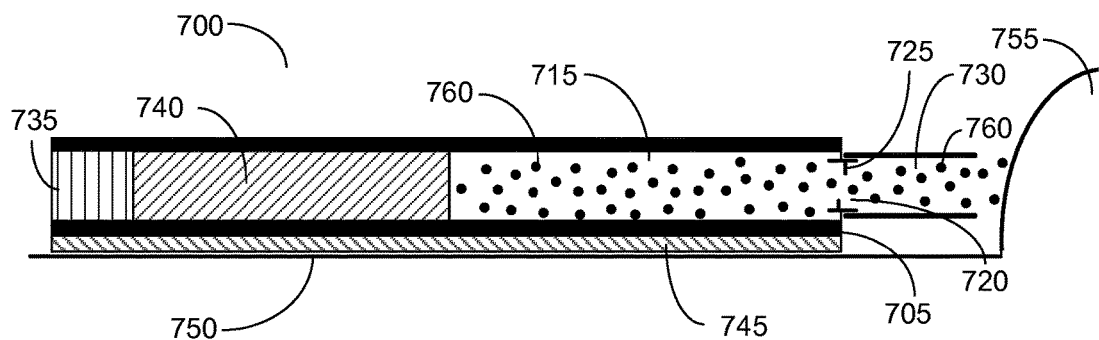
FIG. 7C illustrates a cross-section through an embodiment of a breast milk supplement delivery device such as shown in FIG. 7B and including releasing the breast milk supplement through the flow conduit.

In some embodiments, a breast milk supplement delivery device includes a port in fluid communication with at least one flow conduit, the at least one flow conduit including a first end attached to the port and a second end configured for positioning proximal to a nipple of the lactating female. FIGS. 7A-7C illustrate aspects of a breast milk supplement delivery device including a flow conduit. FIG. 7A Figure shows a longitudinal cross-section through an embodiment of a breast milk supplement delivery device. Breast milk supplement delivery device 700 includes bottom substrate 705 sized for placement on a surface of a breast region of a lactating female and top substrate 710. Breast milk supplement delivery device 700 includes supplement reservoir 715 disposed between bottom substrate 705 and top substrate 710, supplement reservoir 715 including port 720 with controllable valve 725. In this non-limiting example, the port with a controllable valve is positioned on the side of the supplement reservoir. Supplement reservoir 715 is adapted to contain one or more breast milk supplements. Port 720 is shown in fluid communication with flow conduit 730. In an aspect, flow conduit 730 includes a piece of tubing or a capillary. In some embodiments, the flow conduit can include an open flow conduit, e.g., a trough, an open channel, drain, a wick, or culvert formed in a portion of the breast milk supplement delivery device. For example, the flow conduit can include an open channel cut into a surface of the substrate. Breast milk supplement delivery device 700 includes data storage component 735 including a breast milk supplement regimen. Breast milk supplement delivery device 700 includes control unit 740 including a microprocessor and circuitry. Control unit 740 includes actuation circuitry configured to actuate the controllable valve 725 of supplement reservoir 715 based on the breast milk supplement regimen. Breast milk supplement delivery device 700 includes adhesive layer 745 associated with bottom substrate 705.

FIG. 7B shows a longitudinal cross-section through breast milk supplement delivery device 700 placed on a surface of a breast region of a lactating female. Bottom substrate 705 of breast milk supplement delivery device 700 is shown adhered through adhesive layer 745 on the skin surface 750 of a breast region. The second end of flow conduit 730 is shown in close proximity to nipple 755. Supplement reservoir 715 contains one or more breast milk supplements 760. Controllable valve 725 of supplement reservoir 715 is shown in a closed position.

FIG. 7C shows a longitudinal cross-section through breast milk supplement delivery device 700 placed on a surface of a breast region of a lactating female. The bottom substrate 705 of breast milk supplement delivery device 700 is shown adhered through adhesive layer 745 to the skin surface 750 of a breast region. The second end of flow conduit 730 is shown in close proximity to nipple 755. Supplement reservoir 715 contains one or more breast milk supplements 760. Controllable valve 725 of supplement reservoir 715 is shown in an open position in response to an actuation signal from control unit 740. Actuation of controllable valve 725, i.e., at least partially opening and/or closing the controllable valve, is based on the breast milk supplement regimen stored in data storage component 735. The one or more breast milk supplements 760 are shown flowing out of supplement reservoir 715, through port 720 and flow conduit 730, and into close proximity with nipple 755.

Data Storage Component

A breast milk supplement delivery device includes a data storage component including a breast milk supplement regimen. The data storage component includes stored information associated with a breast milk supplement regimen. The data storage component is operably coupled to the control unit of the breast milk supplement delivery device. In an aspect, the data storage component is incorporated into the control unit of the breast milk supplement delivery device. In an aspect, the data storage component includes a removable data storage component. In an aspect, the data storage component includes a non-volatile data storage component. In an aspect, the data storage component includes a recordable data storage component. In an aspect, the data storage component includes a mass storage device. In an aspect, the data storage component is operably coupled to a central processing unit of the control unit through input/output channels. In an aspect, the data storage component includes data storage media. In an aspect, the data storage component is included in a hard drive of the control unit. In an aspect, the data storage component is removable. In an aspect, the data storage component includes a removable memory card. In an aspect, the data storage component includes a removable memory stick.

In an aspect, the data storage component is incorporated into the control unit of the breast milk supplement delivery device. In an aspect, the data storage component includes memory chips, e.g., ROM or flash memory chips, for providing storage of operating systems, look-up tables, and database information regarding at least one breast milk supplement regimen. The system memory of the control unit and/or computing component may include read-only memory (ROM) and random access memory (RAM). A number of program modules may be stored in the ROM or RAM, including an operating system, one or more application programs, other program modules and program data.

In an aspect, the data storage component is wirelessly updateable. For example, a data storage component may have access to data wirelessly transmitted to the breast milk supplement delivery device, e.g., through a Bluetooth or other wireless transmission means. For example, the data storage component can receive updates to the breast milk supplement regimen from a wireless transmission from a remote source, e.g., an Internet site, another computing device, a personal electronic device, and the like.

In an aspect, the data storage component includes a removable data storage device. For example, the data storage component can include a removable card, stick, or flash drive. Non-limiting examples of removable data storage devices include flash memory cards, Memory Sticks, mass storage devices, CompactFlash, non-volatile memory cards, Secure Digital™ (SD) cards, miniSD cards, microSD cards, USB flash drive, or XQD cards.

The data storage component is configured to store a breast milk supplement regimen. The breast milk supplement regimen includes at least one dosing regimen for one or more breast milk supplements. In an aspect, the breast milk supplement regimen includes a systematic or regulated plan for delivery of one or more breast milk supplements to a nursing infant. In an aspect, the breast milk supplement regimen includes one or more types of breast milk supplements and dosing and timing of said breast milk supplements. In an aspect, the data storage component is configured to store two or more breast milk supplement regimens. For example, the data storage component can be configured to store a breast milk supplement regimen for each of two or more infants nursing from the same lactating female.

In an aspect, the breast milk supplement regimen includes a personalized breast milk supplement regimen. For example, the breast milk supplement regimen can be personalized for a specific subject. For example, the breast milk supplement regimen can be personalized for a subset of subjects with common nutritional and/or medical need.

In an aspect, the breast milk supplement regimen is personalized for an infant. For example, the breast milk supplement regimen can be personalized for a specific infant based on the nutritional and/or medical need of the specific infant. In an aspect, the breast milk supplement regimen is personalized based on attributes of an infant. In an aspect, the breast milk supplement regimen is personalized based on at least one of age, weight, genome, gender, ethnicity, medical condition, or nutritional need of the infant. For example, the breast milk supplement regimen can be personalized based on age of the infant, wherein younger infants (less than 6 months in age) require more calories per pound of body weight per day than older infants (one year or older). For example, the amounts of each of the one or more breast milk supplements in the breast milk supplement regimen can be personalized based on the weight of the infant, e.g., milligrams or grams of supplement per kilogram of infant body weight. For example, the breast milk supplement regimen can be personalized for a premature infant. For example, the breast milk supplement regimen can be personalized for an underweight infant failing to thrive. For example, the breast milk supplement regimen can be personalized to supplement a mineral or micronutrient deficiency of the infant. For example, the breast milk supplement regimen can be personalized to provide iron supplementation on a daily basis according to infant body weight (e.g., 2-3 mg/kg of body weight/day over a 3 month period to increase iron and treat anemia). For example, the breast milk supplement regimen can be personalized to provide iodine supplementation on a daily basis (e.g., 60-90 ug/day). For example, the breast milk supplement regimen can be personalized to provide zinc supplementation, particularly in infant experiencing diarrhea (e.g., 10 mg per day for 10-14 days). For example, the breast milk supplement regimen can be personalized to include one or more antimicrobial agents (e.g., antiretroviral agents) to take into account a medical condition, e.g., a viral infection, of an infant. For example, the breast milk supplement regimen can be personalized to include one or more flavorings of a food type associated with the ethnicity of an infant.

In an aspect, the breast milk supplement regimen is personalized for the lactating female. In an aspect, the breast milk supplement regimen is personalized based on a quality of breast milk of the lactating female. In an aspect, the breast milk supplement regimen is personalized based on a nutritional quality of the breast milk of the lactating female. For example, the breast milk supplement regimen can include one or more breast milk supplements, e.g., micronutrients or minerals, deficient in the breast milk of the lactating female. For example, the breast milk supplement regimen can be personalized to include one or more vitamins lacking or deficient in breast milk, e.g., vitamin D (recommended 400 international units per day) and/or vitamin K (recommended 25 micrograms per day; see, e.g., Committee on Fetus and Newborn (2003) "Controversies concerning vitamin K and the newborn. American Academy of Pediatrics" Pediatrics 112:191-192 which is incorporated herein by reference). For example, the breast milk supplement regimen can include added n-6 and n-3 fatty acids, e.g., linoleic acid, arachidonic acid, and/or DHA, potentially deficient in the breast milk of a lactating female with a specific diet, e.g., a low fat, vegetarian, or vegan diet. See, e.g., Innis (2007) "Human milk: maternal dietary lipids and infant development," Proc. Nutr. Soc. 66:397-404, which is incorporated herein by reference. In an aspect, the breast milk supplement regimen is personalized based on a microbial quality of the breast milk of the lactating female. For example, the breast milk supplement regimen may be designed to add microbes, e.g., probiotics such as *bifidobacterium*, that might be underrepresented in the breast milk of the lactating female. See, e.g., Hunt et al (2011) "Characterization of the diversity and temporal stability of bacterial communities in human milk," PLoS ONE 6(6):e21313, which is incorporated herein by reference. For example, the breast milk supplement regimen may be designed to add microbes, e.g., microbes of Leuconostocaceae and/or Staphylococcaceae bacterial families, that are underrepresented in breast milk from a lactating female choosing elective cesarean section versus vaginal or non-elective cesarean section. See, e.g., Cabrera-Rubio et al. (2012) "The human milk microbiome changes over lactation and is shaped by maternal weight and mode of delivery," Am. J. Clin. Nutr. 96:544-551, which is incorporated herein by reference. In an aspect, the breast milk supplement regimen is personalized based on an immunological quality of the breast milk of the lactating female. For example, the breast milk supplement regimen may include added immunoglobulin A in a lactating female with an immunoglobulin A deficiency. Reduced immunoglobulin A in colostrum and breast milk of the lactating female may predispose an infant to develop food allergies. See, e.g., Jarvinen et al. (2000) "Does low IgA in human milk predispose the infant to development of cow's milk allergy?" Pediatr. Res. 48:457-462, which is incorporated herein by reference.

In an aspect, the breast milk supplement regimen is adjustable. In an aspect, the breast milk supplement regimen is adjustable based on a change in at least one of an attribute of an infant and a quality of breast milk of the lactating female. For example, the infant's nutritional needs may change as the infant ages and/or gains weight. For example, the quality of the breast milk of the lactating female may change in response to changing the female's diet or treating a medical condition.

Control Unit

A breast milk supplement delivery device includes a control unit including a microprocessor and circuitry. In an aspect, the control unit includes a microprocessor, e.g., a central processing unit, for controlling one or more functions of the breast milk supplement delivery device. In an aspect, the microprocessor is incorporated into one or more integrated circuits. In an aspect, the microprocessor is programmable, capable of accepting input data, processes the input data according to instructions, and provides results as output. The control unit further includes a system memory and a system bus that couples various system components including the system memory to the microprocessor. The microprocessor can include a processing unit, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an aspect, the control unit includes one or more ASICs having a plurality of pre-defined logic components. In an aspect, the control unit includes one or more FPGA having a plurality of programmable logic commands. In an aspect, the control unit includes embedded software.

The control unit includes circuitry. In an aspect, the circuitry includes actuation circuitry configured to actuate the controllable valve of the at least one of the one or more supplement reservoirs based on the breast milk supplement regimen. In an aspect, the actuation circuitry is operably coupled to an actuator associated with the controllable valve. For example, the actuation circuitry can be operably coupled to at least one of a pneumatic actuator, a hydraulic actuator, a magnetic actuator, or an electric actuator. In an aspect, the actuation circuitry is configured to at least partially open or close the controllable valve. In an aspect, the actuation circuitry is configured to at least one of open the controllable valve, close the controllable valve, change a pressure threshold of the controllable valve, increase an opening size of the controllable valve, decrease an opening size of the controllable valve, or alter a permeability or porosity of the controllable valve. In an aspect, the circuitry includes one or more instructions for operating the breast milk supplement delivery device.

Delivery Event Sensor

Figure 8:
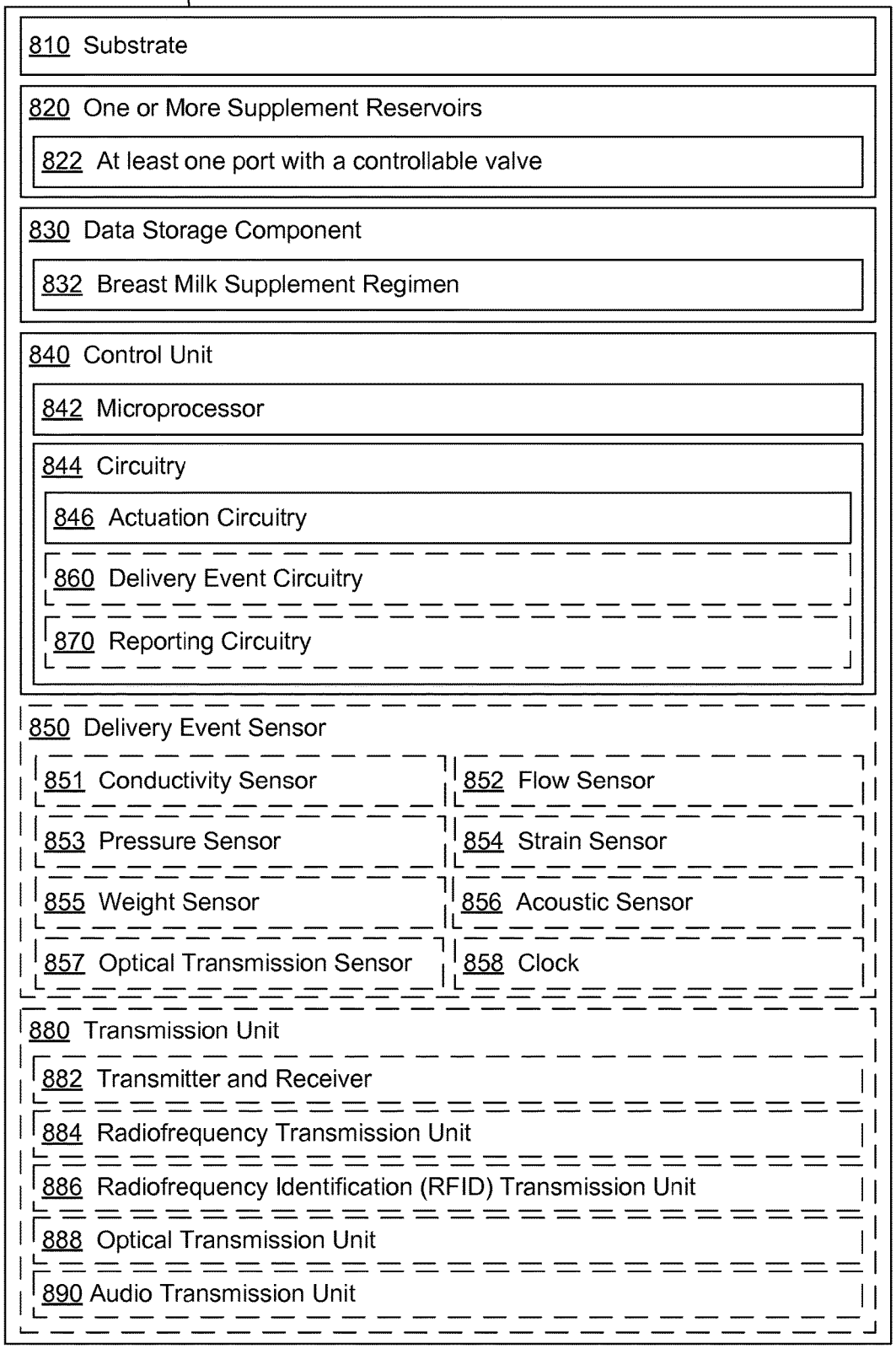
FIG. 8 illustrates an embodiment of a breast milk supplement delivery device.

FIG. 8 is a block diagram illustrating further non-limiting aspects of a breast milk supplement delivery device. Breast milk supplement delivery device 800 includes substrate 810 sized for placement on a surface of a breast region of a lactating female; one or more supplement reservoirs 820 including at least one port with a controllable valve 822; data storage component 830 including breast milk supplement regimen 832; and control unit 840 including microprocessor 842 and circuitry 844, control unit 840 operably coupled to data storage component 830 and to the controllable valve 822 of the one or more supplement reservoirs 820, the circuitry including actuation circuitry 846 configured to actuate the controllable valve 822 of at least one of the one or more supplement reservoirs 820 based on the breast milk supplement regimen 832.

In an embodiment, breast milk supplement delivery device 800 further includes at least one delivery event sensor 850 and associated delivery event circuitry 860 configured to receive information associated with a delivery event and reporting circuitry 870 configured to report the delivery event. For example, the breast milk supplement delivery device can include at least one delivery event sensor that senses and/or measures delivery of one or more breast milk supplements. For example, the breast milk supplement delivery device can include at least one delivery event sensor that senses and/or measures transit of one or more breast milk supplements from the one or more supplement reservoirs out of the associated at least one pore. In an aspect, the at least one delivery event sensor includes at least one of a flow sensor, a pressure sensor, a strain sensor, or a weight sensor. In an aspect, the at least one delivery event sensor includes at least one of a conductivity sensor, an acoustic sensor, an optical transmission sensor, or a clock.

In an aspect, the at least one delivery event sensor 850 includes conductivity sensor 851. For example, the conductivity sensor can include two or more electrodes, e.g., platinum electrodes, across which electrical conductivity is measured. Futagawa et al. "A miniature integrated multimodal sensor for measuring pH, EC and temperature for precision agriculture," (2012) Sensors 12:8338-8354, which is incorporated herein by reference. In an aspect, the conductivity sensor includes an amperometric, potentiometric, inductive, or toroidal conductivity sensor. For example, the conductivity sensor can include two electrodes spaced apart from each other for amperometric method of measuring conductivity. For example, the conductivity sensor can include one or more stainless steel or platinum rings for potentiometric method of measuring conductivity. For example, the conductivity sensor can include two or more toroidal transformers inductively coupled side by side for inductive method of measuring conductivity. In an aspect, the delivery event sensor includes an electrochemical impedance sensor. For example, electrochemical impedance measurements may be performed using two or more electrodes integrated into each of the one or more supplement reservoirs. See, e.g., Gutierrez, et al. "Electrochemically-based dose measurement for closed-loop drug delivery applications," IEEE Transducers'11, Beijing, China, Jun. 5-9, 2011, pp. 2839-2842, which is incorporated herein by reference.

In an aspect, the at least one delivery event sensor 850 includes a flow sensor 852. In an aspect, the flow sensor includes a conductivity sensor. See, e.g., U.S. Pat. No. 8,381,598 to Achard et al. titled "Method of measuring the flow rate of a liquid flowing in a fluidic channel and implementation device." In an aspect, the flow sensor is based on an integrated optical fiber cantilever. See, e.g., Lien et al. "Microfluidic flow rate detection based on integrated optical fiber cantilever," (2007) 7:1352-1356, which is incorporated herein by reference. In an aspect, the flow sensor includes flow sensing by directly measuring the electrical admittance of the fluid using two surface electrodes. See, e.g., U.S. Pat. No. 7,250,775 to Collins & Lee titled "Microfluidic devices and methods based on measurements of electrical admittance;" and Collins & Lee (2004) "Microfluidic flow transducer based on the measurement of electrical admittance," Lab on a Chip, 4:7-10, which are incorporated herein by reference.

In an aspect, the at least one delivery event sensor 850 includes a pressure sensor 853. For example, the delivery event can include a change in pressure in at least one of the one or more supplement reservoirs as fluid containing the one or more breast milk supplements leaves the reservoirs. For example, the delivery event can include a change in pressure associated with an infant pushing on and/or suckling from the reservoir. In an aspect, the pressure sensor includes at least one piezo-resistive pressure sensor. Non-limiting examples of miniature pressure sensors are commercially available (from, e.g., Keller America, Inc., Newport News, Va.; All Sensors, Morgan Hill, Calif.).

In an aspect, the at least one delivery event sensor 850 includes a strain sensor 854. In an aspect, the delivery event sensor includes a strain gauge. Non-limiting examples of miniature strain gauges are commercially available (from, e.g., Micro-Measurements, Vishay Precision Group, Inc., Raleigh N.C.; Strain Measurement Devices, Wallingford, Conn.; and LORD Corporation, Williston, Vt.).

In an aspect, the at least one delivery event sensor 850 includes a weight sensor 855. For example, the delivery event can include a change in weight of at least one of the one or more supplement reservoirs. In an aspect, the weight sensor includes a load sensor. For example the weight sensor can include a button or pancake style compression load cell. Non-limiting examples of load sensors are commercially available (from, e.g., FUTEK Advanced Sensor Technology, Inc., Irvine, Calif.).

In an aspect, the at least one delivery event sensor 850 includes acoustic sensor 856. In an aspect, the acoustic sensor includes a microphone. For example, the acoustic sensor can include a microphone for detecting the sounds of infant suckling. In an aspect, the acoustic sensor includes an ultrasound transducer. For example, transmission of an ultrasound signal through at least one of the one or more supplement reservoirs can measure fluid level. In an aspect, the ultrasound transducer includes a microfabricated ultrasonic transducer. See, e.g., Ladabaum et al. (1998) "Miniature drumheads: microfabricated ultrasonic transducers," Ultrasonics 36:25-29, which is incorporated herein by reference.

In an aspect, the at least one delivery event sensor 850 includes optical transmission sensor 857. In an aspect, the optical transmission sensor, e.g., a photodetector, senses the degree of light transmission through a supplement reservoir. In an aspect, the optical transmission sensor includes an optical fiber. For example, the optical transmission sensor can include a microfiber optical sensor for sensing refractive index, concentration, temperature, humidity, strain and/or current measurements in the liquid environment of the supplement reservoir. See, e.g., Lou et al. (2014) "Microfiber optical sensors: A review," Sensors 14:5823-5844, which is incorporated herein by reference.

In an aspect, the at least one delivery event sensor 850 includes clock 858. In an aspect, the clock is a real-time clock. In an aspect, the clock counts seconds, minutes, hours, day, date, month, and year. In an aspect, the clock is part of an integrated circuit. Non-limiting examples of integrated circuit real-time clocks are commercially available (from, e.g., Integrate Device Technology, San Jose, Calif.).

In an aspect, a control unit of a breast milk supplement delivery device includes delivery event circuitry. In an aspect, the delivery event circuitry includes circuitry configured to receive information associated with a delivery event. In an aspect, the delivery event circuitry includes circuitry configured to receive information from at least one delivery event sensor. In an aspect, the delivery event circuitry includes circuitry configured to receive information associated with at least one of a breast milk supplement type, an infant identifier, a dosage, a time, or a date.

In an aspect, a control unit includes reporting circuitry configured to report a delivery event. In an aspect, the reporting circuitry includes circuitry configured to report at least one of a breast milk supplement type, an infant identifier, a dosage, a time, or a date. For example, an infant identifier may be used to report a delivery event associated with one of a set of twins or other multiples nursing from same lactating female. In an aspect, the infant identifier includes at least one of a name, an identification code, e.g., alphanumeric code, or a biometric measurement. In an aspect, the reporting circuitry includes circuitry configured to report the delivery event through at least one of a radiofrequency transmission, a radiofrequency identification transmission, an optical transmission, or an audio transmission. In an aspect, the reporting circuitry includes circuitry configured to report the delivery event through at least one of an electrical wire, an optical fiber, or a removable storage medium. In an aspect, the reporting circuitry includes circuitry configured to report the delivery event to a personal electronic device. For example, the reporting circuitry can include circuitry configured to report a delivery event, e.g., a breast milk supplement type, an infant identifier, a dosage, a time, and/or a date, to a smart phone through a Bluetooth transmission. In an aspect, the reporting circuitry includes circuitry configured to report the delivery event to a computing device. For example, the reporting circuitry can include circuitry configured to report the delivery event to a remote computing device associated with a medical office, e.g., a pediatrician's office. In an aspect, the reporting circuitry includes circuitry configured to report the delivery event to a user interface associated with the breast milk supplement delivery device.

Transmission Unit

Returning to FIG. 8, in some embodiments, breast milk supplement delivery device 800 includes transmission unit 880 including circuitry and at least one antenna. In an aspect, transmission unit 880 includes transmitter and receiver 882. For example, the breast milk supplement delivery device can include at least one transmitter configured to transmit one or more signals and at least one receiver configured to receive one or more signals. In an aspect, transmission unit 880 is configured to transmit one or more signals having information associated with a delivery event. In an aspect, transmission unit 880 is configured to receive one or more signals having information associated with at least one of a breast milk supplement regimen, attributes of an infant, or a quality of breast milk of the lactating female. In an aspect, transmission unit 880 includes radiofrequency transmission unit 884. In an aspect, transmission unit 880 includes radiofrequency identification (RFID) transmission unit 886. In an aspect, transmission unit 880 includes optical transmission unit 888. In an aspect, transmission unit 880 includes audio transmission unit 890.

In some embodiments, a breast milk supplement delivery device includes at least one transmission unit. In an aspect, a breast milk supplement delivery device includes a transmission unit attached to a surface of the substrate, the transmission unit including circuitry and at least one antenna. In an aspect, the transmission unit is operably coupled to the control unit. In an aspect, the transmission unit is incorporated into the control unit. In an aspect, the transmission unit is configured to send signals including information associated with a delivery event. In an aspect, the transmission unit is configured to send signals including information associated with a delivery event to a personal electronic device, a computing device, and/or a user interface. In an aspect, the transmission unit sends a signal containing information associated with use and function of the breast milk supplement delivery device. For example, the transmission unit can send a signal to a personal electronic device, a computing device and/or a user interface to indicate that one or more of the breast milk supplements has been depleted and needs replacement. In an aspect, the transmission unit sends a signal containing information associated with the amount of any given supplement taken by the infant. In an aspect, the transmission unit sends a signal containing information associated with an output from at least one sensor, e.g., a delivery event sensor, an analyte sensor, or an infant presence detector.

A "transmission unit," as used herein, can be one or more of a variety of units that are configured to send and/or receive signals, such as signals carried as electromagnetic waves. In an aspect, a transmission unit includes at least one of volatile or non-volatile memory and/or a processor. In an aspect, the transmission unit is operably connected to a power source, such as a battery. In an aspect, the transmission unit is operably connected to a sensor, e.g., an analyte sensor, a delivery event sensor, and/or an infant presence detector. A transmission unit can be configured to transmit a signal in response to an interrogation signal. A transmission unit can include an energy harvesting unit, such as a unit configured to obtain energy from electromagnetic waves. A transmission unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference.

In an aspect, the transmission unit includes a radiofrequency transmission unit. For example, the transmission unit can include an oscillator and encoder configured to generate a programmable pulse position-modulated signal in the radio frequency range. See, for example, U.S. Pat. No. 4,384,288 to Walton, titled "Portable Radio Frequency Emitting Identifier," which is incorporated herein by reference. For example, the transmission unit can be configured to emit short-wavelength UHF radio waves.

In an aspect, the transmission unit includes a radio frequency identification (RFID) transmission unit. For example, the transmission unit can include a radio frequency identification device (RFID). For example, the transmission unit can be a passive RFID device, a semi-passive RFID device, or an active RFID device, depending on the embodiment. A transmission unit can be configured to be a transmitter of signals in the UHF range. A transmission unit including an RFID device can be configured to transmit signals in the UHF standard range utilized in a global region. See, for example, Chawla and Ha, "An Overview of Passive RFID," *IEEE Applications and Practice,* 11-17 (September 2007), which is incorporated herein by reference. A transmission unit can be configured to transmit at approximately 13.56 megahertz (MHz), or within the ISO 14443 standard parameters. See Patauner et al., "High Speed RFID/NFC at the Frequency of 13.56 MHz," presented at the *First International EURASIP Workshop on RFID Technology*, pages 1-4, 24-25 Sep. 2007, Vienna Austria, which is incorporated herein by reference.

In an aspect, a transmission unit can include at least two antennas. In an aspect, a transmission unit can include a self-compensating antenna system. An antenna can include dielectric material configured to electrically interact with one or more antennas. See, for example, U.S. Pat. No. 7,055,754 to Forester, titled "Self-Compensating Antennas for Substrates Having Differing Dielectric Constant Values," which is incorporated herein by reference. A transmission unit can include a hybrid backscatter system configured to function in an RFID, IEEE 802.11x standard and Bluetooth system. See, for example, U.S. Pat. No. 7,215,976 to Brideglall, titled "RFID Device, System and Method of Operation Including a Hybrid backscatter-based RFID Protocol Compatible with RFID, Bluetooth and/or IEEE 802.11x Infrastructure," which is incorporated herein by reference. A transmitter unit can be configured to transmit at approximately 131 kilohertz (KHz), for example as part of a RuBee™ (IEEE standard 1902.1) system (sold, for example, by Visible Assets™, Inc.). See, e.g., US Patent Application No. 2007/0171076 to Stevens and Waterhouse, titled "Low-frequency Radio Tag Encapsulating System," each of which are incorporated herein by reference. A transmission unit can include a near field communication (NFC) device. A transmission unit can include a Wireless Identification and Sensing Platform (WISP) device, manufactured by Intel Corporation, such as described in the "WISP: Wireless Identification and Sensing Platform" webpage (downloaded on Oct. 28, 2011) incorporated herein by reference.

In an aspect, the transmission unit includes an audio transmission unit. For example, the transmission unit can include one or more speakers. For example, the transmission unit can include a piezoelectric speaker. A variety of suitable piezoelectric speakers are available, including from Murata Manufacturing Co., Ltd., Smyrna, Ga. or Advanced Telemetry Systems, Isanti, Minn. In some embodiments, a breast milk supplement delivery device can include a piezoelectric speaker configured as part of an acoustic transmitter and also to act as a signaling device (e.g. to generate a beeping noise in response to a signal from the control unit).

In some embodiments, the transmission unit includes an ultrasonic transmitter. In some embodiments, the transmission unit includes an ultrasonic transducer. Multiple examples of ultrasonic transmitters and transducers are commercially available, often marketed under the term "ultrasonic sensors" as it is used in the industry (see, e.g. the Murata catalog titled "Ultrasonic Sensor" labeled S15E and dated Oct. 31, 2008, which is incorporated herein by reference). The transmitter unit can be configured as part of an ultrasonic ranging system. See: Wang, "A Design Method of Ultrasonic Ranging System with High Accuracy," *Journal of Computational Information Systems,* 7: 7 pages 2444-2451 (2011), which is incorporated herein by reference. The transmitter unit can be configured to communicate with an ultrasonic communication system. See: Chen and Wu, "Ultrasonic System with Infrared Communication Technology," *Journal of Computers,* vol. 6, no. 11, pages 2468-2475 (2011), which is incorporated herein by reference.

In some embodiments, the transmission unit includes an optical transmission unit. For example, an optical transmission unit can include one or more white light emitting diodes (LEDs). For example, an optical transmission unit can include an infrared laser. See: Kavehrad, "Sustainable Energy-Efficient Wireless Applications Using Light," *IEEE Communications Magazine,* vol. 48, no. 12, pages 66-73, (2010); and Fadlullah and Kavehrad, "Indoor High-Bandwidth Optical Wireless Links for Sensor Networks" *Journal of Lightwave Technology,* vol. 28, no. 21, pages 3086-3094 (2010), which are incorporated herein by reference.

Figure 9:
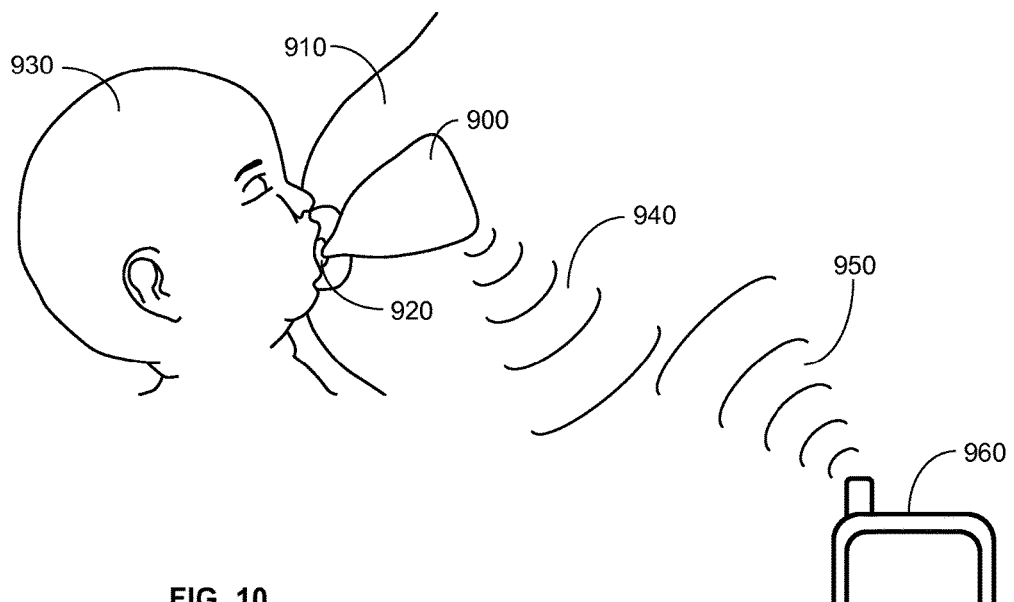
FIG. 9 illustrates an embodiment of a breast milk supplement delivery device such as shown in FIG. 8 placed on a breast region of a lactating female and in communication with a personal electronic device.
Figure 10:
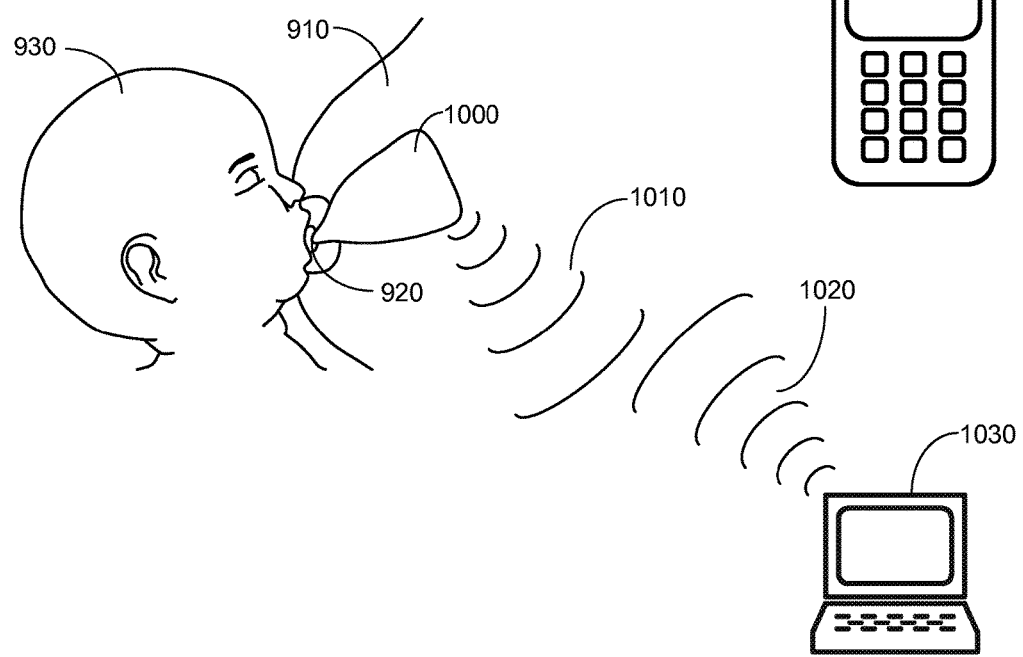
FIG. 10 illustrates a breast milk supplement delivery device such as shown in FIG. 8 placed on a breast region of a lactating female and in communication with a computing device.

FIGS. 9 and 10 illustrate further aspects of breast milk supplement delivery device. FIG. 9 shows an embodiment of a breast milk supplement delivery device 900 placed on the surface of a breast region 910 of a lactating female. At least one portion of breast milk supplement delivery device 900 is in close proximity to nipple 920 of the lactating female. Also shown is infant 930 nursing from nipple 920. Breast milk supplement delivery device 900 includes a transmission unit configured to transmit signals 940 to and receive signals 950 from a personal electronic device 960. For example, a breast milk supplement delivery device can include a transmission unit, e.g., a Bluetooth transmission unit, configured to transmit signals to and receive signals from a smart phone accessible to the lactating female. In an aspect, the personal electronic device includes a smart phone, a tablet, or other handheld personal electronic device. In an aspect, the personal electronic device includes a dedicated handheld electronic device designed specifically for use with a breast milk supplement delivery device.

FIG. 10 shows an embodiment of a breast milk supplement delivery device 1000 placed on the surface of a breast region 910 of a lactating female in proximity to nipple 920. Also shown is infant 930 nursing from nipple 920. Breast milk supplement delivery device 1000 includes a transmission unit configured to transmit signals 1010 to and receive signals 1020 from a computing device 1030. For example, a breast milk supplement delivery device can include a transmission unit configured to transmit signals to and receive signals from a remote computer associated with a healthcare provider, e.g., a pediatrician, neonatologist, or lactation specialist.

Analyte Sensors

Figure 11:
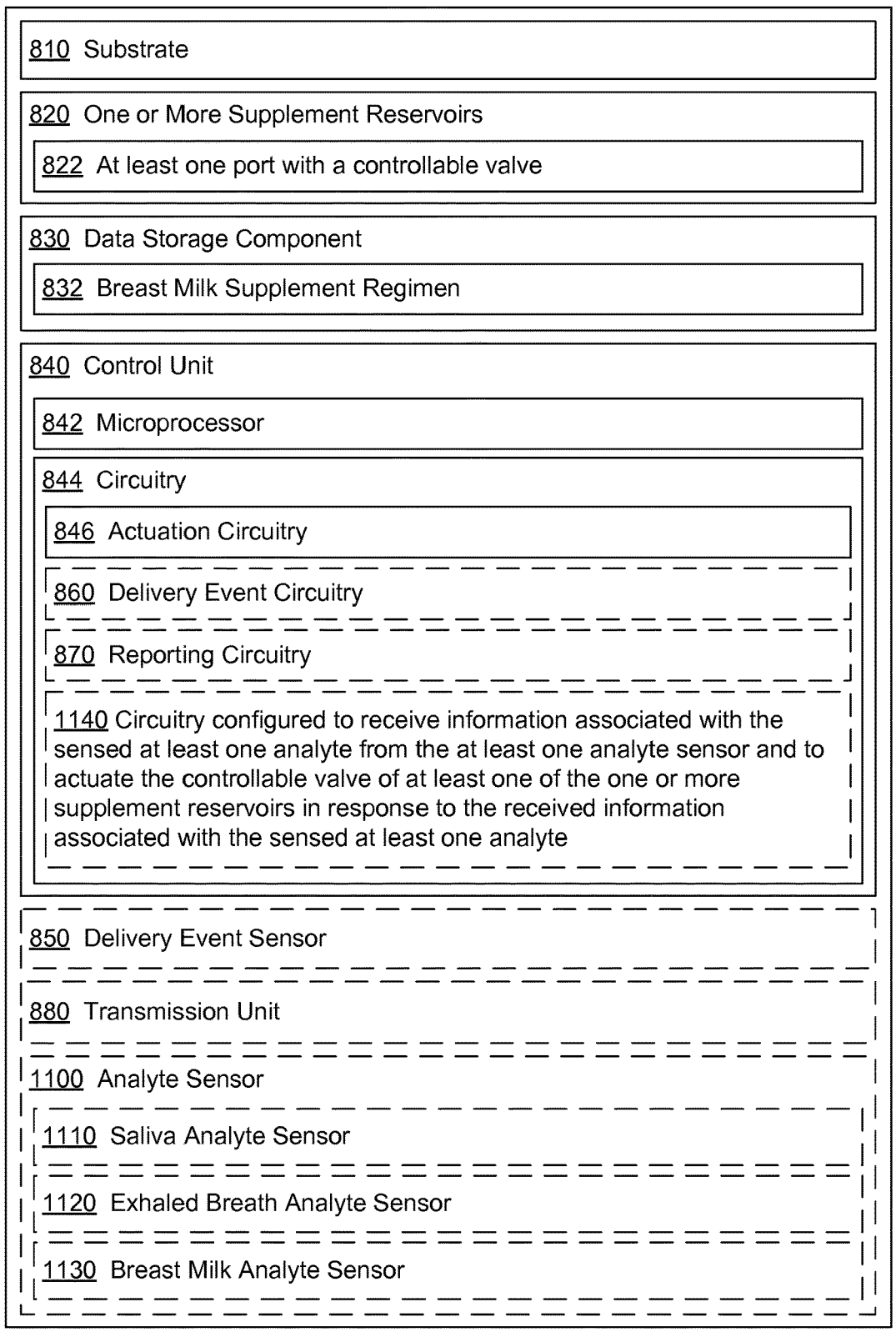
FIG. 11 shows aspects of a breast milk supplement delivery device such as shown in FIG. 8.

FIG. 11 illustrates further aspects of a breast milk supplement delivery device such as shown in FIG. 8. In some embodiments, breast milk supplement delivery device 800 includes at least one analyte sensor 1100 associated with the substrate 810 and operably coupled to the control unit 840, the at least one analyte sensor 1100 configured to sense at least one analyte. In an aspect, the at least one analyte sensor 1100 includes at least one saliva analyte sensor 1110 configured to sense at least one saliva analyte. In an aspect, the at least one analyte sensor 1100 includes at least one exhaled breath analyte sensor 1120 configured to sense at least one exhaled breath analyte. In an aspect, the at least one analyte sensor 1100 includes at least one breast milk analyte sensor 1130 configured to sense at least one breast milk analyte. In an aspect, control unit 840 includes circuitry 1140 configured to receive information associated with the sensed at least one analyte from the at least one analyte sensor 1100 and to actuate the controllable valve 822 of at least one of the one or more supplement reservoirs 820 in response to the received information associated with the sensed at least one analyte.

In an aspect, the at least one analyte sensor includes at least one saliva analyte sensor configured to sense at least one saliva analyte. In an aspect, the at least one saliva analyte sensor is configured to sense at least one component of the infant's saliva. The components of saliva can include, but are not limited to, inorganic components (e.g., sodium, potassium, magnesium, calcium, chloride, phosphate and bicarbonate ions, and to a lesser extent ions of ammonium, bromide, copper, fluoride, iodide, lithium, nitrate, perchlorate, and thiocyanate), organic compounds (non-protein and lipids, e.g., uric acid, bilirubin, creatinine, glucose, amino acids, lipids, mono/di-glycerides of fatty acid, putrescine, cadaverine, indole, linoleic acid, and arachidonic acid), protein/polypeptide compounds (e.g., amylase, secretory immunoglobulin A, carbonic anhydrase, albumin, mucins, lysozyme, lactoferrin, histatins, defensins, chitinases, proline-rich proteins, blood clotting factors, myeloperoxidase, calprotectins, cathepsin G, elastase, complements, macroglobulin, cysteine peptidase, DNases, RNases, kallikrein, and fibronectin), and hormones (e.g., catecholamines, cortisol, thyroxin, triidothyronine, testosterone, DHEA, progesterone, estradiol, aldosterone, prolactin, melatonin). See, e.g., Chiappin et al. (2007) "Saliva specimen: A new laboratory tool for diagnostic and basic investigation," Clinica Chimica Acta 383:30-40; Mamta et al. (2013) "Oral fluid: Biochemical composition and functions: A review," J. Pharm. Biomed. Sci. 37:1932-1941, which are incorporated herein by reference.

In an aspect, the at least one component of the infant's saliva is indicative of a nutritional need and/or medical condition. For example, the levels of linoleic acid and arachidonic acid in saliva may be correlated with dietary fatty acid intake. For example, the level of cortisol is higher in the saliva of preterm infants relative to that of full term infants. For example, cortisol levels may also be correlated with pain. For example, a sensed component of the infant's saliva may be indicative of an endocrine, immunologic, inflammatory, infectious, or other type of condition. For example, components of salvia can be used to diagnose adrenal conditions (e.g., Cushing's disease/syndrome), altered male or female hormone states, metabolic disturbances (insulin resistance, diabetes), benign and metastatic neoplasms, infectious conditions (HIV, viral hepatitis, Epstein Barr virus, cytomegalovirus amoebiasis), and allergic conditions (e.g., food allergies). For example, the level of C-reactive peptide in the saliva of infants may be useful in monitoring sepsis, postsurgical complications, and inflammation in neonates. See, e.g., Iyengar et al. (2014) "Detection and potential utility of C-reactive protein in saliva of neonates," Frontiers in Pediatrics, Volume 2, Article 131, which is incorporated herein by reference.

In an aspect, the at least one analyte sensor includes at least one exhaled breath analyte sensor configured to sense at least one exhaled breath analyte. In an aspect, the at least one exhaled breath analyte sensor is configured to sense at least one component of the exhaled breath of the infant. For example, the breast milk supplement delivery device can include at least one "electronic nose" for sensing volatile organic compounds exhaled in the infant's breath. See, e.g., de Lacy Costello et al. "A review of the volatiles from the healthy human body," J. Breath Res. 8 (2014) 014001 (29 pp), which is incorporated herein by reference. In an aspect, the at least one component of the exhaled breath of the infant is indicative of a nutritional need and/or medical condition. For example, the exhaled breath of the infant may include one or more volatile organic compounds indicative of a pulmonary infection (e.g., *P. aeruginosa*) or pulmonary condition (e.g., cystic fibrosis) requiring treatment with an antimicrobial agent. See, e.g., Joensen et al. (2014) "Exhaled breath analysis using electronic nose in cystic fibrosis and primary ciliary dyskinesia patients with chronic pulmonary infections," PLoS ONE 9(12): e115584, which is incorporated herein by reference.

In an aspect, the at least one analyte sensor includes at least one breast milk analyte sensor configured to sense at least one breast milk analyte. In an aspect, the at least one breast milk analyte sensor is configured to sense at least one component of the breast milk of the lactating female. In an aspect, the at least one breast milk analyte sensor is configured to sense at least one component of human milk. For example, the at least one breast milk analyte sensor can be adapted to sense macronutrients in the breast milk, e.g., a variety of proteins, non-protein nitrogen containing compounds, and fats. For example, the at least one breast milk analyte sensor can be adapted to sense micronutrients in the breast milk, e.g., vitamins and minerals. For example, the at least one breast milk analyte sensor can be adapted so sense bioactive components of breast milk, e.g., growth factors, hormones, and immunoglobulins. For a review of human breast milk components, see, e.g., Ballard & Morrow (2013) "Human milk composition: Nutrients and bioactive factors," Pediatr. Clin. North Am. 60:49-74, which is incorporated herein by reference.

In an aspect, the at least one analyte sensor is configured to sense fluids. In an aspect, the at least one analyte sensor is configured to sense a component in a fluid. As used herein, fluid includes both gasses and liquids individually or as mixtures. Sensors described herein can detect fluids, whether in gaseous state or liquid state. If the fluid is a liquid, it can interact with an analyte sensor on the surface of the breast milk delivery device or be drawn into the device by capillary action to interact with an internally placed analyte sensor. If the fluid is a gas, it can interact with an analyte sensor on the surface of the breast milk delivery device or be drawn into the device by gravity or forced exhalation of breath to interact with an internally placed analyte sensor.

In some embodiments, the at least one analyte sensor is attached to an external surface of the breast milk supplement delivery device. For example, a breast milk analyte sensor, a saliva sensor, and/or an exhaled breath sensor can be attached or incorporated into an external surface of the breast milk supplement delivery device to allow direct contact of the analyte sensor with the analyte, e.g., the breast milk analyte, the saliva analyte, and/or the exhaled breath analyte.

In some embodiments, the at least one analyte sensor is encased within the breast milk supplement delivery device. In an aspect, a wall and/or surface of the breast milk supplement delivery device defines one or more openings, the one or more openings forming a fluid conduit from a region exterior to the breast milk supplement delivery device to a region interior to the breast milk supplement delivery device. In an aspect, the fluid conduit is in contact with one or more analyte sensors. For example, the one or more openings can form a fluid conduit for analytes, e.g., analytes in infant saliva or exhaled breath, or in the breast milk of the lactating female, to pass from the exterior of the breast milk supplement delivery device into the interior of the breast milk supplement delivery device and for the analytes to come in contact with the one or more analyte sensors. In an aspect, the breast milk supplement delivery device includes a single opening associated with the at least one analyte sensor. In an aspect, the breast milk supplement delivery device includes a plurality of openings, for example arrayed as a series of holes or a mesh-like structure. In some embodiments, the breast milk supplement delivery device includes a plurality of openings, each opening including an associated sensor, such associated sensor can be the same or different type of sensor.

In an aspect, the at least one analyte sensor is operably coupled to the control unit. In an aspect, the at least one sensor is wirelessly coupled to the control unit. In an aspect, the at least one analyte sensor is operably coupled to the control unit through a connector, e.g., wires or circuitry. In an aspect, the at least one analyte sensor includes at least one chemical sensor, electrochemical sensor, integrated sensor chip, electronic nose, biosensor, or cantilever-based sensor. In an aspect, the at least one analyte sensor includes an electromagnetic sensor, an electrical current sensor, an electrical impedance sensor, a piezoelectric sensor, a magnetic sensor, an acoustic sensor, a radiofrequency sensor, or a radioactivity sensor. In an aspect, the at least one analyte sensor includes at least one piezo transducer, at least one MEMS device, at least one cavity resonator, at least one magneto-resistive sensors, at least one magnetic field sensors, and/or at least one thermal sensor. In an aspect, the at least one analyte sensor includes a biosensor with a physicchemical transducer, e.g., an optical, electrochemical, thermometric, or piezoelectric transducer.

The at least one "analyte sensor," as used herein, can be of a variety of types depending on the embodiment. The at least one analyte sensor can include at least one sensor responsive to changes in capacitance, or a measure of the ability of a configuration of materials to store electric charge. A general review of biosensors that detect changes in the dielectric properties of an electrode surface can be found in Berggren et al., "Capacitive Biosensors," *Electroanalysis* vol. 13, no. 3, 173-180, (2001), which is incorporated herein by reference. For example, at least one sensor can include a micromechanical biosensor with a fixed-fixed beam attached to an interdigitated capacitor (see, for example, Lim et al., "A Micromechanical Biosensor with Interdigitated Capacitor Readout," *Proceedings of the* 2011 *IEEE/ICME International Conference on Complex Medical Engineering*, May 22-25, Harbin, China, which is incorporated herein by reference). Sensors can also include nanowire nanosensors, for example as described in Cui et al., "Nanowire Nanosensors for Highly Sensitive and Selective Detection of Biological and Chemical Species," *Science*, vol. 293, 1289-1292 (2001), which is incorporated herein by reference. Sensors can include those utilizing antibodies secured to a graphene substrate. See Tehrani et al., "Detection of Monoclonal Antibodies using Chemically Modified Graphite Substances," *IEEE Sensors* 2010 *Conference Proceedings,* 428-431, (2010), which is incorporated herein by reference. In some embodiments, sensors include aptamer-modified graphene field-effect transistors, see Ohno et al., "Graphene Field-Effect Transistors for Label-Free Biological Sensors," *IEEE Sensors* 2010 *Conference Proceedings,* 903-906, (2010), which is incorporated herein by reference. A sensor can include a field effect transistor (FET), such as described in U.S. Pat. No. 7,507,675 to Zuilhof et al., titled "Device Manufacturing Method and Device," which is incorporated herein by reference. A sensor can include a nano-cantilever device, such as described in U.S. Pat. No. 7,612,424 to Espinosa and Ke, titled "Nanoelectromechanical Bistable Cantilever Device," which is incorporated herein by reference.

In an aspect, the at least one analyte sensor includes an optical biosensor. For example, the optical sensor can include an optical fiber. For example, the at least one analyte sensor can include an intrinsic optical biosensor in which interaction with the analyte occurs within an element of the optical fiber. For example, the at least one analyte sensor can include an extrinsic optical biosensor in which the light beam to and from a region of the sensor is influenced by the sensed analyte. In an aspect, the optical biosensor can be used to measure absorbance, reflectance, fluorescence, chemiluminescence, bioluminescence, and/or refractive index of the analyte. See, e.g., Bosch et al. (2007) "Recent development in optical fiber biosensor," Sensors 7:797-859, which is incorporated herein by reference.

In an aspect, the at least one analyte sensor includes a metamaterial combined with a binding agent, e.g., an antibody, receptor, ligand, or oligonucleotide, to form a biosensor. Binding to such a sensor causes a shift in resonance frequency. See, e.g., Chen et al. (2012) "Metamaterials application in sensing," Sensors 12:2742-2765, which is incorporated herein by reference. In an aspect, the analyte sensor includes a paper-based analyte sensor. See, e.g., Tao et al. (2011) "Metamaterials on paper as a sensing platform," Advanced Materials, 23:3197-3201, which is incorporated herein by reference.

In an aspect, the at least one analyte sensor includes a microcantilever-based sensor. For example, the at least one analyte sensor can include a mass-sensitive cantilever that responds to interaction with an analyte by bending or altering vibrational frequency. See, e.g., Vashist (2007) "A review of microcantilevers for sensing applications," AZojono J. Nanotechnology Online, DOI: 10.2240/azojono0115, which is incorporated herein by reference. In an aspect, the microcantilever-based sensor can include a binding moiety (e.g., an antibody, aptamer, ligand, receptor, or oligonucleotide) adapted to recognize and bind at least one of a saliva analyte, an exhaled breath analyte, or a breast milk analyte.

In an aspect, the at least one analyte sensor includes a sensor configured to sense volatile organic compounds. In an aspect, the at least one analyte sensor includes at least one of an acoustic wave, chemoresistant, or piezoelectric sensor. In an aspect, the at least one analyte sensor includes an electronic nose adapted to detect volatile analytes. See, e.g., Wilson and Baietto (2011) "Advances in electronic-nose technologies developed for biomedical applications," Sensors 11:1105-1176, which is incorporated herein by reference. In an aspect, a sensor adapted to detect a volatile analyte is incorporated into a single sensor chip. See, e.g., Hagleitner et al. (2001) "Smart single-chip gas sensor microsystem," Nature 414:293-296, which is incorporate herein by reference. In an aspect, the at least one analyte sensor is adapted to sense at least one volatile organic compound from the saliva and/or exhaled breath of the infant and from the breast milk of the lactating female. In addition to exhaled breath, saliva and breast milk are also sources of volatile organic compounds. See, e.g., de Lacy Costello et al. "A review of the volatiles from the healthy human body," J. Breath Res. 8 (2014) 014001 (29 pp), which is incorporated herein by reference.

In an aspect, the at least one analyte sensor is operably coupled to a transmission unit. In an aspect, the transmission unit operably coupled to the at least one analyte sensor is configured to transmit signals having information associated with a sensed analyte. For example, an analyte sensor positioned on an appendage or delivery tube of the breast milk supplement delivery device can include a transmission unit for wirelessly transmitting signals to the control unit. In an aspect, at least one of an analyte sensor, a delivery event sensor, or an infant presence detector is operably coupled to a transmission unit. See, e.g., Ruhanen et al., "Sensor-enabled RFID Tag and Handbook," from *Building Radio Frequency Identification for the Global Environment* (2008); Sample et al., "Design of an RFID-Based Battery-Free Programmable Sensing Platform," *IEEE Transactions on Instrumentation and Measurement*, vol. 57, no. 11, 2608-2615 (2008); Yeager et al., "Wirelessly-Charged UHF Tags for Sensor Data Collection," 2008 IEEE International Conference on RFID, Apr. 16-17, 2008, pages 320-327; U.S. Pat. Nos. 5,904,671 and 6,348,640 to Navot and Botton, each titled "Tampon Wetness Detection System;" U.S. Pat. No. 7,446,660 to Posamentier titled "Passive Environmental RFID Transceiver;" and U.S. Pat. No. 5,704,352 to Tremblay and Buckles, titled "Implantable Passive Bio-Sensor," which are each incorporated herein by reference.

Separator

In an aspect, at least one surface the breast milk supplement delivery device is covered by a peelable separator. For example, a surface of a breast milk supplement delivery device including an adhesive portion may further include a peelable separator to prevent the adhesive portion from prematurely adhering to a surface. For example, a surface of a substrate associated with the breast milk supplement delivery device including an adhesive portion may further include a peelable separator. For example, a surface of a housing associated with a breast milk supplement delivery device including an adhesive portion may further include a peelable separator. For example, a surface of a delivery tube associated with a breast milk supplement delivery device including an adhesive portion may further include a peelable separator. In an aspect, the peelable separator is relatively easily peeled away from the adhesive portion of the breast milk supplement delivery device using one's fingers. In an aspect, the separator includes a thin film. In an aspect, the thin film is formed from polyester, polyvinyl chloride, polyvinylidene chloride, polyethylene terephthalate. In an aspect, the thin film is further treated with silicone or a laminate film of polyolefin and quality paper or glassine. The thickness of the peelable separator is generally not more than 500 microns and is preferably 20-200 microns.

Power Source

In an aspect, a breast milk supplement delivery device includes a power source. In an aspect, the power source provides power to one or more components of the breast milk supplement delivery device. For example, the power source can provide power to at least one of the control unit, analyte sensors, delivery event sensors, infant presence sensors, transmission unit, actuators, user interface, and/or any other component of the breast milk supplement delivery device requiring power to function. In an aspect, the power source includes a wired connection to a standard electrical outlet. In an aspect, the power source includes an energy storage unit, e.g., a battery. For example, the battery can include a camera- or watch-sized alkaline, lithium, or silver-oxide battery or other appropriately sized and powered battery. In an aspect, the power source includes a rechargeable battery. In an aspect, the at least one rechargeable battery is charged through a wired connection, e.g., through a USB connection. In an aspect, the at least one rechargeable battery is charged wirelessly. For example, the breast milk supplement delivery device can include a wireless power receiver, e.g., an integrated circuit wireless power receiver, to wirelessly receive power from a wireless power transmitter.

In some embodiments, the breast milk supplement delivery device includes an energy harvesting unit. For example, the energy harvesting unit can include a unit configured to obtain energy from electromagnetic waves. See, for example, U.S. Pat. No. 7,479,886 to Burr titled "Antenna Capacitance for Energy Storage" and Sample et al., "Photovoltaic Enhanced UHF RFID Tag Antennas for Dual Purpose Energy Harvesting," 2011 *IEEE International Conference on RFID,* 146-153 (2011), which are each incorporated herein by reference.

Infant Presence Detector

In an aspect, a breast milk supplement delivery device includes an infant presence detector. In an aspect, the infant presence detector is configured to detect the presence or absence of an infant in proximity to the breast milk supplement delivery device and to provide an infant presence signal to the control unit. For example, one or more components of the breast milk supplement delivery device can be in an "off" mode in the absence of an infant and in an "on" mode in the presence of an infant. In an aspect, the actuation circuitry of the control unit is configured to actuate the controllable valve of the at least one of the one or more supplement reservoirs based on the infant presence signal. For example, the actuation circuitry can be triggered to at least partially open or close the controllable valve of at least one of the one or more supplement reservoirs to release one or more breast milk supplements in response to receiving a signal from a sensor configured to detect the presence, e.g., the proximity of, the nursing infant.

In an aspect, the infant presence detector includes at least one of a temperature sensor, a pressure sensor, an electrical conductivity sensor, a radar sensor, an ultrasonic sensor, a microphone, a camera, a photodetector, and/or a strain sensor. For example, the infant presence detector can include a pressure or contact sensor to detect the pressure of the infant's mouth on a portion of the breast milk supplement delivery device in proximity to the nipple. For example, the infant presence detector can include a temperature sensor to detect the temperature of the infant's mouth on a portion of the breast milk supplement delivery device in proximity to the nipple. Non-limiting examples of temperature, pressure, and strain sensors are commercially available (from, e.g., Keller America, Inc., Newport News, Va.; All Sensors, Morgan Hill, Calif.; Micro-Measurements, Vishay Precision Group, Inc., Raleigh N.C.; Strain Measurement Devices, Wallingford, Conn.; and LORD Corporation, Williston, Vt.). For example, the infant presence detector can include a photodetector or ambient light sensor to detect changes in light as the infant covers a portion of the breast milk supplement delivery device. Non-limiting examples of on-chip photodetectors and infrared proximity sensors are commercially available (from, e.g., Maxim Integrated, San Jose, Calif.). For example, the infant presence detector can include a microphone to detect sounds of the infant, e.g., suckling noises. For example, the infant presence detector can include a digital camera element to capture one or more images of the infant in proximity to the breast milk supplement delivery device. For example, the infant presence detector can include a miniature radar sensor to detect the proximity of the infant to the breast milk supplement delivery device. See, e.g., U.S. Pat. No. 5,361,070 to McEwan titled "Ultra-wideband radar motion sensor;" U.S. Pat. No. 5,573,012 to McEwan titled "Body monitoring and imaging apparatus and method;" U.S. Pat. No. 5,774,091 to McEwan titled "Short Range Micro-Power Impulse Radar with High Resolution Range Gate with Damped Transmit and Receive Cavities;" and Sharma et al. (2013) "Miniature radar for mobile devices," High Performance Extreme Computing Conference (HPEC), 2013 IEEE, 10-12 Sep. 2013, Waltham, Mass., pp 1-8, which are incorporated herein by reference. For example, the infant presence detector can include an ultrasonic range finder to detect the proximity of the infant to the breast milk supplement delivery device. See, e.g., Barzilay et al. (2010) "Micro-processor based improved ultrasonic direction and range finder," International Journal of Computer Science and Information Technologies 1:303-308, which is incorporated herein by reference.

Vibrating Component

In an aspect, a breast milk supplement delivery device includes a vibration delivery component configured to vibrate at least a portion of the substrate. In an aspect, the vibration delivery component includes a coin or pancake type vibration motor (from, e.g., Precision Microdrives, London, UK). In an aspect, the vibration delivery component includes a haptic actuator, e.g., electroactive polymers, or piezoelectric, electrostatic, or subsonic audio wave surface actuators.

Temperature Control Component

In an aspect, a breast milk supplement delivery device includes a temperature control component. In an aspect, the temperature control component is configured to control a temperature of at least one of a portion of the substrate and/or at least one of the one or more supplement reservoirs. In an aspect, temperature control component includes a heating component configured to heat at least one surface of the breast milk supplement delivery device, e.g., the surface of the device in contact with a suckling infant and/or the surface of the device in contact with the lactating female. In an aspect, the temperature control component includes a heating component configured to heat at least one surface of the breast milk supplement delivery device at or near a body temperature. For example, the temperature control component can include a heating component configured to heat at least one surface of the breast milk supplement delivery device to a temperature of about 97 degrees Fahrenheit to about 103 degrees Fahrenheit. In an aspect, the temperature control component includes a heating component configured to heat the contents of at least one of the one or more supplement reservoirs. For example, the temperature control component can include a heating component configured to heat the contents of at least one of the one or more supplement reservoirs to a temperature of about 97 degrees Fahrenheit to about 103 degrees Fahrenheit.

In an aspect, the heating component includes a material adapted to convert electrical energy into heat. In an aspect, the heating component includes at least one of metal heating elements, ceramic heating elements, composite heating elements, or combination heating elements. In an aspect, the heating component includes a metal heating component in the form of a wire, ribbon, or foil. In an aspect, the heating component includes a metallic resistance wire formed from at least one of kanthal (FeCrAl), nickel-chromium, or copper-nickel. In an aspect, the heating component includes a positive temperature coefficient ceramic material that becomes highly resistive above a composition-dependent threshold temperature. In an aspect, the temperature control component can include a thermistor for self-regulating a heating element of the temperature control component.

In an aspect, the heat component includes components of an exothermic chemical reaction. In an aspect, the heating component includes an air activated heating component. For example, an air activated heating component can include a mixture of cellulose, iron, water, activated carbon, vermiculite, and salt. In an aspect, the heating component includes a supersaturated solution and a nucleation center. For example, the heating component can include a supersaturated solution of sodium acetate and an iron nucleation center.

In some embodiments, the temperature control component includes a cooling component configured to cool at least one surface of the breast milk supplement device and/or the contents of at least one of the one or more supplement reservoirs. In an aspect, the temperature control component includes a thermoelectric cooling component (e.g., a Peltier device or thermoelectric cooler). See, e.g., Bottner et al. (2004) "New thermoelectric components using microsystem technologies," J. Microelectromechanical Systems 13:414-420, which is incorporated herein by reference. In some embodiments, the thermoelectric cooling device is adapted for both heating and cooling.

In an embodiment, a breast milk supplement delivery device includes a substrate sized for placement on a surface of a breast region of a lactating female in proximity to at least one nipple; and at least one flavoring associated with the substrate, the at least one flavoring intended to acclimate an infant to a food associated with the at least one flavoring.

Figure 12:
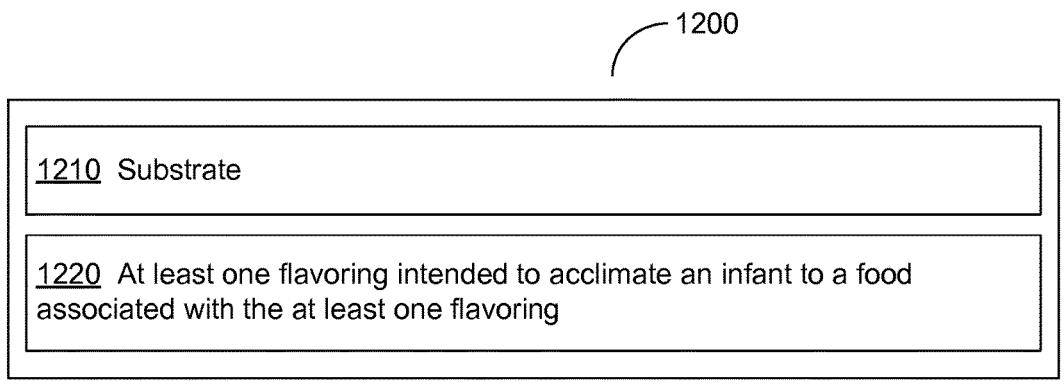
FIG. 12 illustrates an embodiment of a breast milk supplement delivery device including at least one flavoring.

FIG. 12 illustrates aspects of a breast milk supplement delivery device including a substrate and at least one flavoring. Breast milk supplement delivery device 1200 includes substrate 1210 sized for placement on a surface of a breast region of a lactating female; and at least one flavoring 1220 associated with the substrate, the at least one flavoring 1220 intended to acclimate an infant to a food associated with the at least one flavoring 1220. In an aspect, at least one flavoring 1220 is associated with a surface of substrate 1210. For example, the at least one flavoring can be included in a coating on the surface of the substrate. For example, the at least one flavoring can be included in a powder associated with the surface of the substrate. In an aspect, the surface of substrate 1210 including the at least one flavoring 1220 is configured to contact with the mouth region of a nursing infant.

Figure 13:
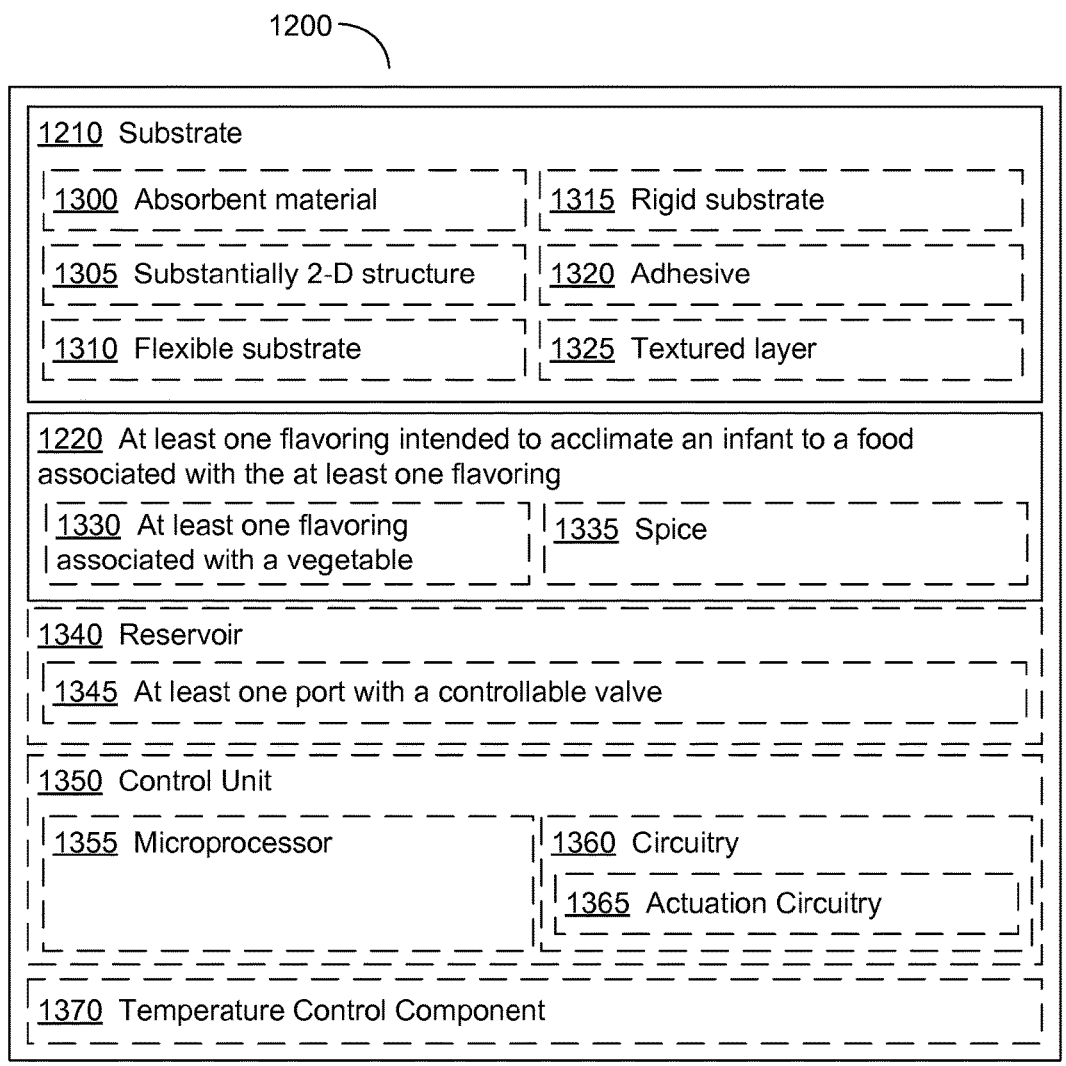
FIG. 13 shows further aspects of a breast milk supplement delivery device such as depicted in FIG. 12.

FIG. 13 illustrates further aspects of a breast milk supplement delivery device such as shown in FIG. 12. In an aspect, at least a portion of the substrate 1210 includes an absorbent material 1300. For example, at least a portion of the substrate can include a sponge-like or porous material capable of retaining a fluid, e.g., a fluid including the at least one flavoring. In an aspect, the at least one flavoring 1220 associated with the substrate 1210 is absorbed into the absorbent material 1300. For example, the at least one flavoring in a liquid form can be absorbed into the absorbent material and accessible to the nursing infant. In an aspect, the at least one flavoring 1220 is incorporated into a reservoir associated with the substrate 1210. For example, the breast milk supplement delivery device can include a reservoir attached to the substrate, the reservoir holding the at least one flavoring and including a removable cover to allow release of the at least one flavoring from the reservoir.

In an aspect, the substrate 1210 comprises a substantially two-dimensional structure 1305. Non-limiting examples of substrate configurations for a breast milk supplement delivery device have been described above herein. In an aspect, substrate 1210 comprises a flexible substrate 1310. In an aspect, substrate 1210 is formed from a flexible material. For example, the substrate can be a flexible substrate formed from a flexible material with properties that allow the flexible substrate to substantially conform to a surface of a breast region of a lactating female. In an aspect, substrate 1210 comprises a rigid substrate 1315. For example, the substrate can be formed from a rigid material with properties that allow the surface of the breast region of the lactating female to substantially conform to the surface of the substrate. In an aspect, substrate 1210 includes an adhesive 1320 on a surface conforming to the surface of the breast region of the lactating female. In an aspect, breast milk supplement delivery device 1200 includes a textured layer 1325 on at least a portion of the at least one surface of breast milk supplement delivery device 1200. For example, at least a portion of the substrate can be covered with a soft material, e.g., flannel. In an aspect, the textured layer is formed from an absorbent material, the absorbent material including the at least one flavoring. For example, the at least one flavoring can be absorbed into a soft, porous material, e.g., terry cloth or flannel. In an aspect, the at least one flavoring 1220 includes at least one flavoring associated with a vegetable 1330. In an aspect, the at least one flavoring includes a spice 1335. Additional non-limiting examples of flavorings have been described above herein.

In an aspect, breast milk supplement delivery device 1200 includes reservoir 1340 associated with substrate 1210, reservoir 1340 including at least one port with a controllable valve 1345, reservoir 1340 configured to hold at least one flavoring 1220. In an aspect, breast milk supplement delivery device 1200 includes control unit 1350 associated with substrate 1210 and including microprocessor 1355 and circuitry 1360, control unit 1350 operably coupled to the controllable valve 1345 of the reservoir 1340, circuitry 1360 including actuation circuitry 1365 configured to actuate the controllable valve 1345 of the reservoir 1340 to controllably release the at least one flavoring 1220.

In an aspect, breast milk delivery device 1200 includes a temperature control component 1370 configured to control a temperature of at least a portion of the substrate. For example, the breast milk supplement delivery device can include a heating component that slightly warms at least a portion of the substrate such that contact with a portion of the infant's skin and/or mouth is more comfortable for the infant. For example, the temperature control component can be configured to heat the at least one flavoring to increase the aroma of the at least one flavoring. Non-limiting examples of a temperature control component have been described above herein.

In an embodiment, a breast milk supplement delivery system includes a reusable component including a substrate sized for placement on a surface of a breast region of a lactating female, a data storage component configured to store a breast milk supplement regimen, and a control unit including a microprocessor and circuitry, the control unit operably coupled to the data storage component, the circuitry including actuation circuitry; and a disposable component configured to reversibly attach to the reusable component, the at least one disposable component including one or more supplement reservoirs, at least one of the one or more supplement reservoirs including a port with a controllable valve; wherein the actuation circuitry is configured to actuate the controllable valve of the at least one of the one or more supplement reservoirs based on the breast milk supplement regimen.

Figure 14:
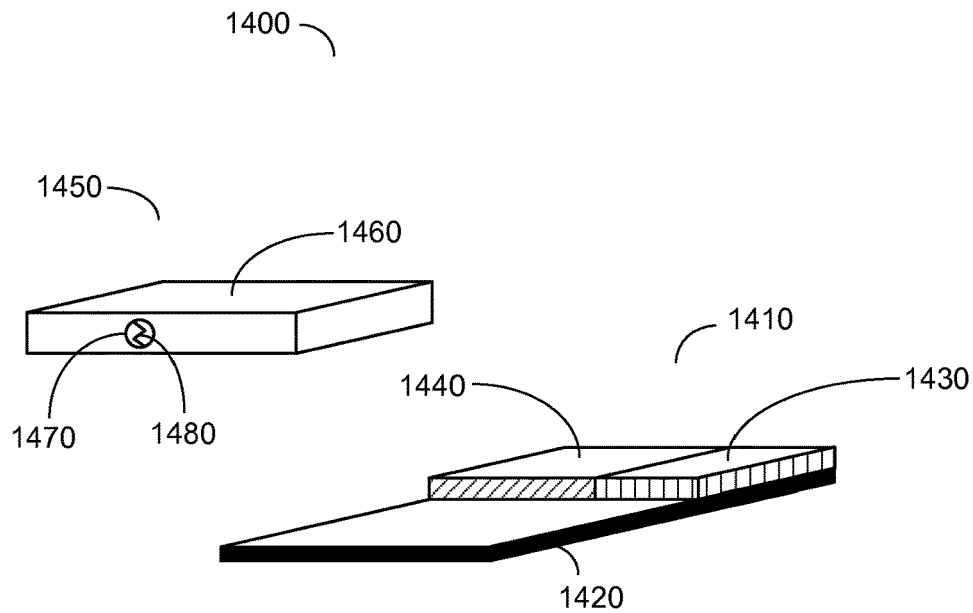
FIG. 14 illustrates an embodiment of a breast milk supplement delivery system including a reusable component and a disposable component.

FIG. 14 illustrates aspects of a breast milk supplement delivery system. Delivery system 1400 includes reusable component 1410 and disposable component 1450. Reusable component 1410 includes substrate 1420 sized for placement on a surface of a breast region of a lactating female; data storage component 1430 configured to store a breast milk supplement regimen; and control unit 1440 including a microprocessor and circuitry, control unit 1440 operably coupled to data storage component 1430, the circuitry including actuation circuitry. Disposable component 1450 is configured to reversibly attach to the reusable component 1410. The disposable component 1450 includes one or more supplement reservoirs 1460, at least one of the one or more supplement reservoirs including a port 1470 with a controllable valve 1480. The actuation circuitry of control unit 1440 is configured to actuate the controllable valve 1480 of the at least one of the one or more supplement reservoirs 1460 based on the breast milk supplement regimen.

Figure 15A:
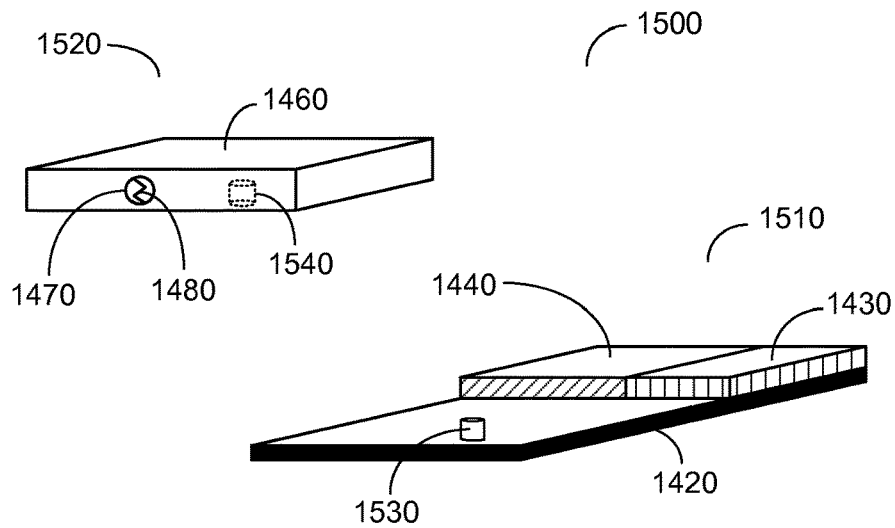
FIG. 15A illustrates an embodiment of a breast milk supplement delivery system including a reusable component and a disposable component.
Figure 15B:
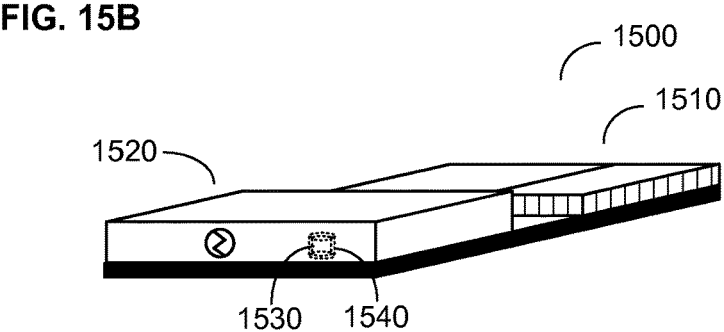
FIG. 15B illustrates further aspects of an embodiment of a breast milk supplement delivery system such as shown in FIG. 15A.

In an aspect, a breast milk supplement delivery system includes a docking site. In an aspect, the at least one disposable component is configured to reversibly attach to the substrate of the reusable component through the at least one docking site. FIGS. 15A and 15B illustrate non-limiting aspects of a breast milk supplement delivery system including a docking site. FIG. 15A shows delivery system 1500 including reusable component 1510 and disposable component 1520. Reusable component 1510 includes substrate 1420, data storage component 1430, and control unit 1440. Reusable component 1510 further includes docking site 1530, e.g., a pin, shown in this non-limiting embodiment associated with substrate 1420. Disposable component 1520 includes one or more supplement reservoirs 1460 including at least one port 1470 with a controllable valve 1480. Disposable component 1520 further includes a mating portion 1540, e.g., an aperture, intended to mate with docking site 1530 of the reusable component 1510. FIG. 15B shows further aspects of system 1500. Disposable component 1520 is shown reversibly attached to reusable component 1510 through docking site 1530 and mating portion 1540.

A breast milk supplement delivery system such as shown in FIGS. 14 and 15A and 15B can include at least one docking site configured to reversibly couple at least one disposable component to the reusable component of the delivery system. The docking site can take any of a number of configurations for reversibly coupling the at least one disposable component and the reusable component. In an aspect, the docking site includes a portion of the substrate of the reusable component to which the disposable component is coupled. In an aspect, the docking site includes grooves into which the disposable component slides. In an aspect, the docking site includes one or more pins configured to mate with apertures associated with the disposable component. In an aspect, the docking site includes one or more apertures configured to mate with pins associated with the disposable component. In an aspect, the at least one docking site is wired with circuitry to operably connect the disposable component with the control unit of the reusable component.

The reusable component of a breast milk supplement delivery system such as shown in FIGS. 14 and 15A and 15B includes a substrate sized for placement on the surface of the breast region of a lactating female. In an aspect, the substrate of the reusable component is sized for placement on the surface of the breast region of the lactating female adjacent to at least one nipple. In an aspect, the substrate of the reusable component includes a substantially two-dimensional structure. In an aspect, the substrate of the reusable component includes a flexible substrate. In an aspect, the flexible substrate is formed form a flexible material. For example, the substrate can be formed from a flexible material configured to substantially conform to the contours of a breast region of a lactating female. In an aspect, the substrate includes a substrate. For example, a rigid substrate can be configured such that the breast region of a lactating female substantially conforms to the surface of the rigid substrate. Non-limiting examples of substrate configurations and manufacture have been described above herein.

In an aspect, the substrate of the reusable component includes an adhesive on a surface conforming to the surface of the breast region of the lactating female. In an aspect, the adhesive on the surface of the substrate is reusable. For example, the adhesive may be sufficiently "tacky" or "sticky" to allow for repeated application and removal of the substrate from the breast region of the lactating female. In an aspect, the adhesive on the surface of the substrate is renewable. For example, the substrate of the reusable component can include one or more peelable layers of adhesive. For example, the adhesive can be associated with a thin peelable film. Non-limiting examples of adhesives have been described above herein.

In an aspect, at least one of the reusable component and the at least one disposable component includes a textured surface. For example, the reusable component and/or the at least one disposable component can include a textured surface on at least a portion of at least one surface of the reusable component and/or the at least one disposable component. For example, the reusable component of the delivery system can include a textured layer that at least partially covers at least one of the substrate, the data storage component, and/or the control unit to provide a soft surface for the nursing infant. In an aspect, the at least one disposable component includes a textured layer on at least a portion of at least one surface of the disposable component. For example, the at least one disposable component can include a layer of soft material intended to provide a soft surface for the nursing infant. Non-limiting examples of material for forming a textured layer or textured surface have been described above herein.

The reusable component of a breast milk supplement delivery system such as shown in FIGS. 14 and 15A and 15B includes a data storage component and a control unit. In an aspect, the data storage component is incorporated into the control unit. In an aspect, the data storage component comprises a removable data storage component. For example, the data storage component can include a removable memory card. Additional non-limiting examples of data storage components have been described above herein.

The data storage component of a breast milk supplement delivery system such as shown in FIGS. 14 and 15A and 15B is configured to store a breast milk supplement regimen. The breast milk supplement regimen includes at least one dosing regimen for one or more breast milk supplements. In an aspect, the breast milk supplement regimen includes a systematic or regulated plan for delivery of one or more breast milk supplements to a nursing infant. In an aspect, the breast milk supplement regimen includes one or more types of breast milk supplements and dosing and timing of said breast milk supplements.

In an aspect, the breast milk supplement regimen includes a personalized breast milk supplement regimen. In an aspect, the breast milk supplement regimen is personalized for an infant. In an aspect, the breast milk supplement regimen is personalized based at least one attribute of the infant. For example, the breast milk supplement regimen can be personalized for a specific infant based on the nutritional and/or medical needs of the specific infant. In an aspect, the breast milk supplement regimen is personalized based on at least one of age, weight, gender, genome, ethnicity, medical condition, or nutritional need of the infant.

In an aspect, the breast milk supplement regimen is personalized for the lactating female. In an aspect, the breast milk supplement regimen is personalized based on a quality of breast milk of the lactating female. For example, the breast milk supplement regimen can include one or more breast milk supplements, e.g., micronutrients, nutrients, and/or immunoglobulins, deficient in the breast milk of the lactating female. In an aspect, the breast milk supplement regimen is personalized based on at least one of a nutritional quality, microbial quality, or immunological quality of the breast milk of the lactating female.

In an aspect, the breast milk supplement regimen is adjustable. In an aspect, the breast milk supplement regimen is adjustable in response to a change in at least one of an attribute of an infant and/or a quality of breast milk of the lactating female. For example, the infant's nutritional needs may change as the infant ages and/or gains weight. For example, the quality of the breast milk of the lactating female may change in response to changing the female's diet or treating a medical condition.

A breast milk supplement delivery system such as shown in FIGS. 14 and 15A and 15B includes a disposable component including one or more supplement reservoirs. In an aspect, at least one of the one or more supplement reservoirs associated with the disposable component is adapted to contain one or more breast milk supplements. In an aspect, at least one of the one or more breast milk supplements includes a lipid, a protein, an oligosaccharide, a fatty acid, a carbohydrate, a nucleotide, or any combination thereof. In an aspect, at least one of the one or more breast milk supplements includes a nutrient, a micronutrient, a vitamin, an amino acid, or a mineral. In an aspect, at least one of the one or more breast milk supplements includes a therapeutic agent, an antimicrobial agent, a prebiotic, or a probiotic. In an aspect, at least one of the one or more breast milk supplements includes an appetite stimulator or an appetite suppressant. In an aspect, at least one of the one or more breast milk supplements includes a flavoring. In an aspect, the flavoring includes a flavoring preferred by an infant, e.g., sweet or salty flavoring. In an aspect, the flavoring includes a flavoring associated with a specific food type, the flavoring intended to acclimate an infant to the specific food type.

The one or more supplement reservoirs of the disposable component of the breast milk supplement delivery system include at least one port with a controllable valve. In an aspect, the controllable valve includes at least one of an electroactive material, a stimulus-responsive hydrogel, a shape-memory alloy, or a piezoelectric valve. Non-limiting examples of valves have been described above herein.

In an aspect, a breast milk supplement delivery system includes an absorbent portion. In an aspect, the absorbent portion is in fluid communication with the port of at least one of the one or more supplement reservoirs. For example, the absorbent portion is configured to absorb one or more breast milk supplements controllably released from the one or more supplement reservoirs. In an aspect, the absorbent portion is associated with at least one of the reusable component and/or the at least one disposable component. The absorbent portion is positioned within the delivery system such that a nursing infant's mouth will be in contact with the absorbent portion and any absorbed breast milk supplements.

In an aspect, a breast milk supplement delivery system includes a flow conduit including a first end and a second end, the first end of the flow conduit attached to the port and the second end of the flow conduit configured for positioning proximal to a nipple of the lactating female.

In an aspect, a breast milk supplement delivery system includes at least one delivery event sensor. In an aspect, the at least one delivery event sensor includes at least one of a flow sensor, a pressure sensor, a strain sensor, a weight sensor, a conductivity sensor, an acoustic sensor, an optical transmission sensor, or a clock. In an aspect, the control unit of the delivery system includes delivery event circuitry configured to receive information associated with a delivery event. In an aspect, the delivery event circuitry includes circuitry configured to receive information from at least one delivery event sensor. In an aspect, the delivery event circuitry includes circuitry configured to receive information associated with at least one of a breast milk supplement type, an infant identifier, a dosage, a time, or a date.

In an aspect, the control unit includes reporting circuitry configured to report a delivery event. In an aspect, the reporting circuitry includes circuitry configured to report the delivery event through at least one of a radiofrequency transmission, a radiofrequency identification (RFID) transmission, an optical transmission, or an audio transmission. In an aspect, the reporting circuitry includes circuitry configured to report the delivery event through at least one of an electrical wire, an optical transmission, or an audio transmission. In an aspect, the reporting circuitry includes circuitry configured to report at least one of a breast milk supplement type, a dosage, an infant identifier, a time, or a date. In an aspect, the reporting circuitry includes circuitry configured to report the delivery event to a computing device. In an aspect, the reporting circuitry includes circuitry configured to report the delivery event to a personal electronic device.

In an aspect, a breast milk supplement delivery system includes a transmission unit including circuitry and at least one antenna. In an aspect, the transmission unit includes at least one transmitter and at least one receiver. In an aspect, the transmission unit is associated with at least one of the reusable component and/or the disposable component. In an aspect, the reusable component includes a transmission unit and the disposable component includes a transmission unit. In an aspect, the transmission unit is operably coupled to the control unit of the reusable component.

In an aspect, the transmission unit includes at least one of a radiofrequency transmission unit, a radiofrequency identification (RFID) transmission, an optical transmission unit, or an audio transmission unit. In an aspect, the transmission unit is configured to transmit one or more signals having information associated with a delivery event.

In some embodiments, a breast milk supplement delivery system such as shown in FIGS. 14 and 15A and 15B includes one or more analyte sensors. In an aspect, the breast milk supplement delivery system includes at least one analyte sensor operably coupled to the control unit, the at least one analyte sensor configured to sense at least one analyte. In an aspect, the at least one analyte sensor includes at least one of a saliva analyte sensor, a breast milk analyte sensor, or an exhaled breath analyte sensor. In an aspect, the control unit includes circuitry configured to receive information associated with the sensed at least one analyte from the at least on analyte sensor. In an aspect, the control unit includes circuitry configured to actuate the controllable valve of at least one of the one or more supplement reservoirs in response to the received information associated with the sensed at least one analyte from the at least one analyte sensor.

In some embodiments, a breast milk supplement delivery system such as shown in FIGS. 14 and 15A and 15B includes at least one sensor configured to sense the presence or proximity of an infant. In an aspect, the breast milk supplement delivery system includes an infant presence detector. In an aspect, the infant presence detector is configured to detect the presence or absence of an infant in proximity to at least one of the reusable component and the disposable component, and to provide an infant presence signal to the control unit. In an aspect, the actuation circuitry of the control unit is configured to actuate the controllable valve of the at least one of the one or more supplement reservoirs based on the infant presence signal. For example, the actuation circuitry can be configured to only actuate the controllable valve when the infant is in proper proximity to one or more components of the breast milk supplement delivery system. In an aspect, the infant presence detector includes at least one of a temperature sensor, a pressure sensor, an electrical conductivity sensor, a radar sensor, an ultrasonic sensor, a microphone, a camera, a photodetector, or a strain sensor. Non-limiting examples of infant presence detectors have been described above herein.

In some embodiments, a breast milk supplement delivery system includes a vibration delivery component configured to vibrate at least a portion of at least one of the reusable component and the disposable component. In some embodiments, a breast milk supplement delivery system includes a temperature control component configured to control a temperature of at least one of the reusable component and the disposable component. For example, the temperature control component can heat at least one surface of the reusable component for the comfort of a nursing infant and/or the lactation female. For example, the temperature control component can heat the contents of the one or more supplement reservoirs of the disposable component for the comfort of a nursing infant.

In some embodiments, a breast milk supplement delivery device includes a substrate sized for placement on a surface of a breast region of a lactating female; one or more supplement reservoirs associated with the substrate, at least one of the one or more supplement reservoirs including a port with a controllable valve, the one or more supplement reservoirs adapted to contain one or more breast milk supplements; one or more analyte sensors associated with the substrate; and a control unit operably coupled to the controllable valve of the at least one of the one or more supplement reservoirs and to the one or more analyte sensors, the control unit including a microprocessor and circuitry, the circuitry including circuitry configured to receive analyte information from the one or more analyte sensors; and actuate the controllable valve of the at least one of the one or more supplement reservoirs to modulate release of the one or more breast milk supplements in response to the received analyte information.

Figure 16:
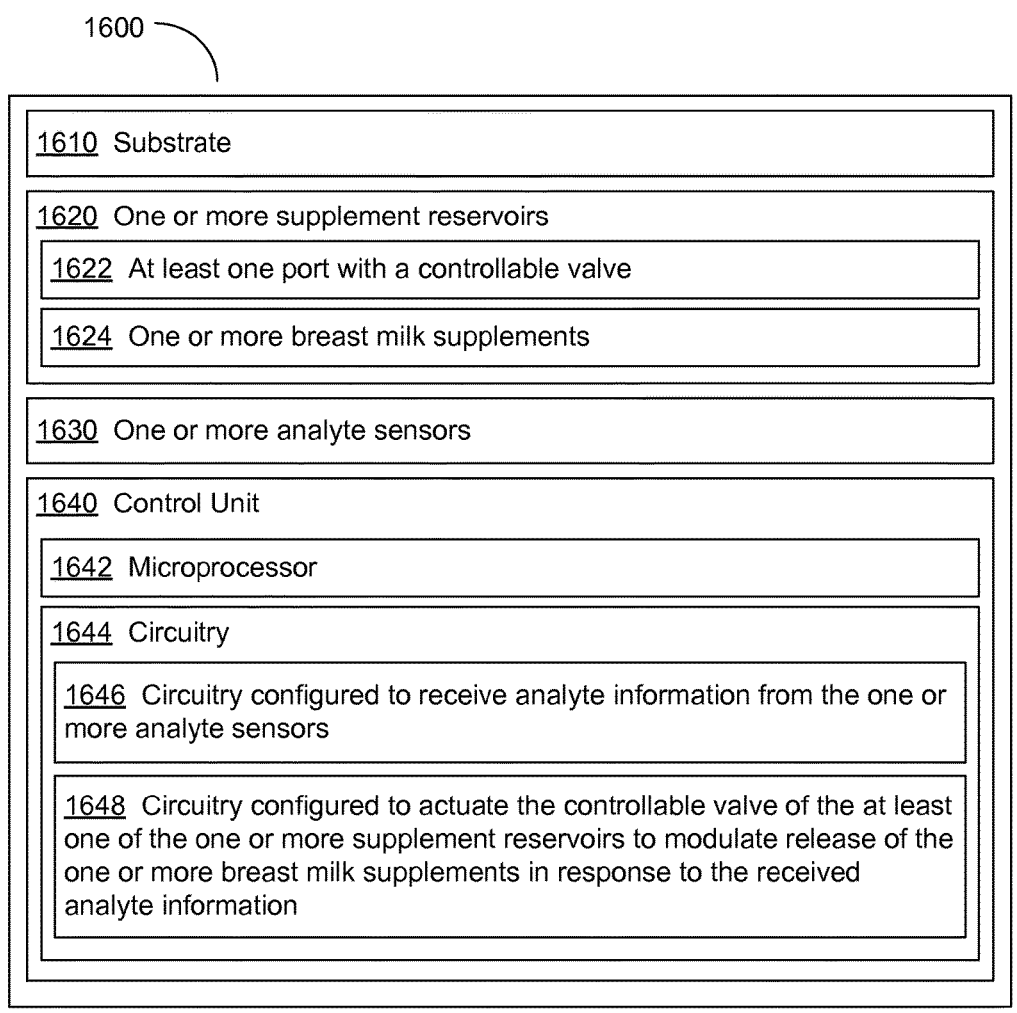
FIG. 16 illustrates an embodiment of a breast milk supplement delivery device including one or more analyte sensors.

FIG. 16 illustrates aspects of a breast milk supplement delivery device including one or more analyte sensors. Breast milk supplement delivery device 1600 includes substrate 1610 sized for placement on a surface of a breast region of a lactating female. In an aspect, substrate 1610 is sized for placement on the surface of the breast region of the lactating female in proximity to at least one nipple. In an aspect, substrate 1610 comprises a substantially two-dimensional structure. For example, the substrate can be circular, oval, rectangular, trapezoidal, or polygonal. In an aspect, substrate 1610 comprises a substantially planar structure. In an aspect, substrate 1610 includes a flexible substrate. In an aspect, substrate 1610 is formed from a flexible material. For example, the substrate can be formed from a flexible polymer configured to substantially conform to the surface of the breast region of the lactating female. In an aspect, substrate 1610 includes a rigid substrate. For example, the substrate can be formed from a rigid biocompatible plastic. In an aspect, substrate 1610 includes an adhesive on a surface conforming to the surface of the breast region of the lactating female.

In an aspect, breast milk supplement delivery device 1600 includes at least one textured surface. In an aspect, the at least one textured surface is associated with at least one of the substrate, the one or more supplement reservoirs, the data storage component, and/or the control unit of the breast milk supplement delivery device.

Breast milk supplement delivery device 1600 includes one or more supplement reservoirs 1620. In an aspect, at least one of the one or more supplement reservoirs 1620 is disposed between two or more layers forming the substrate 1610. In an aspect, at least one of the one or more supplement reservoirs 1620 is attached to a surface of substrate 1610. In an aspect, at least one of the one or more supplement reservoirs 1620 is detachable from substrate 1610.

At least one of the one or more supplement reservoirs 1620 includes a port including a controllable valve 1622. In an aspect, the controllable valve 1622 includes at least one of an electroactive material, a stimulus-responsive hydrogel, or a shape-memory alloy. In an aspect, the controllable valve 1622 includes a piezoelectric valve.

The one or more supplement reservoirs 1620 are adapted to contain one or more breast milk supplements 1624. In an aspect, at least one of the one or more breast milk supplements 1624 includes a lipid, a protein, an oligosaccharide, a fatty acid, a carbohydrate, or a nucleotide, or any combination thereof. In an aspect, at least one of the one or more breast milk supplements 1624 includes a nutrient, a micronutrient, a vitamin, an amino acid, or a mineral. In an aspect, at least one of the one or more breast milk supplements 1624 includes a therapeutic agent, an antimicrobial agent, a prebiotic, or a probiotic. In an aspect, at least one of the one or more breast milk supplements 1624 includes an appetite stimulator or an appetite suppressant. In an aspect, at least one of the one or more breast milk supplements 1624 includes a flavoring. In an aspect, the flavoring includes a flavoring preferred by an infant, e.g., sweet or salty. In an aspect, the flavoring includes a flavoring associated with a specific food type, the flavoring intended to acclimate an infant to the specific food type.

In an aspect, the port with the controllable valve 1622 is in fluid communication with a flow conduit, the flow conduit including a first end attached to the port and a second end configured for positioning proximal to a nipple of the lactating female. In an aspect, the port with the controllable valve 1622 is in fluid communication with an absorbent layer. In an aspect, the absorbent layer covers at least a portion of the one or more supplement reservoirs 1620. In an aspect, the absorbent layer comprises an outer layer on a surface of substrate 1610.

Breast milk supplement delivery device 1600 includes one or more analyte sensors 1630. In an aspect, at least one of the one or more analyte sensors 1630 includes a saliva analyte sensor. In an aspect, at least one of the one or more analyte sensors 1630 includes an exhaled breath analyte sensor. In an aspect, at least one of the one or more analyte sensors 1630 includes a breast milk analyte sensor. In an aspect, at least one of the one or more analyte sensors 1630 is configured to sense at least one of a lipid, a protein, an oligosaccharide, a fatty acid, a carbohydrate, or a nucleotide, or any combination thereof. In an aspect, at least one of the one or more analyte sensors 1630 is configured to sense at least one of a nutrient, a micronutrient, a vitamin, an amino acid, or a mineral. In an aspect, at least one of the one or more analyte sensors 1630 is configured to sense a microorganism. In an aspect, at least one of the one or more analyte sensors 1630 is incorporated into the substrate 1610. In an aspect, at least one of the one or more analyte sensors 1630 is attached to the substrate 1610. In an aspect, at least one of the one or more analyte sensors 1630 is associated with an appendage, a first end of the appendage attached to the substrate and a second end of the appendage configured for placement adjacent to a nipple of the lactating female. In an aspect, the appendage is associated with a flow conduit, the flow conduit including a first end attached to the port and a second end configured for positioning adjacent to the nipple of the lactating female.

Breast milk supplement delivery device 1600 includes control unit 1640 operably coupled to the controllable valve 1622 of the at least one of the one or more supplement reservoirs 1620 and to the one or more analyte sensors 1630. Control unit 1640 includes microprocessor 1642 and circuitry 1644. Circuitry 1644 includes circuitry 1646 configured to receive analyte information from the one or more analyte sensors 1630 and circuitry 1648 configured to actuate the controllable valve 1622 of the at least one of the one or more supplement reservoirs 1620 to modulate release of the one or more breast milk supplements in response to the received analyte information.

In some embodiments, breast milk supplement delivery device 1600 includes at least one delivery event sensor. In an aspect, the at least one delivery event sensor includes at least one of a flow sensor, a pressure sensor, a strain sensor, a weight sensor, a conductivity sensor, an acoustic sensor, an optical transmission sensor, or a clock. In an aspect, control unit 1640 includes delivery event circuitry configured to receive information associated with a delivery event. In an aspect, the delivery event circuitry includes circuitry configured to receive information from at least one delivery event sensor. In an aspect, the delivery event circuitry includes circuitry configured to receive information associated with at least one of a breast milk supplement type, an infant identifier, a dosage, a time, or a date.

In some embodiments, control unit 1640 of breast milk supplement delivery device 1600 includes reporting circuitry configured to report a delivery event. In an aspect, the reporting circuitry includes circuitry configured to report the delivery event through at least one of a radiofrequency transmission, a radiofrequency identification (RFID) transmission, an optical transmission, or an audio transmission. In an aspect, the reporting circuitry includes circuitry configured to report the delivery event through at least one of an electrical wire, an optical fiber, or a removable storage medium. In an aspect, the reporting circuitry includes circuitry configured to report at least one of a breast milk supplement type, a dosage, an infant identifier, a time, or a date. In an aspect, the reporting circuitry includes circuitry configured to report the delivery event to a personal electronic device. In an aspect, the reporting circuitry includes circuitry configured to report the delivery event to a computing device.

In some embodiments, breast milk supplement delivery device 1600 includes a transmission unit including circuitry and at least one antenna. In an aspect, the transmission unit is operably coupled to the control unit. In an aspect, the transmission unit is incorporated into the control unit. In an aspect, the transmission unit includes at least one transmitter and at least one receiver. In an aspect, the transmission unit includes at least one of a radiofrequency transmission unit, a radiofrequency identification (RFID) transmission unit, an optical transmission unit, or an audio transmission unit. In an aspect, the transmission unit is configured to transmit one or more signals having information associated with a delivery event.

In an aspect, breast milk supplement delivery device 1600 includes an infant presence detector. In an aspect, the infant presence detector is configured to detect the presence or absence of an infant in proximity to breast milk supplement delivery device 1600, and to provide an infant presence signal to the control unit. In an aspect, the actuation circuitry of the control unit is configured to actuate the controllable valve of the at least one of the one or more supplement reservoirs based on the infant presence signal. For example, the actuation circuitry can be configured to only actuate the controllable valve when the infant is in proper proximity to the breast milk supplement delivery device. In an aspect, the infant presence detector includes at least one of a temperature sensor, a pressure sensor, an electrical conductivity sensor, a radar sensor, an ultrasonic sensor, a microphone, a camera, a photodetector, or a strain sensor. Non-limiting examples of infant presence detectors have been described above herein.

In some embodiments, breast milk supplement delivery device 1600 includes a vibration delivery component configured to vibrate at least a portion of the substrate of breast milk supplement delivery device 1600. In some embodiments, breast milk supplement delivery device 1600 includes a temperature control component configured to control a temperature of at least one of a portion of the substrate and at least one of the one or more supplement reservoirs. For example, the temperature control component can heat at least one surface of the substrate or other surface of the breast milk supplement delivery device for the comfort of a nursing infant and/or the lactating female. For example, the temperature control component can heat the contents of the one or more supplement reservoirs for the comfort of a nursing infant.

In some embodiments, a breast milk supplement delivery device includes a housing sized for placement on a surface near a breast region of a lactating female, the housing including one or more supplement reservoirs, at least one of the one or more supplement reservoirs including a port with a controllable valve; a data storage component including a breast milk supplement regimen; and a control unit including a microprocessor and circuitry, the control unit operably coupled to the data storage component and to the controllable valve of the at least one of the one or more supplement reservoirs, the circuitry including actuation circuitry configured to actuate the controllable valve of the at least one of the one or more supplement reservoirs based on the breast milk supplement regimen; and at least one delivery tube having a first end and a second end, the first end of the at least one delivery tube in fluid communication with the port with the controllable valve, the second end of the at least one delivery tube configured for placement in proximity to a nipple of the lactating female.

Figure 17A:
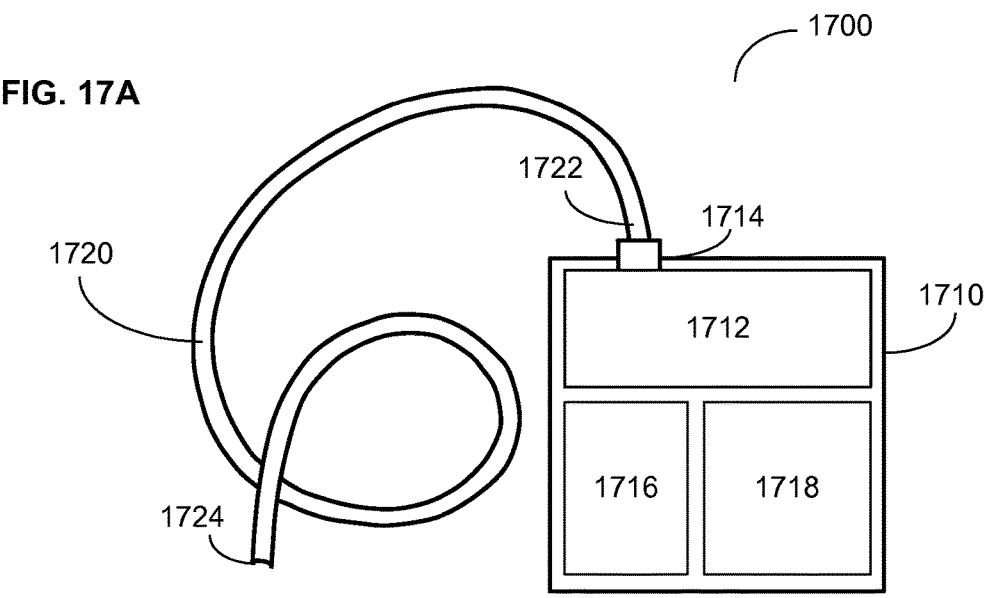
FIG. 17A illustrates an embodiment of a breast milk supplement delivery device including a housing and at least one delivery tube.
Figure 17B:
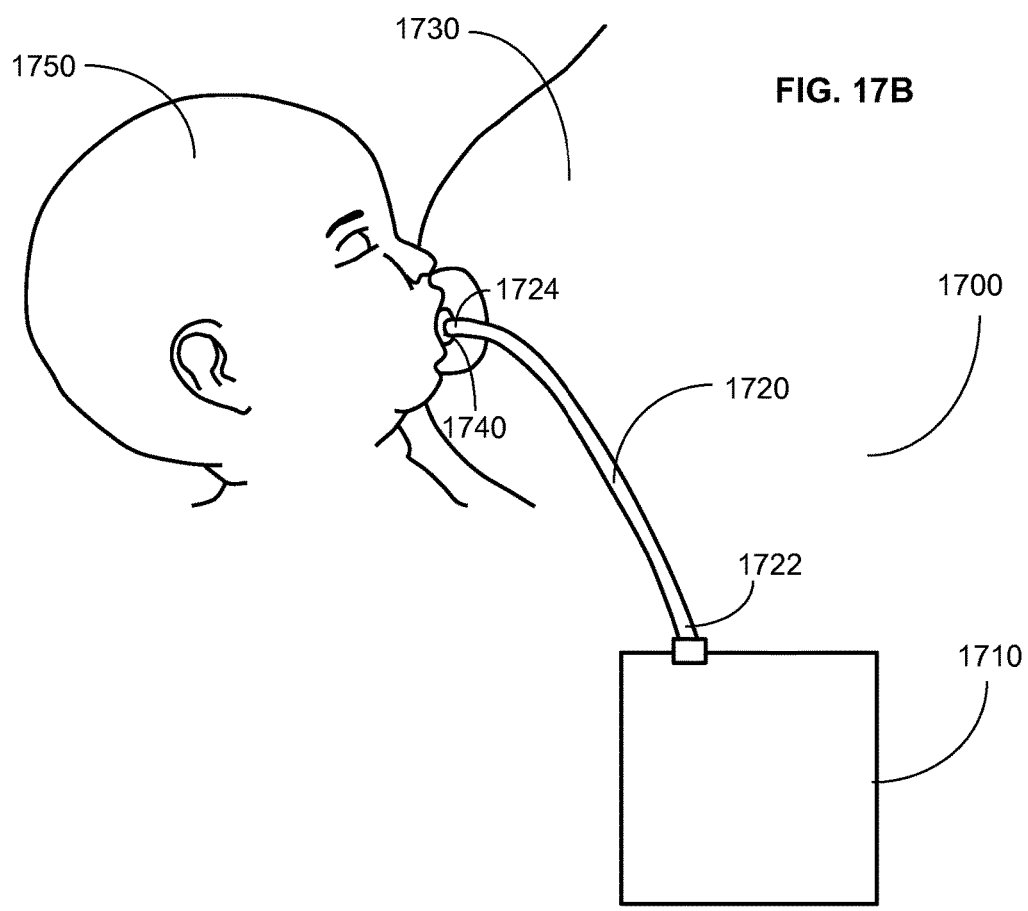
FIG. 17B shows placement of an embodiment of a breast milk supplement delivery device such as shown in FIG. 17A in proximity to the nipple of a lactating female.

FIGS. 17A and 17B illustrate aspects of a breast milk supplement delivery device including a housing and at least one delivery tube. FIG. 17A illustrates aspects of breast milk supplement delivery device 1700. Breast milk supplement delivery device 1700 includes a housing 1710 sized for placement on a surface near a breast region of a lactating female. Housing 1710 includes one or more supplement reservoirs 1712, at least one of the one or more supplement reservoirs including a port with a controllable valve 1714; a data storage component 1716 including a breast milk supplement regimen; and control unit 1718. Breast milk supplement delivery device 1700 includes at least one delivery tube 1720 having a first end 1722 and a second end 1724, the first end 1722 of the at least one delivery tube 1720 is in fluid communication with the port with the controllable valve 1714. FIG. 17B illustrates further aspects of breast milk supplement delivery device 1700. Breast milk supplement delivery device 1700 is shown including housing 1710 and at least one delivery tube 1720. Housing 1710 is shown near a breast region 1730 of a lactating female. The at least one delivery tube 1720 is shown attached at a first end 1722 to a port with a controllable valve associated with housing 1710. A second end 1724 of the at least one delivery tube 1720 is shown in close proximity to a nipple 1740 of the lactating female. Also shown is an nursing infant 1750. The second end 1724 of the at least one delivery tube 1720 is in a position to deliver one or more breast milk supplements to the nursing infant 1750.

Breast milk supplement delivery device 1700 includes a housing 1710. In an aspect, the housing is sized for placement on the body of the lactating female. For example, the housing can be sized for placement on the chest or waist region of the lactating female. For example, the housing can be sized for placement on the arm or leg region of the lactating female. In an aspect, the housing is sized for placement on a furniture surface near a breast region of the lactating female. For example, the housing can be sized for placement on a chair, a sofa, a bed, or a table. In some embodiments, the housing is sized for placement on the ground. For example, a breast milk supplement delivery device for use in large domesticated animals can include a housing sized for placement on the ground in the vicinity of the large domesticated animal, e.g., a pig, cow, goat, or horse.

In an aspect, housing 1710 comprises a wearable housing. In an aspect, housing 1710 includes an adhesive on at least one surface conforming to the surface near the breast region of the lactating female. For example, one surface of the housing can include an adhesive that allows the housing to be adhered to the surface of the skin. For example, one surface of the housing can include a pressure sensitive adhesive that allows the housing to be reversibly adhered to a body portion, e.g., a breast, chest, torso, arm, or leg, of the lactating female. In an aspect, housing 1710 includes one or more straps, the one or more straps sized to extend around a body portion of the lactating female. For example, the housing can include a strap that allows the housing to be hung from the neck of the lactating female. For example, the housing can include one or more straps to strap the housing to the chest, torso, arm, or leg of the lactating female. In an aspect, housing 1710 is sized for at least one of placement in an article of clothing or placement on an article of clothing. For example, housing 1710 can be sized for placement into a nursing bra or nursing shirt. For example, housing 1710 can be sized for placement in a pair of pants, e.g., in the waistband of the pair of pants.

Housing 1710 includes one or more supplement reservoirs 1712, at least one of the one or more supplement reservoirs 1712 including a port with a controllable valve 1714. In an aspect, the controllable valve 1714 includes at least one of a pneumatic valve, a solenoid valve, a poppet valve, a diaphragm valve, a piezoelectric valve, or a pinch valve. In an aspect, the controllable valve includes a pneumatic solenoid valve. In an aspect, the controllable valve includes a miniature pneumatic solenoid valve. Miniature pneumatic solenoid valves for use in medical devices are commercially available (e.g., from Parker Hannifin Corporation, Hollis N.H.; Pneumadyne, Inc., Plymouth, Minn.). In an aspect, the controllable valve includes a solenoid valve. In an aspect, the controllable valve includes a poppet solenoid valve. For example, the controllable valve can include a poppet solenoid valve through which a liquid supplement flows through a plunger, spring and internal body of the valve. In an aspect, the controllable valve includes a diaphragm isolation valve. For example, the controllable valve can include a diaphragm isolation valve in which a diaphragm is placed such that the poppet pushes on one side while the fluid is on the other side, thereby isolating the fluid. In an aspect, the controllable valve includes a pinch valve. In an aspect, the pinch valve includes a flow conduit that is pinched to control flow of fluid through the pinch valve. For example, pinch valve can include a flexible rubber sleeve and a component capable of controllably pinching the flexible rubber sleeve to control the flow of fluid. In an aspect, the controllable valve includes at least one of a ball valve, a butterfly valve, a gat valve, a globe valve, a needle valve, or a plug valve.

In an aspect, the controllable valve 1714 includes an actuator, the actuator operably coupled to actuation circuitry. In an aspect, the actuator includes at least one of a pneumatic actuator, a hydraulic actuator, a magnetic actuator, or an electric actuator. For example, the controllable valve can include a solenoid valve including an electric actuator that at least partially opens and closes in response to an electrical signal generated by the actuation circuitry. In an aspect, the actuation circuitry is configured to at least partially open or close the controllable valve. In an aspect, the actuation circuitry is configured to at least one of open the controllable valve, close the controllable valve, change a pressure threshold of the controllable valve, increase an opening size of the controllable valve, decrease an opening size of the controllable valve, or alter a permeability or porosity of the controllable valve.

In an aspect, at least one of the one or more supplement reservoirs 1712 is adapted to contain one or more breast milk supplements. In an aspect, at least one of the one or more breast milk supplements includes a lipid, a protein, an oligosaccharide, a fatty acid, a carbohydrate, or a nucleotide, or any combination thereof. In an aspect, at least one of the one or more breast milk supplements includes a nutrient, a micronutrient, a vitamin, an amino acid, or a mineral. In an aspect, at least one of the one or more breast milk supplements includes a therapeutic agent, an antimicrobial agent, a prebiotic, or a probiotic. In an aspect, at least one of the one or more breast milk supplements includes an appetite stimulator or an appetite suppressant. In an aspect, at least one of the one or more breast milk supplements includes a flavoring. In an aspect, the flavoring includes a flavoring preferred by an infant. In an aspect, the flavoring includes a flavoring associated with a specific food type, the flavoring intended to acclimate an infant to the specific food type. Non-limiting examples of breast milk supplements including flavorings have been described above herein.

Housing 1710 of breast milk supplement delivery device 1700 includes data storage component 1716. In an aspect, data storage component 1716 is incorporated into the control unit 1718. For example, the data storage component can include a memory component of the control unit. In an aspect, data storage component 1716 includes a removable data storage component. For example, the data storage component can include a removable memory stick or flash drive. Non-limiting aspects of a data storage component have been described above herein.

Data storage component 1716 includes a breast milk supplement regimen. In an aspect, the breast milk supplement regimen includes a personalized breast milk supplement regimen. For example, the breast milk supplement regimen can be personalized for a specific subject with specific nutritional needs. For example, the breast milk supplement regimen can be personalized for a subset of subjects with common nutritional and/or medical needs.

In an aspect, the breast milk supplement regimen is personalized for an infant. For example, the breast milk supplement regimen can be personalized for a specific infant based on the nutritional and/or medical need of the specific infant. In an aspect, the breast milk supplement regimen is personalized based on attributes of an infant. In an aspect, the breast milk supplement regimen is personalized based on at least one of age, weight, gender, genome, ethnicity, medical condition, or nutritional need of the infant. For example, the breast milk supplement regimen can be personalized for a premature infant. For example, the breast milk supplement regimen can be personalized for an infant failing to thrive.

In an aspect, the breast milk supplement regimen is personalized for the lactating female. In an aspect, the breast milk supplement regimen is personalized based on a quality of breast milk of the lactating female. For example, the breast milk supplement regimen can include one or more breast milk supplements, e.g., micronutrients or minerals, deficient in the breast milk of the lactating female. In an aspect, the breast milk supplement regimen is personalized based on a nutritional quality of the breast milk of the lactating female. In an aspect, the breast milk supplement regimen is personalized based on a microbial quality of the breast milk of the lactating female. In an aspect, the breast milk supplement regimen is personalized based on an immunological quality of the breast milk of the lactating female.

In an aspect, the breast milk supplement regimen is adjustable. In an aspect, the breast milk supplement regimen is adjustable based on a change in at least one of an attribute of an infant and/or a quality of breast milk of the lactating female. For example, the infant's nutritional needs may change as the infant ages and/or gains weight. For example, the quality of the breast milk of the lactating female may change in response to changing the female's diet or treating a medical condition.

Breast milk supplement delivery device includes control unit 1718 operably coupled to data storage component 1716 and to the controllable valve 1714 of the at least one of the one or more supplement reservoirs 1712. Control unit 1718 includes a microprocessor and circuitry. In an aspect, the circuitry includes circuitry configured to actuate the controllable valve 1714 of at least one of the one or more supplement reservoirs 1712 based on the breast milk supplement regimen. Non-limiting aspects of a control unit have been described above herein. In an aspect, the circuitry of control unit 1718 includes one or more instructions for operating the breast milk supplement delivery device.

Returning to FIGS. 17A and 17B, the at least one delivery tube 1720 includes a second end 1724 configured for placement in proximity to nipple 1740 of a lactating female. In an aspect, the second end 1724 of the at least one delivery tube 1720 includes an adhesive on a surface conforming to a surface in proximity to the nipple. For example, the second end of the at least one delivery tube can include a region including a pressure sensitive adhesive which when pressed on the skin in proximity to the nipple adheres the second end of the at least one delivery tube to the skin. In an aspect, a strip of tape or other piece of adhesive material is used to adhere the second end of the at least one delivery tube in position in proximity to the nipple of the lactating female.

In some embodiments, the second end 1724 of the at least one delivery tube 1720 configured for placement in proximity to the nipple 1740 includes at least one analyte sensor. In an aspect, the breast milk supplement delivery device includes at least one analyte sensor associated with the second end of the at least one delivery tube, the at least one analyte sensor configured for placement in proximity to the nipple. In an aspect, the at least one analyte sensor includes at least one of a saliva analyte sensor, a breast milk analyte sensor, and/or an exhaled breath analyte sensor. In an aspect, the at least one analyte sensor is configured to sense at least one analyte in at least one of the infant's saliva, the infant's exhaled breath, and/or the lactating female's breast milk. In an aspect, the at least one analyte sensor is operably coupled to control unit 1718, the control unit including circuitry configured to receive sensed analyte information from the at least one analyte sensor and to actuate the controllable valve 1714 of at least one of the one or more supplement reservoirs 1712 in response to the received sensed analyte information.

In an aspect, breast milk supplement delivery device 1700 includes at least one delivery event sensor. In an aspect, the at least one delivery event sensor includes at least one of a flow sensor, a pressure sensor, a strain sensor, or a weight sensor. In an aspect, the at least one delivery event sensor includes at least one of a conductivity sensor, an acoustic sensor, an optical transmission sensor, or a clock. For example, the at least one delivery event sensor can include a flow sensor that detects flow of the one or more breast milk supplements through at least one of the port, the controllable valve, or the delivery tube. In an aspect, the at least one delivery event sensor senses that one or more breast milk supplements have been delivered based on fluid flow and or changes in the volume within the one or more supplement reservoirs. In an aspect, the control unit 1718 includes delivery event circuitry configured to receive information associated with a delivery event from at least one delivery event sensor. In an aspect, the delivery event circuitry includes circuitry configured to receive information associated with at least one of a breast milk supplement type, an infant identifier, a dosage, a time, or a date.

In an aspect, breast milk supplement delivery device 1700 includes reporting circuitry configured to report a delivery event. In an aspect, the reporting circuitry includes circuitry configured to report the delivery event through at least one of a radiofrequency transmission, a radiofrequency identification (RFID) transmission, an optical transmission, or an audio transmission. In an aspect, the reporting circuitry includes circuitry configured to report the delivery event through at least one of an electrical wire, an optical fiber, or a removable storage medium. In an aspect, the reporting circuitry includes circuitry configured to report at least one of a breast milk supplement type, a dosage, an infant identifier, a time, or a date. In an aspect, the reporting circuitry includes circuitry configured to report the delivery event to a computing device. In an aspect, the reporting circuitry includes circuitry configured to report the delivery event to a personal electronic device. In an aspect, the reporting circuitry includes circuitry configured to report the delivery event to a user interface.

In an aspect, breast milk supplement delivery device 1700 includes a user interface. In an aspect, the user interface is positioned on an outer surface of the housing 1710. In an aspect, the user interface is configured to transmit information to a user, e.g., alert messages, instructions, and/or information associated with a delivery event. In an aspect, the user interface is configured to receive information from a user, e.g., infant attributes, quality of breast milk, infant identifier, breast milk supplement regimen, operating parameters, and the like. In an aspect, the user interface includes a display. For example, the user interface can include a display (e.g., a touchscreen display, a light-emitting diode (LED) display, or a liquid crystal display (LCD)) including a keypad or touchpad. In an aspect, the user interface includes at least one of a haptic or audio interface. For example, the user interface can include a haptic interface (e.g., a vibratory motor) and/or a haptic actuator (e.g., electroactive polymers, or piezoelectric, electrostatic, or subsonic audio wave surface actuators). For example, the user interface can include an audio interface including a microphone and speakers. In an aspect, user interface includes at least one optical indicator, e.g., a green and/or a red light.

In an aspect, the user interface is integrated into the housing of the breast milk supplement delivery device or optionally may be one or more peripheral devices operably connected through a wired or wireless connection to the housing of the breast milk supplement delivery device. Non-limiting examples of input components include a graphical user interface, a display, a keyboard, a keypad, a touch-screen, a microphone, a stylus pend, a switch, a dial, a button, or the like. Other non-limiting examples of input components include a trackball, a joystick, a mouse, an image scanner, a digital camera, a webcam, a light pen, a bar code reader, a fingerprint scanner, a retinal scanner, or a game pad.

In an aspect, the user interface includes one or more output components over which processed information is transmitted, e.g., viewed, as output results and may be integrated into the housing of the breast milk supplement delivery device or may be one or more peripheral devices operably connected through a wired or wireless connection to the housing of the breast milk supplement delivery device. For example, the user interface may be used to report to a user information associated with a delivery event. For example, the user interface may be used to report to a user information associated with a sensed analyte, e.g., a sensed saliva analyte, exhaled breath analyte, and/or breast milk analyte. Non-limiting examples of output components include but are not limited to displays, e.g., liquid crystal displays, audio speakers, and the like.

In an aspect, breast milk supplement delivery device 1700 includes a transmission unit including circuitry and at least one antenna. In an aspect, the transmission unit is operably coupled to the control unit. In an aspect, the transmission unit is incorporated into the control unit. In an aspect, the transmission unit includes at least one transmitter and at least one receiver. In an aspect, the transmission unit includes at least one of a radiofrequency transmission unit, a radiofrequency identification (RFID) transmission unit, an optical transmission unit, or an audio transmission unit. In an aspect, the transmission unit is configured to transmit one or more signals having information associated with a delivery event.

In an aspect, breast milk supplement delivery device 1700 includes at least one power source. For example, the at least one power source can include one or more batteries, e.g., AAA batteries. Other non-limiting examples of power sources have been described above herein.

In an aspect, breast milk supplement delivery device 1700 includes an infant presence detector. In an aspect, the infant presence detector is configured to detect the presence or absence of an infant in proximity to breast milk supplement delivery device 1700, and to provide an infant presence signal to the control unit. In an aspect, the actuation circuitry of the control unit is configured to actuate the controllable valve of the at least one of the one or more supplement reservoirs based on the infant presence signal. For example, the actuation circuitry can be configured to only actuate the controllable valve when the infant is in proper proximity to the breast milk supplement delivery device. In an aspect, the infant presence detector includes at least one of a temperature sensor, a pressure sensor, an electrical conductivity sensor, a radar sensor, an ultrasonic sensor, a microphone, a camera, a photodetector, or a strain sensor. Non-limiting examples of infant presence detectors have been described above herein.

In some embodiments, breast milk supplement delivery device 1700 includes a temperature control component configured to control a temperature of at least one of the one or more supplement reservoirs. For example, the temperature control component can heat the contents of at least one of the one or more supplement reservoirs for the comfort of a nursing infant.

In some embodiments, a breast milk supplement delivery device includes a housing including one or more supplement reservoirs, at least one of the one or more supplement reservoirs including a port with a controllable valve; and a control unit including a microprocessor and circuitry, the control unit operably coupled to the controllable valve of the at least one of the one or more supplement reservoirs, the circuitry including actuation circuitry configured to actuate the controllable valve of the at least one of the one or more supplement reservoirs; a flexible delivery tube including a first end and a second end, the first end of the flexible delivery tube in fluid communication with the port, the second end of the flexible delivery tube configured for placement in proximity a nipple of a lactating female; and at least one analyte sensor associated with the second end of the flexible delivery tube and operably coupled to the control unit.

Figure 18A:
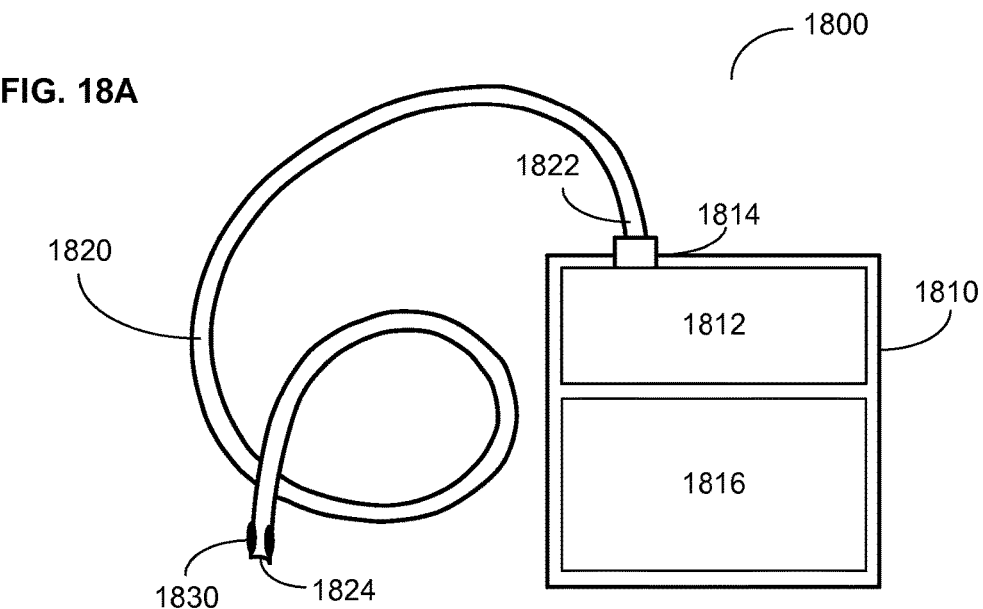
FIG. 18A illustrates an embodiment of a breast milk supplement delivery device including a housing and a flexible delivery tube with at least one analyte sensor.
Figure 18B:
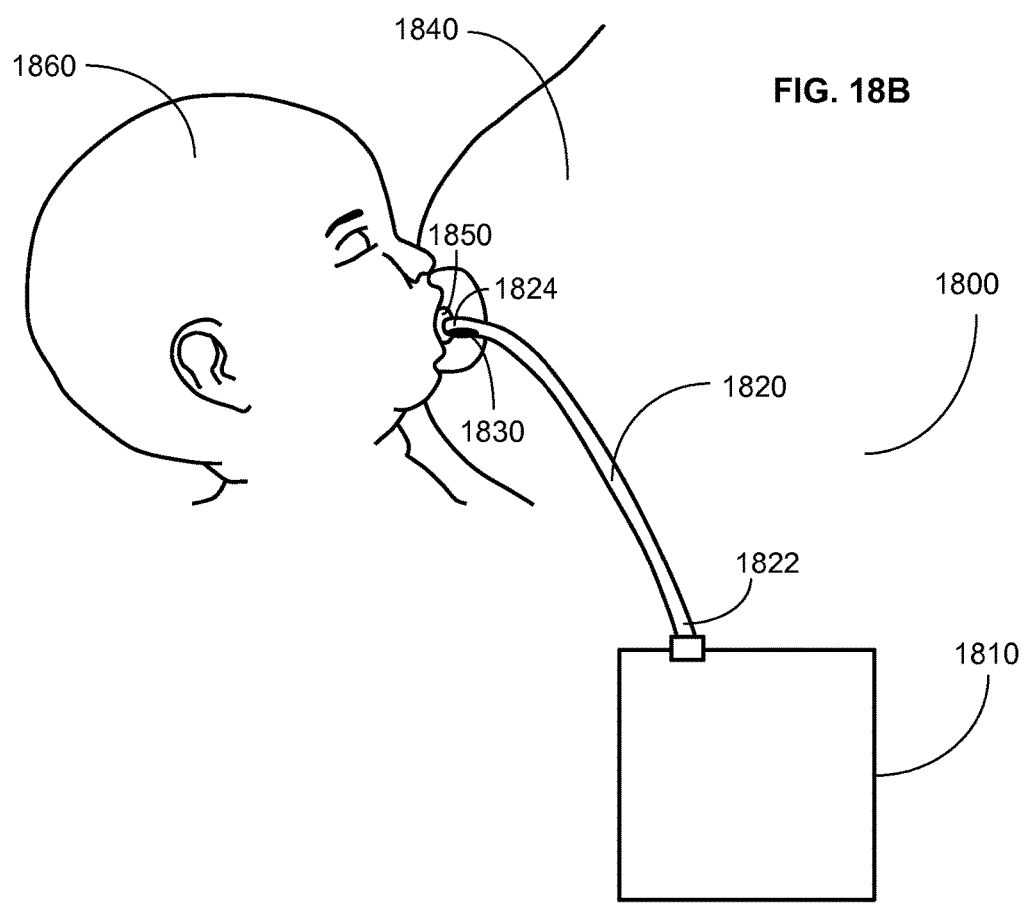
FIG. 18B shows placement of an embodiment of a breast milk supplement delivery device such as shown in FIG. 18A in proximity to the nipple of a lactating female.

FIGS. 18A and 18B illustrate aspects of a breast milk supplement delivery device including a housing, a flexible delivery tube, and at least one analyte sensor associated with the flexible delivery tube. FIG. 18A illustrates aspects of breast milk supplement delivery device 1800. Breast milk supplement delivery device 1800 includes a housing 1810. Housing 1810 includes one or more supplement reservoirs 1812, at least one of the one or more supplement reservoirs including a port with a controllable valve 1814; and control unit 1816. Breast milk supplement delivery device 1800 includes flexible delivery tube 1820 having a first end 1822 and a second end 1824, the first end 1822 of the flexible delivery tube 1820 is in fluid communication with the port with the controllable valve 1814. Breast milk supplement delivery device 1800 includes at least one analyte sensor 1830 associated with the second end 1824 of the flexible delivery tube 1820. FIG. 18B illustrates further aspects of breast milk supplement delivery device 1800. Breast milk supplement delivery device 1800 is shown including housing 1810 and flexible delivery tube 1820 including at least one analyte sensor 1830. Housing 1810 is shown near a breast region 1840 of a lactating female. The flexible delivery tube 1820 is shown attached at a first end 1822 to at least one port with a controllable valve associated with housing 1810. A second end 1824 of the flexible delivery tube 1820 including at least one analyte sensor 1830 is shown in close proximity to a nipple 1850 of the lactating female. Also shown is a nursing infant 1860. The second end 1824 of the flexible delivery tube 1820 is in a position to deliver one or more breast milk supplements to the nursing infant 1860. The at least one analyte sensor 1830 at the second end 1824 of the flexible delivery tube 1820 is in a position to sense at least one analyte, e.g., at least one saliva analyte, at least one exhaled breath analyte, and/or at least one breast milk analyte.

Breast milk supplement delivery device 1800 includes a housing 1810. In an aspect, the housing is sized for placement on the body of the lactating female. For example, the housing can be sized for placement on the chest, torso, waist, arm, or leg region of the lactating female. In an aspect, the housing is sized for placement on a furniture surface near a breast region of the lactating female. For example, the housing can be sized for placement on a chair, a sofa, a bed, or a table. In some embodiments, the housing is sized for placement on the ground. For example, a breast milk supplement delivery device for use with animals, e.g., domesticated or captive animals, can include a housing sized for placement on the ground in the vicinity of the animal.

In an aspect, housing 1810 comprises a wearable housing. In an aspect, housing 1810 includes an adhesive on at least one surface conforming to the surface near a breast region of the lactating female. For example, one surface of the housing can include a pressure sensitive adhesive that allows the housing to be reversibly adhered to a body portion, e.g., a breast, chest, torso, arm, or leg, of the lactating female. In an aspect, housing 1810 includes one or more straps, the one or more straps sized to extend around a body portion of the lactating female. For example, the housing can include a strap that allows the housing to be hung from the neck of the lactating female. For example, the housing can include one or more straps to strap the housing to the chest, torso, arm, or leg of the lactating female. In an aspect, housing 1810 is sized for at least one of placement in an article of clothing or placement on an article of clothing. For example, housing 1810 can be sized for placement into a nursing bra or nursing shirt. For example, housing 1810 can be sized for placement in a pair of pants, e.g., in the waistband of the pair of pants.

Housing 1810 includes one or more supplement reservoirs 1812, at least one of the one or more supplement reservoirs 1812 including a port with a controllable valve 1814. In an aspect, the controllable valve 1814 includes at least one of a pneumatic valve, a solenoid valve, a poppet valve, a diaphragm valve, a piezoelectric valve, or a pinch valve. In an aspect, the controllable valve 1814 includes an actuator, the actuator operably coupled to actuation circuitry. In an aspect, the actuator includes at least one of a pneumatic actuator, a hydraulic actuator, a magnetic actuator, or an electric actuator. For example, the controllable valve can include a solenoid valve including an electric actuator that at least partially opens and closes in response to an electrical signal generated by the actuation circuitry. In an aspect, the actuation circuitry includes circuitry configured to at least partially open or close the controllable valve. In an aspect, the actuation circuitry is to at least one of open the controllable valve, close the controllable valve, change a pressure threshold of the controllable valve, increase an opening size of the controllable valve, decrease an opening size of the controllable valve, or alter a permeability or porosity of the controllable valve.

In an aspect, at least one of the one or more supplement reservoirs 1812 is adapted to contain one or more breast milk supplements. In an aspect, at least one of the one or more breast milk supplements includes a lipid, a protein, an oligosaccharide, a fatty acid, a carbohydrate, or a nucleotide, or any combination thereof. In an aspect, at least one of the one or more breast milk supplements includes a nutrient, a micronutrient, a vitamin, an amino acid, or a mineral. In an aspect, at least one of the one or more breast milk supplements includes a therapeutic agent, an antimicrobial agent, a prebiotic, or a probiotic. In an aspect, at least one of the one or more breast milk supplements includes an appetite stimulator or an appetite suppressant. In an aspect, at least one of the one or more breast milk supplements includes a flavoring. In an aspect, the flavoring includes a flavoring preferred by an infant. In an aspect, the flavoring includes a flavoring associated with a specific food type, the flavoring intended to acclimate an infant to the specific food type. Non-limiting examples of breast milk supplements including flavorings have been described above herein.

Breast milk supplement delivery device 1800 includes control unit 1816. Control unit 1816 includes a microprocessor and circuitry. Control unit 1816 is operably coupled to controllable valve 1814 and to the at least one analyte sensor 1830. In an aspect, the circuitry of control unit 1816 includes actuation circuitry configured to actuate the controllable valve 1814 of the at least one of the one or more supplement reservoirs 1812. In an aspect, the actuation circuitry includes circuitry configured to actuate the controllable valve 1814 of the at least one of the one or more supplement reservoirs in response to sensed analyte information. In an aspect, the circuitry of computer component 1816 includes one or more instructions for operating the breast milk supplement delivery device. Non-limiting aspects of a control unit have been described above herein.

Returning to FIGS. 18A and 18B, the flexible delivery tube 1820 includes a second end 1824 configured for placement in proximity to nipple 1850 of a lactating female. In an aspect, the second end 1824 of the flexible delivery tube 1820 includes an adhesive on a surface conforming to a surface in the proximity of the nipple of the lactating female. For example, the second end of the flexible delivery tube can include a region including a pressure sensitive adhesive which when pressed on the skin in proximity to the nipple adheres the second end of the flexible delivery tube to the skin. In an aspect, a strip of tape or other piece of adhesive material is used to adhere the second end of the flexible delivery tube in position in proximity to the nipple of the lactating female.

Breast milk supplement delivery device 1800 includes at least one analyte sensor 1830 associated with the second end 1824 of the flexible delivery tube 1820 and operably coupled to control unit 1816. In some embodiments, the at least one analyte sensor 1830 at the second end 1824 of the flexible delivery tube 1820 is configured for placement in proximity to the nipple 1850 of a lactating female. In an aspect, the at least one analyte sensor 1830 associated with the second end 1824 of the flexible delivery tube 1820 includes a saliva analyte sensor. In an aspect, the at least one analyte sensor 1830 associated with the second end 1824 of the flexible delivery tube 1820 includes a breast milk analyte sensor. In an aspect, the at least one analyte sensor 1830 associated with the second end 1824 of the flexible delivery tube 1820 includes an exhaled breath analyte sensor. In an aspect, the at least one analyte sensor 1830 is configured to sense at least one of a lipid, a protein, an oligosaccharide, a fatty acid, a carbohydrate, or a nucleotide, or any combination thereof. In an aspect, the at least one analyte sensor 1830 is configured to sense at least one of a nutrient, a micronutrient, a vitamin, an amino acid, or a mineral. In an aspect, the at least one analyte sensor 1830 is configured to sense a microorganism. Non-limiting examples of an analyte sensor have been described above herein. In an aspect, the control unit 1816 includes circuitry configured to receive sensed analyte information from the at least one analyte sensor 1830. In an aspect, the actuation circuitry includes circuitry configured to actuate the controllable valve 1814 of the at least one of the one or more supplement reservoirs 1812 in response to sensed analyte information.

In an aspect, breast milk supplement delivery device 1800 includes a data storage component. In an aspect, the data storage component is incorporated into control unit 1816. In an aspect, the data storage component comprises a removable data storage component. Non-limiting examples of a data storage component have been described above herein. In an aspect, the data storage component includes a stored breast milk supplement regimen. In an aspect, the stored breast milk supplement regimen is adjustable in response to sensed analyte information. For example, the stored breast milk supplement regimen can be adjusted in response to one or more analytes sensed in an infant's saliva or exhaled breath or in a lactating female's breast milk. In an aspect, the actuation circuitry includes circuitry configured to actuate the controllable valve 1814 of at least one of the one or more supplement reservoirs 1812 based on the stored breast milk supplement regimen.

In an aspect, breast milk supplement delivery device 1800 includes at least one delivery event sensor. In an aspect, the at least one delivery event sensor includes at least one of a flow sensor, a pressure sensor, a strain sensor, or a weight sensor. In an aspect, the at least one delivery event sensor includes at least one of a conductivity sensor, an acoustic sensor, an optical transmission sensor, or a clock. In an aspect, the at least one delivery event sensor senses that one or more breast milk supplements have been delivered based on fluid flow and or changes in the volume within the one or more supplement reservoirs. In an aspect, control unit 1816 includes delivery event circuitry configured to receive information associated with a delivery event from at least one delivery event sensor. In an aspect, the delivery event circuitry includes circuitry configured to receive information associated with at least one of a breast milk supplement type, an infant identifier, a dosage, a time, or a date.

In an aspect, breast milk supplement delivery device 1800 includes reporting circuitry configured to report a delivery event. In an aspect, the reporting circuitry includes circuitry configured to report the delivery event through at least one of a radiofrequency transmission, a radiofrequency identification (RFID) transmission, an optical transmission, or an audio transmission. In an aspect, the reporting circuitry includes circuitry configured to report the delivery event through at least one of an electrical wire, an optical fiber, or a removable storage medium. In an aspect, the reporting circuitry includes circuitry configured to report at least one of a sensed analyte, a breast milk supplement type, a dosage, an infant identifier, a time, or a date. In an aspect, the reporting circuitry includes circuitry configured to report the delivery event to a computing device. In an aspect, the reporting circuitry includes circuitry configured to report the delivery event to a personal electronic device. In an aspect, the reporting circuitry includes circuitry configured to report the delivery event to a user interface.

In an aspect, breast milk supplement delivery device 1800 includes a user interface. In an aspect, the user interface is positioned on an outer surface of the housing 1810 and operably coupled to the control unit 1816. Non-limiting examples of a user interface have been described above herein.

In an aspect, breast milk supplement delivery device 1800 includes a transmission unit including circuitry and at least one antenna. In an aspect, the transmission unit is operably coupled to the control unit. In an aspect, the transmission unit includes at least one transmitter and at least one receiver. In an aspect, the transmission unit includes at least one of a radiofrequency transmission unit, a radiofrequency identification (RFID) transmission unit, an optical transmission unit, or an audio transmission unit. In an aspect, the transmission unit is configured to transmit one or more signals having information associated with a delivery event.

In an aspect, breast milk supplement delivery device 1800 includes at least one power source. For example, the at least one power source can include one or more batteries, e.g., AAA batteries. Other non-limiting examples of power sources have been described above herein.

In an aspect, breast milk supplement delivery device 1800 includes an infant presence detector. In an aspect, the infant presence detector is configured to detect the presence or absence of an infant in proximity to breast milk supplement delivery device 1700, and to provide an infant presence signal to the control unit. In an aspect, the actuation circuitry of the control unit is configured to actuate the controllable valve of the at least one of the one or more supplement reservoirs based on the infant presence signal. In an aspect, the infant presence detector includes at least one of a temperature sensor, a pressure sensor, an electrical conductivity sensor, a radar sensor, an ultrasonic sensor, a microphone, a camera, a photodetector, or a strain sensor. Non-limiting examples of an infant presence detector have been described above herein.

In some embodiments, breast milk supplement delivery device 1700 includes a temperature control component. In an aspect, the temperature control component is configured to control a temperature of at least one of the one or more supplement reservoirs. For example, the temperature control component can heat the contents of at least one of the one or more supplement reservoirs for the comfort of a nursing infant.

Figure 19A:
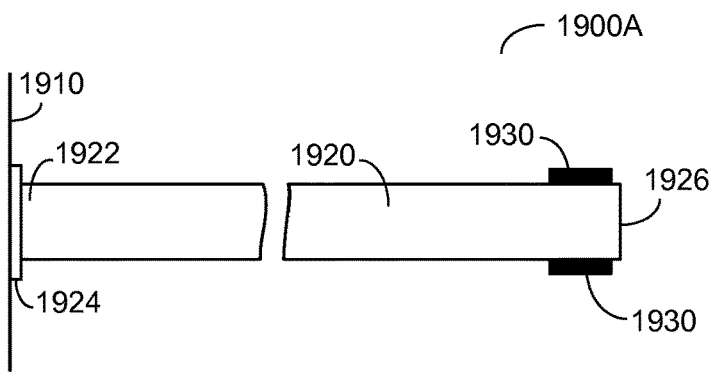
FIG. 19A illustrates a cross-section through a portion of an embodiment of a breast milk supplement delivery device including a flexible delivery tube and at least one analyte sensor.
Figure 19B:
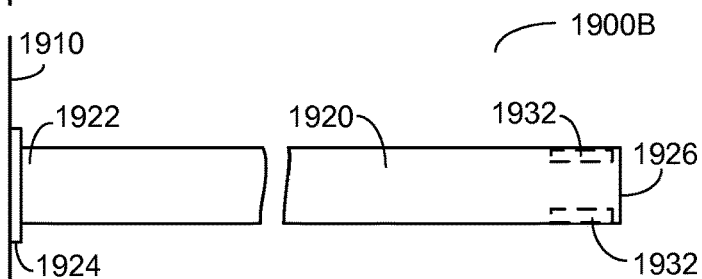
FIG. 19B illustrates a cross-section through a portion of an embodiment of a breast milk supplement delivery device including a flexible delivery tube and at least one analyte sensor.
Figure 19C:
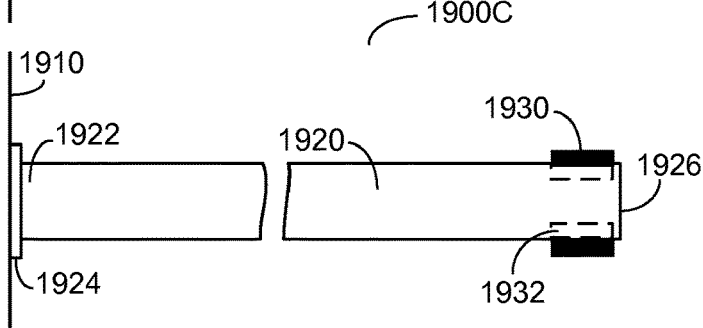
FIG. 19C illustrates a cross-section through a portion of an embodiment of a breast milk supplement delivery device including a flexible delivery tube and at least one analyte sensor.

FIGS. 19A-19E illustrate non-limiting aspects of a breast milk supplement delivery device including at least one analyte sensor such as shown in FIGS. 18A and 18B. FIG. 19A shows a portion of breast milk supplement delivery device 1900A including housing 1910 and flexible delivery tube 1920. Flexible delivery tube 1920 includes a first end 1922 in fluid communication with port 1924 and a second end 1926 including at least one analyte sensor 1930. In this non-limiting example, the at least one analyte sensor 1930 is positioned on an exterior surface of the flexible delivery tube 1920. FIG. 19B shows a portion of breast milk supplement delivery device 1900B including housing 1910 and flexible delivery tube 1920. Flexible delivery tube 1920 includes a first end 1922 in fluid communication with port 1924 and a second end 1926 including at least one analyte sensor 1932. In this non-limiting example, the at least one analyte sensor 1932 is position on an interior surface of the flexible delivery tube 1920. FIG. 19C shows a portion of breast milk supplement delivery device 1900C including housing 1910 and flexible delivery tube 1920. Flexible delivery tube 1920 includes a first end 1922 in fluid communication with port 1924 and a second end 1926 including at least one analyte sensor 1930 positioned on an exterior surface of the flexible delivery tube 1920 and at least one analyte sensor 1932 positioned on an interior surface of the flexible delivery tube 1920.

Figure 19D:
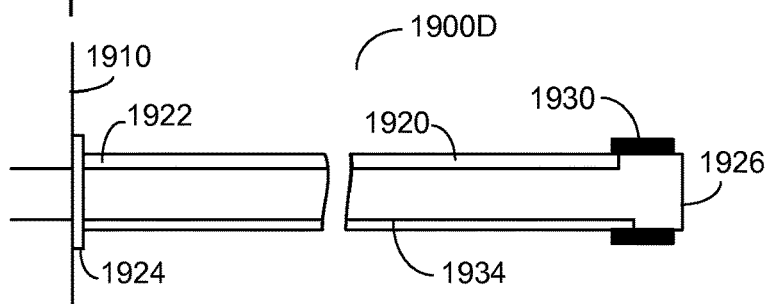
FIG. 19D illustrates a cross-section through a portion of an embodiment of a breast milk supplement delivery device including a flexible delivery tube and at least one analyte sensor.

In an aspect, the at least one analyte sensor transmits sensed analyte information to the control unit of the breast milk supplement delivery device. FIG. 19D illustrates an embodiment of transmitting sensed analyte information. FIG. 19D shows a portion of breast milk supplement delivery device 1900D including housing 1910 and flexible delivery tube 1920. Flexible delivery tube 1920 includes a first end 1922 in fluid communication with port 1924 and a second end 1926 including at least one analyte sensor 1930 positioned on an exterior surface of the flexible delivery tube 1920. At least one analyte sensor 1930 is operably connected to the control unit associated with housing 1910 through one or more wires 1934. In an aspect, the one or more wires 1934 extend along the exterior surface of the flexible delivery tube 1920. In an aspect, the one or more wires 1934 are integrated into the wall of the flexible delivery tube 1920. In an aspect, the one or more wires 1934 extend along the interior surface of the flexible delivery tube 1920. Information regarding at least one sensed analyte is transmitted along the one or more wires 1934 from the at least one sensor 1930 to the control unit in housing 1910.

Figure 19E:
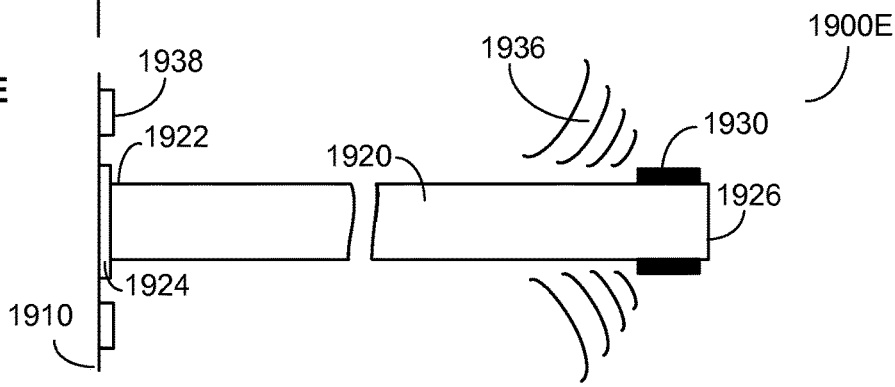
FIG. 19E illustrates a cross-section through a portion of an embodiment of a breast milk supplement delivery device including a flexible delivery tube and at least one analyte sensor.

FIG. 19E illustrates an embodiment of transmitting sensed analyte. FIG. 19E shows a portion of breast milk supplement delivery device 1900E including housing 1910 and flexible delivery tube 1920. Flexible delivery tube 1920 includes a first end 1922 in fluid communication with port 1924 and a second end 1926 including at least one analyte sensor 1930 positioned on an exterior surface of flexible delivery tube 1920. At least one analyte sensor 1930 is operably connected to the control unit associated with housing 1910 through a one or more wireless signals 1936. The housing 1910 includes at least one antenna 1938 as part of a transmission unit. The transmission unit is operably coupled to the control unit in housing 1910. Information regarding at least one sensed analyte is transmitted through the one or more wireless signals 1936 from the at least one sensor 1930 to the at least one antenna 1938 and from there to the control unit in housing 1910.

In some embodiments, a breast milk supplement delivery device includes a nipple component sized for placement in an infant's mouth, the nipple component having a first end and a second end, the first end of the nipple component including an aperture; a guard component attached to the second end of the nipple component; a supplement reservoir including a port with a controllable valve, the supplement reservoir adapted to contain one or more breast milk supplements; a flow conduit disposed within at least a portion of the nipple component, a first end of the flow conduit in fluid communication with the aperture on the first end of the nipple component and a second end of the flow conduit in fluid communication with the port of the supplement reservoir; a data storage component including a breast milk supplement regimen; and a control unit including a microprocessor and circuitry, the control unit operably coupled to the controllable valve and to the data storage component, the circuitry including actuation circuitry configured to actuate the controllable valve to modulate release of the one or more breast milk supplements from the supplement reservoir based on the breast milk supplement regimen.

Figure 20A:
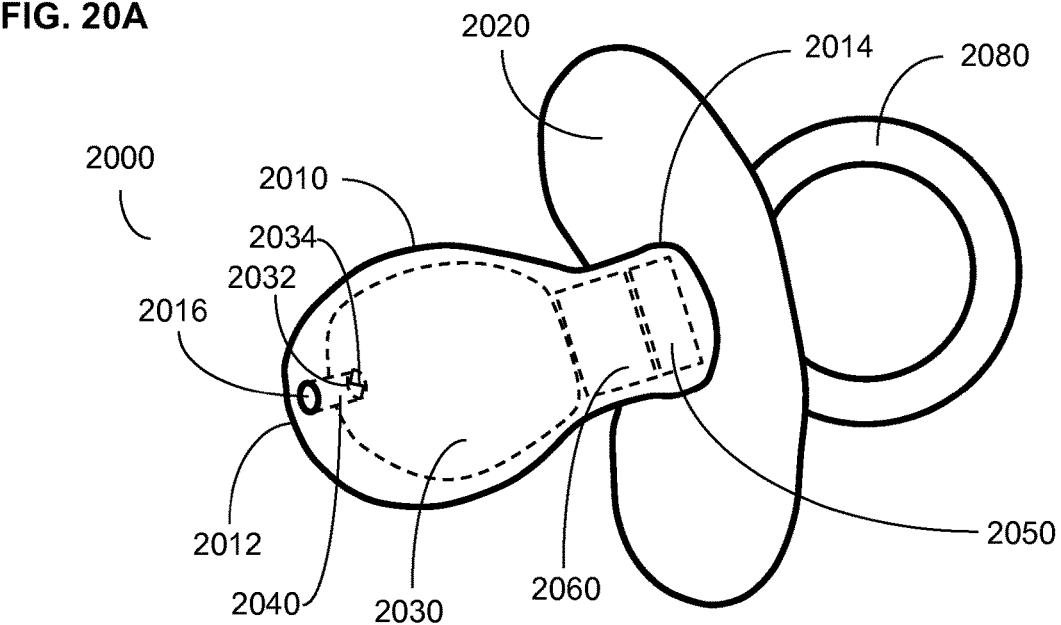
FIG. 20A illustrates an embodiment of a breast milk supplement delivery device.
Figure 20B:
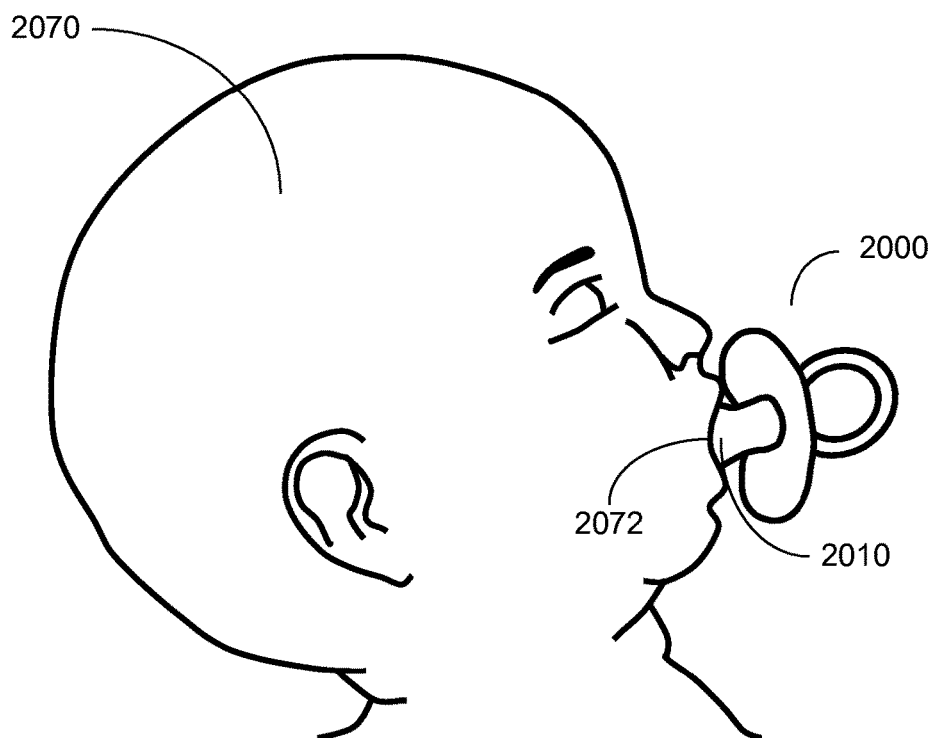
FIG. 20B illustrates placement of an embodiment of a breast milk supplement delivery device such as shown in FIG. 20A in the mouth of an infant.

FIGS. 20A and 20B illustrate aspects of an embodiment of a breast milk supplement delivery device. FIG. 20A shows breast milk supplement delivery device 2000 including nipple component 2010. Nipple component 2010 has a first end 2012 and a second end 2014, the first end 2012 including an aperture 2016. Guard component 2020 is attached to the second end 2014 of nipple component 2010. Breast milk supplement delivery device 2000 includes a supplement reservoir 2030 including a port 2032 with a controllable valve 2034. Supplement reservoir 2030 is adapted to contain one or more breast milk supplements. Flow conduit 2040 is shown disposed within at least a portion of nipple component 2010, a first end of the flow conduit in fluid communication with the aperture 2016 and a second end of the flow conduit in fluid communication with the port 2032 of the supplement reservoir 2030. Breast milk supplement delivery device 2000 includes data storage component 2050 including a breast milk supplement regimen and control unit 2060 including a microprocessor and circuitry. Control unit 2060 is operably coupled to the controllable valve 2034 and to the data storage component 2050. The circuitry of control unit 2060 includes actuation circuitry configured to actuate the controllable valve 2034 to modulate release of the one or more breast milk supplements based on the breast milk supplement regimen. In this non-limiting embodiment, breast milk supplement delivery device further includes a handle component 2080 attached to at least one of the nipple component 2010 and the guard component 2020. FIG. 20B shows breast milk supplement delivery device 2000 in use with infant 2070. The nipple component 2010 is sized for placement in an infant 2070 mouth 2072. As infant 2070 suckles on the nipple component 2010, the breast milk supplement delivery device 2000 is configured to controllably delivery one or more breast milk supplements to the infant 2070 according to the breast milk supplement regimen stored in the data storage component of the breast milk supplement delivery device 2000.

Breast milk supplement delivery device 2000 includes a nipple component 2010 sized for placement in an infant's mouth. In an aspect, the size of the nipple component varies depending upon the age of the infant. For example, the nipple component may come in small (six months or younger), medium (six to 18 months), or large (18 months and older) sizes. In an aspect, the nipple component is formed from a flexible material. In an aspect, the nipple component is formed from silicone. In an aspect, the nipple component is formed from latex. In an aspect, the nipple component is formed from rubber. In an aspect, the nipple component is formed from hard plastic. In an aspect, the nipple component is hollow. For example, the nipple component may consist of a silicone or latex wall defining a hollow space into which other components of the breast milk supplement delivery device are placed. For example, the supplement reservoir, the data storage component, and/or the control unit may all be sized to fit within a hollow space of the nipple component.

Breast milk supplement delivery device 2000 includes guard 2020. Guard 2020 is configured to prevent the infant from drawing the nipple component 2010 too far into his/her mouth. In an aspect, the guard is about 1.5 to 2 inches across. The guard may be formed from hard plastic or latex. In an aspect, the guard includes one or more ventilation holes. For example, the guard can include one or more ventilation holes to allow air to circulate between the guard and the infant's face. In an aspect, the nipple component and the guard component comprise a one-piece unit. For example, the nipple component and the guard component may be constructed as part of a one-piece unit designed to prevent a choking risk due to detachment of the nipple component from the guard component Breast milk supplement delivery device 2000 includes supplement reservoir 2020. In an aspect, the supplement reservoir is at least partially disposed in at least one of the nipple component and the guard component. In an aspect, the supplement reservoir is completely disposed in either the nipple component or the guard component. In an aspect, the supplement reservoir is attached to an exterior portion of the nipple component and/or the guard component, with a flow conduit attached to the supplement reservoir and extending towards the first end of the nipple component. In an aspect, the flow conduit attached to the exterior positioned supplement reservoir extends along an outer surface of the nipple component. In an aspect, the flow conduit attached to the exterior positioned supplement reservoir at least partially extends through the interior of the nipple component.

Supplement reservoir 2020 includes a port with a controllable valve. In an aspect, the controllable valve is formed from at least one of an electroactive material, a stimulus responsive hydrogel, or a shape-memory alloy. In an aspect, the controllable valve is a piezoelectric valve. In an aspect, the controllable valve includes at least one of a pneumatic valve, a solenoid valve, a poppet valve, a diaphragm valve, or a pinch valve. In an aspect, the controllable valve includes an actuator, the actuator operably coupled to the actuation circuitry. In an aspect, the actuator includes at least one of a pneumatic actuator, a hydraulic actuator, a magnetic actuator, or an electric actuator.

Supplement reservoir 2020 is adapted to contain one or more breast milk supplements. In an aspect, at least one of the one or more breast milk supplements includes a lipid, a protein, an oligosaccharide, a fatty acid, a carbohydrate, or a nucleotide, or any combination thereof. In an aspect, at least one of the one or more breast milk supplements includes a nutrient, a micronutrient, a vitamin, an amino acid, or a mineral. In an aspect, at least one of the one or more breast milk supplements includes a therapeutic agent, an antimicrobial agent, a prebiotic, or a probiotic. In an aspect, at least one of the one or more breast milk supplements includes an appetite stimulator or an appetite suppressant. In an aspect, at least one of the one or more breast milk supplements includes a flavoring. In an aspect, the flavoring includes a flavoring preferred by an infant. In an aspect, the flavoring includes a flavoring associated with a specific food type, the flavoring intended to acclimate an infant to the specific food type. Non-limiting examples of breast milk supplements including flavorings have been described above herein.

In an aspect, a breast milk supplement delivery device includes two or more supplement reservoirs, each of the two or more supplement reservoirs including a port with a controllable valve. In an aspect, the port is in fluid communication with the flow conduit. In an aspect, each of the two or more supplement reservoirs is adapted to contain the same one or more breast milk supplements. In an aspect, each of the two or more supplement reservoirs is adapted to contain different one or more breast milk supplements. In an aspect, each of the two or more supplement reservoirs is attached through a port to a flow conduit, each of the flow conduits in fluid communication with an aperture defined by a wall of the nipple component.

Breast milk supplement delivery device 2000 includes a flow conduit 2040 disposed within at least a portion of the nipple component. The flow conduit, e.g., a tube, is in fluid communication with an aperture in the nipple component and a port associated with the supplement reservoir. In response to actuation of the controllable valve of the port, fluid containing one or more breast milk supplements is able to flow from the supplement reservoir, through the flow conduit, and out the aperture at the end of the nipple component. In an aspect, a breast milk supplement delivery device includes two or more flow conduits, a first end of each of the two or more flow conduits in fluid communication with at least one aperture on the first end of the nipple component, a second end of each of the two or more flow conduits in fluid communication with a port associated with a supplement reservoir.

Breast milk supplement delivery device 2000 includes data storage component 2050 operably coupled to control unit 2060. In an aspect, data storage component 2050 is incorporated into control unit 2060. For example, the data storage component can include a memory component of the control unit. In an aspect, data storage component 2050 includes a removable data storage component. For example, the data storage component can include a removable memory card or stick. Non-limiting aspects of a data storage component have been described above herein. In an aspect, the data storage component 2050 and the control unit 2060 are at least partially disposed in at least one of the nipple component 2010 and the guard component 2020. In an aspect, the data storage component 2050 is at least partially disposed in the nipple component 2010 and/or the guard component 2020. In an aspect, the control unit 2060 is at least partially disposed in the nipple component 2010 and/or the guard component 2020. In an aspect, the data storage component 2050 and/or the control unit 2060 is attached to an exterior surface of the nipple component 2010 and/or the guard component 2020. In an aspect, the data storage component 2050 and/or the control unit 2060 is incorporated into the wall of the nipple component and/or guard component. For example, a microprocessor and circuitry including data storage and control capacity can be embedded and/or printed onto a surface of the nipple component and/or the guard component.

Data storage component 2050 includes a breast milk supplement regimen. In an aspect, the breast milk supplement regimen includes a systematic or regulated plan for delivery of one or more breast milk supplements to a nursing infant. In an aspect, the breast milk supplement regimen includes one or more types of breast milk supplements and dosing and timing of said breast milk supplements. In an aspect, the breast milk supplement regimen includes a personalized breast milk supplement regimen. For example, the breast milk supplement regimen can be personalized for a specific subject with specific nutritional needs. For example, the breast milk supplement regimen can be personalized for a subset of subjects with common nutritional and/or medical need.

In an aspect, the breast milk supplement regimen is personalized for the infant. In an aspect, the breast milk supplement regimen is personalized for at least one attribute of the infant. In an aspect, the breast milk supplement regimen is personalized for at least one of age, weight, gender, genome, ethnicity, medical condition, or nutritional need of the infant.

In an aspect, the breast milk supplement regimen is personalized for a lactating female. In an aspect, the breast milk supplement regimen is personalized for a quality of breast milk of the lactating female. In an aspect, the breast milk supplement regimen is personalized for at least one of a nutritional quality, a microbial quality, or an immunological quality of the breast milk of the lactating female.

In an aspect, the breast milk supplement regimen is adjustable. In an aspect, the breast milk supplement regimen is adjustable based on a change in at least one of an attribute of the infant and/or a quality of breast milk of a lactating female. For example, the infant's nutritional needs may change as the infant ages and/or gains weight. For example, the quality of the breast milk of the lactating female may change in response to changing the female's diet or treating a medical condition.

Breast milk supplement delivery device 2000 includes control unit 2060 operably coupled to data storage component 2050 and to the controllable valve 2034 of the supplement reservoirs 2030. Control unit 2060 includes a microprocessor and circuitry. In an aspect, the circuitry includes actuation circuitry configured to actuate the controllable valve 2034 to modulate release of the one or more breast milk supplements from the supplement reservoir based on the breast milk supplement regimen. Non-limiting aspects of a control unit have been described above herein. In an aspect, the circuitry of control unit 2060 includes one or more instructions for operating breast milk supplement delivery device 2000.

In an aspect, breast milk supplement delivery device 2000 includes at least one delivery event sensor. In an aspect, the at least one delivery event sensor includes at least one of a flow sensor, a pressure sensor, a strain sensor, or a weight sensor. In an aspect, the at least one delivery event sensor includes at least one of a conductivity sensor, an acoustic sensor, an optical transmission sensor, or a clock. In an aspect, the at least one delivery event sensor senses that one or more breast milk supplements have been delivered based on fluid flow and or changes in the volume within the supplement reservoir. In an aspect, the control unit includes delivery event circuitry configured to receive information associated with a delivery event. In an aspect, the delivery event circuitry includes circuitry configured to receive information associated with at least one of a breast milk supplement type, an infant identifier, a dosage, a time, or a date. In an aspect, the delivery event circuitry includes circuitry configured to receive information associated with a delivery event from at least one delivery event sensor.

In an aspect, breast milk supplement delivery device 2000 includes reporting circuitry configured to report a delivery event. In an aspect, the reporting circuitry includes circuitry configured to report the delivery event through at least one of a radiofrequency transmission, a radiofrequency identification (RFID) transmission, an optical transmission, or an audio transmission. In an aspect, the reporting circuitry includes circuitry configured to report the delivery event through at least one of an electrical wire, an optical fiber, or a removable storage medium. In an aspect, the reporting circuitry includes circuitry configured to report at least one of a breast milk supplement type, a dosage, an infant identifier, a time, or a date. In an aspect, the reporting circuitry includes circuitry configured to report the delivery event to a computing device. In an aspect, the reporting circuitry includes circuitry configured to report the delivery event to a personal electronic device.

In an aspect, breast milk supplement delivery device 2000 includes a transmission unit including circuitry and at least one antenna. In an aspect, the transmission unit is attached to at least one of the nipple component 2010, the guard component 2020, and/or the handle component 2080 of breast milk supplement delivery device 2000. In an aspect, the transmission unit is operably coupled to control unit 2060. In an aspect, the transmission unit is incorporated into control unit 2060. In an aspect, the transmission unit includes at least one transmitter and at least one receiver. In an aspect, the transmission unit includes at least one of a radiofrequency transmission unit, a radiofrequency identification (RFID) transmission unit, an optical transmission unit, or an audio transmission unit. In an aspect, the transmission unit is configured to transmit one or more signals having information associated with a delivery event.

In an aspect, breast milk supplement delivery device 2000 includes at least one power source. For example, the at least one power source can include one or more batteries, e.g., AAA batteries. Other non-limiting examples of power sources have been described above herein.

In some embodiments, breast milk supplement delivery device 2000 includes at least one analyte sensor operably coupled to control unit 2060, the at least one analyte sensor configured to sense at least one analyte. In an aspect, the at least one analyte sensor is associated with at least one surface of the nipple component 2010. In an aspect, the at least one analyte sensor is associated with an outer surface of the guard component 2020. In an aspect, the at least one analyte sensor comprises at least one of a saliva analyte sensor or an exhaled breath analyte sensor. In an aspect, the at least one analyte sensor is operably coupled to control unit 2060, the control unit 2060 including circuitry configured to receive information associated with the at least one analyte from the at least one analyte sensor, and to actuate the controllable valve 2034 of the supplement reservoir 2030 in response to the received information associated with the at least one analyte. In an aspect, the control unit includes circuitry configured to adjust the breast milk supplement regimen based on the received information associated with the at least one analyte.

In an aspect, breast milk supplement delivery device 2000 includes an infant presence detector. In an aspect, the infant presence detector is configured to detect the presence or absence of an infant in proximity to breast milk supplement delivery device 2000, and to provide an infant presence signal to the control unit. In an aspect, the actuation circuitry includes circuitry configured to actuate the controllable valve of the supplement reservoir based on the infant presence signal. In an aspect, the infant presence detector includes at least one of a temperature sensor, a pressure sensor, an electrical conductivity sensor, a radar sensor, an ultrasonic sensor, a microphone, a camera, a photodetector, or a strain sensor. Non-limiting examples of an infant presence detector have been described above herein.

In some embodiments, breast milk supplement delivery device 2000 includes a temperature control component configured to control a temperature of at least a portion of the nipple component and the one or more supplement reservoirs. For example, the temperature control component can heat the contents of at least one of the one or more supplement reservoirs for the comfort of a nursing infant.

In some embodiments, a breast milk supplement delivery device includes a nipple component sized for placement in an infant's mouth, the nipple component having a first end and a second end, the first end of the nipple component including an aperture; a guard component attached to the second end of the nipple component; a supplement reservoir including a port with a controllable valve, the supplement reservoir adapted to contain one or more breast milk supplements; a flow conduit disposed within at least a portion of the nipple component, a first end of the flow conduit in fluid communication with the aperture on the first end of the nipple component and a second end of the flow conduit in fluid communication with the port of the supplement reservoir; one or more analyte sensors associated with at least one of the nipple component and the guard component; and a control unit including a microprocessor and circuitry, the control unit operably coupled to the controllable valve and to the one or more analyte sensors, the circuitry including actuation circuitry configured to actuate the controllable valve.

Figure 21A:
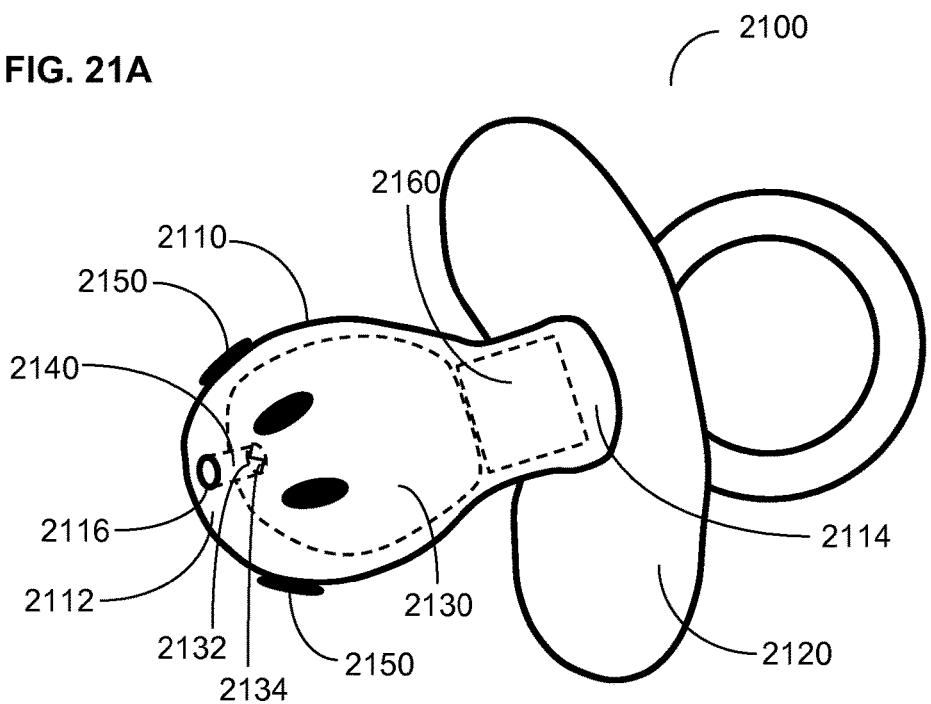
FIG. 21A illustrates an embodiment of a breast milk supplement delivery device having one or more analyte sensors.
Figure 21B:
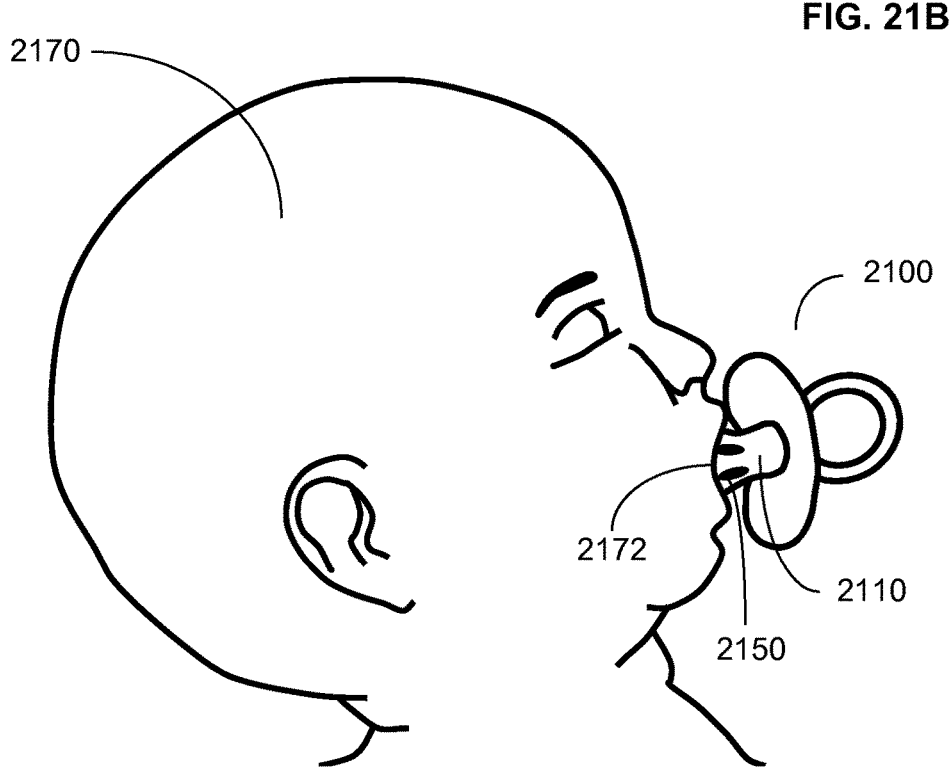
FIG. 21B illustrates placement of an embodiment of a breast milk supplement delivery device such as shown in FIG. 20A in the mouth of an infant.

FIGS. 21A and 21B illustrate an embodiment of a breast milk supplement delivery device including one or more analyte sensors. FIG. 21A shows breast milk supplement delivery device 2100 including nipple component 2110 and guard component 2120. Nipple component 2110 has a first end 2112 and a second end 2114. The first end 2112 of nipple component 2110 includes an aperture 2116. Guard component 2120 is attached to the second end 2114 of nipple component 2110. Breast milk supplement delivery device 2100 includes supplement reservoir 2130 including a port 2132 with a controllable valve 2134. Supplement reservoir 2130 is adapted to contain one or more breast milk supplements. A flow conduit 2140 is disposed within at least a portion of nipple component 2110. A first end of flow conduit 2140 is in fluid communication with aperture 2116 on the first end 2112 of nipple component 2110. A second end of flow conduit 2140 is in fluid communication with the port 2132 of supplement reservoir 2130. Breast milk supplement delivery device 2100 includes one or more analyte sensors 2150 shown in this non-limiting example associated with nipple component 2110. Breast milk supplement delivery device 2100 includes control unit 2160. Control unit 2160 includes a microprocessor and circuitry and is operably coupled to the controllable valve 2134 and to the one or more analyte sensors 2150. The circuitry includes actuation circuitry configured to actuate the controllable valve 2134. In an aspect, control unit 2160 includes circuitry configured to receive sensed analyte information from at least one of the one or more analyte sensors 2150. In an aspect, the actuation circuitry includes circuitry configured to actuate the controllable valve 2134 of the supplement reservoir 2130 in response to sensed analyte information. In an aspect, control unit 2160 includes circuitry configured to receive information associated with at least one analyte from at least one of the one or more analyte sensors 2150 and to actuate the controllable valve 2134 to modulate release of the one or more breast milk supplements from supplement reservoir 2130 in response to the received information associated with the at least one analyte.

FIG. 21B illustrates further aspects of breast milk supplement delivery device 2100. Breast milk supplement delivery device 2100 includes a nipple component 2110 sized for placement in an infant 2070 mouth 2172. As infant 2170 suckles on the nipple component 2110, the breast milk supplement delivery device 2100 is configured to sense at least one analyte, e.g., at least one saliva or exhaled breath analyte, with the one or more analyte sensors 2150 and to controllably deliver one or more breast milk supplements to the infant 2170 based on the sensed at least one analyte.

Breast milk supplement delivery device 2100 includes one or more analyte sensors 2150. In an aspect, at least one of the one or more analyte sensors includes a saliva analyte sensor. For example, the breast milk supplement delivery device can include at least one saliva analyte sensor configured to sense at least one saliva analyte in the infant's saliva. In an aspect, at least one of the one or more analyte sensors includes an exhaled breath analyte sensor. For example, the breast milk supplement delivery device can include at least one exhaled breath analyte sensor configured to sense at least one exhaled breath analyte in the infant's exhaled breath. In an aspect, at least one of the one or more analyte sensors is configured to sense at least one of a lipid, a protein, an oligosaccharide, a fatty acid, a carbohydrate, or a nucleotide, or any combination thereof. In an aspect, at least one of the one or more analyte sensors is configured to sense at least one of a nutrient, a micronutrient, a vitamin, an amino acid, or a mineral. In an aspect, at least one of the one or more analyte sensors is configured to sense a microorganism. Non-limiting examples of an analyte sensor have been described above herein.

In some embodiments, such as shown in FIGS. 21A and 21B, the one or more analyte sensors are associated with the nipple component of the breast milk supplement delivery device. In an aspect, the one or more analyte sensors are attached to a surface of a nipple. In an aspect, the one or more analyte sensors are attached to an external surface of the nipple component. For example, the one or more analyte sensors can be attached to the outer surface of the nipple component of the breast milk supplement delivery device and in direct contact with an infant's saliva during suckling. In an aspect, the one or more analyte sensors are attached to an internal surface of the nipple component. For example, the one or more analyte sensors can be associated with a portion of the aperture and/or the flow conduit. For example, the one or more analyte sensors can be associated with an inner wall of a nipple component formed from a permeable or semi-permeable material through which saliva and/or exhaled breath analytes are able to diffuse. In an aspect, the one or more analyte sensors are embedded in the material forming the nipple component.

Figure 22:
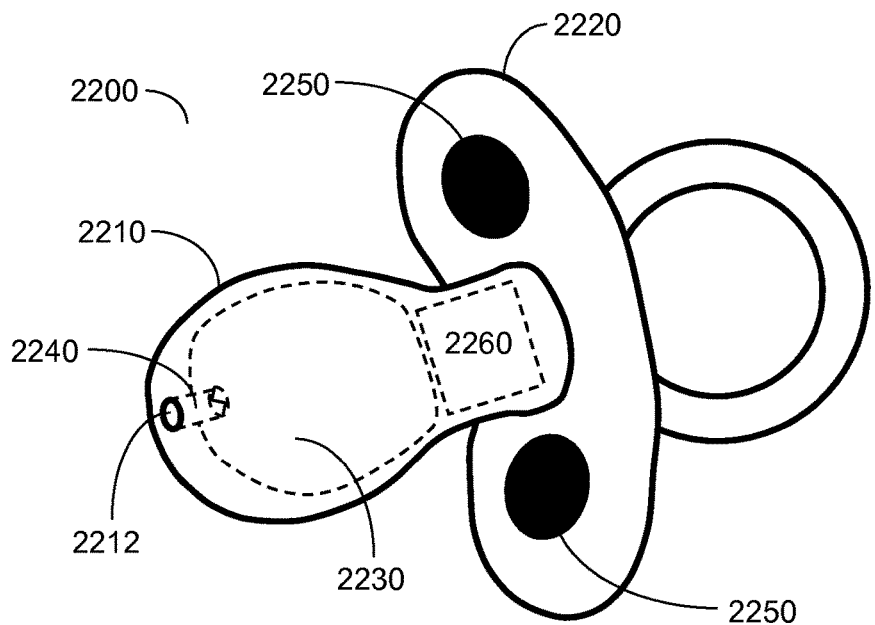
FIG. 22 illustrates an embodiment of a breast milk supplement delivery device having one or more analyte sensors.

In some embodiments, a breast milk supplement delivery device includes one or more analyte sensors associated with a guard component of the device. FIG. 22 illustrates an embodiment of a breast milk supplement delivery device including one or more analyte sensors associated with the guard component. Breast milk supplement delivery device 2200 includes nipple component 2210 and guard component 2220. Nipple component 2210 is sized for placement in an infant's mouth. Nipple component 2210 includes a first end and a second end, the first end including an aperture 2212. Guard component 2220 is attached to the second end of nipple component 2210. Breast milk supplement delivery device 2200 includes supplement reservoir 2230 including a port with a controllable valve. Supplement reservoir 2230 is adapted to contain one or more breast milk supplements. A flow conduit 2240 is disposed within at least a portion of nipple component 2210. A first end of flow conduit 2240 is in fluid communication with aperture 2212. A second end of flow conduit 2240 is in fluid communication with the port of supplement reservoir 2230. Breast milk supplement delivery device 2200 includes one or more analyte sensors 2250 associated with guard component 2220. A control unit 2260 includes a microprocessor and circuitry. Control unit 2260 is operably coupled to the controllable valve and to the one or more analyte sensors 2250. The circuitry includes actuation circuitry configured to actuate the controllable valve.

In an aspect, the one or more analyte sensors 2250 are associated with a surface of guard component 2220. In an aspect, the one or more analyte sensors are associated with an outer surface of the guard component. In an aspect, the one or more analyte sensors are associated with a surface of the guard component facing the infant. In an aspect, the one or more analyte sensors are associated with one or more ventilation holes defined by the guard component. For example, the one or more analyte sensors can be associated with the walls of the ventilation holes defined by the guard component such that exhaled breath analytes passing through the ventilation holes are detected by the analyte sensors. In an aspect, the one or more analyte sensors are incorporated in to a meshwork spanning the one or more ventilation holes.

Figure 23:
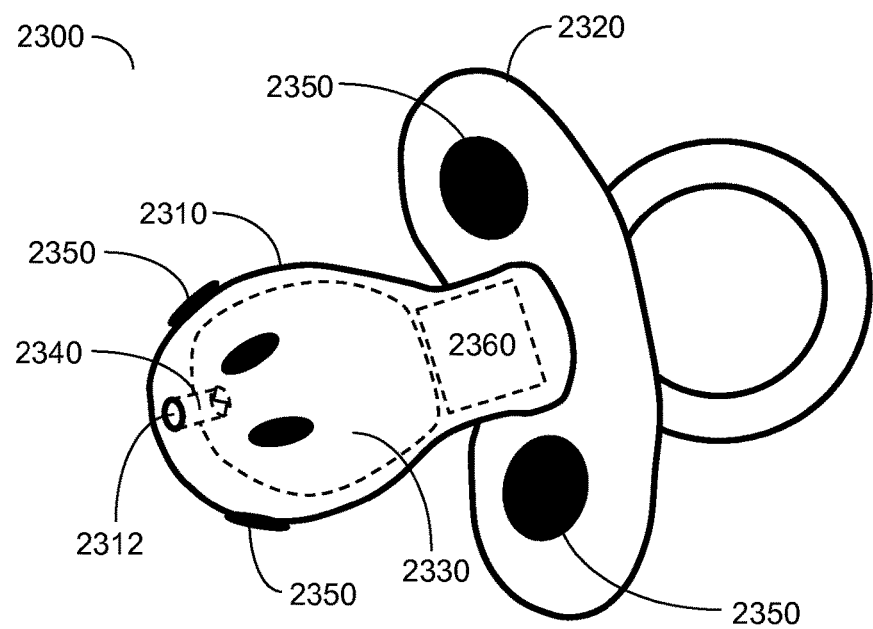
FIG. 23 illustrates an embodiment of a breast milk supplement delivery device having one or more analyte sensors.

In some embodiments, a breast milk supplement delivery device includes one or more analyte sensors associated with a nipple component of the device and one or more analyte sensors associated with a guard component of the device. FIG. 23 illustrates an embodiment of a breast milk supplement delivery device including one or more analyte sensors associated with both the nipple and guard components. Breast milk supplement delivery device 2300 includes nipple component 2310 and guard component 2320. Nipple component 2310 is sized for placement in an infant's mouth. Nipple component 2310 includes a first end and a second end, the first end including an aperture 2312. Guard component 2320 is attached to the second end of nipple component 2310. Breast milk supplement delivery device 2300 includes supplement reservoir 2330 including a port with a controllable valve. Supplement reservoir 2330 is adapted to contain one or more breast milk supplements. A flow conduit 2340 is disposed within at least a portion of nipple component 2310. A first end of flow conduit 2340 is in fluid communication with aperture 2312. A second end of flow conduit 2340 is in fluid communication with the port of supplement reservoir 2330. Breast milk supplement delivery device 2300 includes one or more analyte sensors 2350 associated with nipple component 2310 and one or more analyte sensors 2350 associated with guard component 2320. A control unit 2360 includes a microprocessor and circuitry. Control unit 2360 is operably coupled to the controllable valve and to the one or more analyte sensors 2350. The circuitry includes actuation circuitry configured to actuate the controllable valve.

In an aspect, each of the one or more analyte sensors 2350 associated with the nipple component 2310 and each of the one or more analyte sensors 2350 associated with the guard component 2320 are identical. In an aspect, the one or more analyte sensors 2350 associated with the nipple component 2310 include saliva analyte sensors which the one or more analyte sensors 2350 associated with the guard component include exhaled breath analyte sensors.

Embodiments of a breast milk supplement delivery device such as shown in FIGS. 21A and 21B, 22, and 23, include a nipple component sized for placement in an infant's mouth. In an aspect, the size of the nipple component varies depending upon the age of the infant. For example, the nipple component may come in small (six months or younger), medium (six to 18 months), or large (18 months and older) sizes. In an aspect, the nipple component is formed from a flexible material. In an aspect, the nipple component is formed from at least one of silicone, latex, rubber, or hard plastic. In an aspect, the nipple component is hollow. For example, the nipple component may consist of a silicone or latex wall defining a hollow space into which other components of the breast milk supplement delivery device are placed. For example, the supplement reservoir, the data storage component, and/or the control unit may all be sized to fit within a hollow space of the nipple component.

Embodiments of a breast milk supplement delivery device such as shown in FIGS. 21A and 21B, 22, and 23, include a guard component. In an aspect, the guard component is configured to prevent the infant from drawing the nipple component too far into his/her mouth. In an aspect, the guard is about 1.5 to 2 inches across. The guard may be formed from hard plastic or latex. In an aspect, the guard includes one or more ventilation holes. For example, the guard can include one or more ventilation holes to allow air to circulate between the guard and the infant's face. In an aspect, the nipple component and the guard component comprise a one-piece unit.

Embodiments of a breast milk supplement delivery device such as shown in FIGS. 21A and 21B, 22, and 23, include a supplement reservoir. In an aspect, the supplement reservoir is at least partially disposed in at least one of the nipple component and the guard component. In an aspect, the supplement reservoir is completely disposed in either the nipple component or the guard component. In an aspect, the supplement reservoir is attached to an exterior portion of the nipple component and/or the guard component, with a flow conduit attached to the supplement reservoir and extending towards the first end of the nipple component. In an aspect, the flow conduit attached to the exterior positioned supplement reservoir extends along an outer surface of the nipple component. In an aspect, the flow conduit attached to the exterior positioned supplement reservoir at least partially extends through the interior of the nipple component.

The supplement reservoir includes a port with a controllable valve. In an aspect, the controllable valve is formed from at least one of an electroactive material, a stimulus-responsive hydrogel, or a shape-memory allow. In an aspect, the controllable valve includes a piezoelectric valve. In an aspect, the controllable valve includes at least one of a pneumatic valve, a solenoid valve, a poppet valve, a diaphragm valve, or a pinch valve. In an aspect, the controllable valve includes an actuator, the actuator operably coupled to the actuation circuitry. In an aspect, the actuator includes at least one of a pneumatic actuator, a hydraulic actuator, a magnetic actuator, or an electric actuator.

The supplement reservoir is adapted to contain one or more breast milk supplements. In an aspect, at least one of the one or more breast milk supplements includes a lipid, a protein, an oligosaccharide, a fatty acid, a carbohydrate, or a nucleotide, or any combination thereof. In an aspect, at least one of the one or more breast milk supplements includes a nutrient, a micronutrient, a vitamin, an amino acid, or a mineral. In an aspect, at least one of the one or more breast milk supplements includes a therapeutic agent, an antimicrobial agent, a prebiotic, or a probiotic. In an aspect, at least one of the one or more breast milk supplements includes an appetite stimulator or an appetite suppressant. In an aspect, at least one of the one or more breast milk supplements includes a flavoring. In an aspect, the flavoring includes a flavoring preferred by an infant. In an aspect, the flavoring includes a flavoring associated with a specific food type, the flavoring intended to acclimate the infant to the specific food type. Non-limiting examples of breast milk supplements have been described above herein.

In an embodiment, a breast milk supplement delivery device includes two or more supplement reservoirs, each of the two or more supplement reservoirs including a port with a controllable valve. In an aspect, each of the two or more supplement reservoirs are at least partially disposed in at least one of the nipple component and the guard component. In an aspect, at least one of the two or more supplement reservoirs is attached to an external surface of at least one of the nipple component and the guard component. In an aspect, each of the two or more supplement reservoirs is adapted to contain the same one or more breast milk supplements. In an aspect, each of the two or more supplement reservoirs is adapted to contain different one or more breast milk supplements. In an aspect, each of the two or more supplement reservoirs is attached through a port to a flow conduit, each of the flow conduits in fluid communication with an aperture defined by a wall of the nipple component.

Embodiments of a breast milk supplement delivery device such as shown in FIGS. 21A and 21B, 22, and 23, include a flow conduit disposed within at least a portion of the nipple component. The flow conduit, e.g., a tube, is in fluid communication with an aperture in the nipple component and a port associated with the supplement reservoir. In response to actuation of the controllable valve of the port, fluid containing one or more breast milk supplements is able to flow from the supplement reservoir, through the flow conduit, and out the aperture at the end of the nipple component. In an aspect, a breast milk supplement delivery device includes two or more flow conduits, a first end of each of the two or more flow conduits in fluid communication with at least one aperture on the first end of the nipple component, a second end of each of the two or more flow conduits in fluid communication with a port associated with a supplement reservoir.

Embodiments of a breast milk supplement delivery device such as shown in FIGS. 21A and 21B, 22, and 23, include a control unit operably coupled to the controllable valve of the supplement reservoir and to the one or more analyte sensors. The control unit includes a microprocessor and circuitry. In an aspect, the control unit is at least partially disposed in at least one of the nipple component and/or the guard component. In an aspect, the control unit is attached to an exterior surface of the nipple component and/or the guard component. In an aspect, the control unit is incorporated into the wall of the nipple component and/or guard component. For example, a microprocessor and circuitry including data storage and control capacity can be embedded and/or printed onto a surface of the nipple component and/or the guard component.

Embodiments of a breast milk supplement delivery device such as shown in FIGS. 21A and 21B, 22, and 23, includes a control unit included circuitry including actuation circuitry. In an aspect, the control unit includes circuitry configured to receive sensed analyte information from at least one of the one or more analyte sensors. In an aspect, the actuation circuitry includes circuitry configured to actuate the controllable valve of the supplement reservoir in response to sensed analyte information. For example, the actuation circuitry may actuate the controllable valve to at least partially open or close in response to sensed analyte information. In an aspect, the control unit includes circuitry configured to receive information associated with at least one analyte from at least one of the one or more analyte sensors and to actuate the controllable valve to modulate release of the one or more breast milk supplements from the supplement reservoir in response to the received information associated with the at least one analyte. For example, the sensed analyte information may indicate a lack of a specific nutrient or micronutrient in the saliva of the infant, causing the actuation circuitry to trigger the controllable valve to release said nutrient or micronutrient from the supplement reservoir. Non-limiting aspects of a control unit have been described above herein. In an aspect, the circuitry of control unit includes one or more instructions for operating the breast milk supplement delivery device.

In some embodiments, a breast milk supplement delivery device such as described in FIGS. 21A and 21B, 22, and 23 includes at least one delivery event sensor. In an aspect, the at least one delivery event sensor includes at least one of a flow sensor, a pressure sensor, a strain sensor, or a weight sensor. In an aspect, the at least one delivery event sensor includes at least one of a conductivity sensor, an acoustic sensor, an optical transmission sensor, or a clock. In an aspect, the at least one delivery event sensor senses that one or more breast milk supplements have been delivered based on fluid flow and or changes in the volume within the supplement reservoir. In an aspect, the control unit includes delivery event circuitry configured to receive information associated with a delivery event. In an aspect, the delivery event circuitry includes circuitry configured to receive information associated with at least one of a breast milk supplement type, an infant identifier, a dosage, a time, or a date. In an aspect, the delivery event circuitry includes circuitry configured to receive information associated with a delivery event from at least one delivery event sensor.

In some embodiments, a breast milk supplement delivery device such as described in FIGS. 21A and 21B, 22, and 23 includes reporting circuitry configured to report a delivery event. In an aspect, the control unit includes reporting circuitry configured to report a delivery event. In an aspect, the reporting circuitry includes circuitry configured to report the delivery event through at least one of a radiofrequency transmission, a radiofrequency identification (RFID) transmission, an optical transmission, or an audio transmission. In an aspect, the reporting circuitry includes circuitry configured to report the delivery event through at least one of an electrical wire, an optical fiber, or a removable storage medium. In an aspect, the reporting circuitry includes circuitry configured to report at least one of information associated with a sensed analyte, a breast milk supplement type, a dosage, an infant identifier, a time, or a date. In an aspect, the reporting circuitry includes circuitry configured to report the delivery event to a computing device. In an aspect, the reporting circuitry includes circuitry configured to report the delivery event to a personal electronic device.

In some embodiments, a breast milk supplement delivery device such as described in FIGS. 21A and 21B, 22, and 23 includes a transmission unit including circuitry and at least one antenna. In an aspect, the transmission unit is operably coupled to the control unit. In an aspect, the transmission unit is incorporated into the control unit. In an aspect, the transmission unit includes at least one transmitter and at least one receiver. In an aspect, the transmission unit includes at least one of a radiofrequency transmission unit, a radiofrequency identification (RFID) transmission unit, an optical transmission unit, or an audio transmission unit. In an aspect, the transmission unit is configured to transmit one or more signals having information associated with a delivery event.

In some embodiments, a breast milk supplement delivery device such as described in FIGS. 21A and 21B, 22, and 23 includes a data storage component including a breast milk supplement regimen. In an aspect, the data storage component is operably coupled to the control unit. In an aspect, data storage component is incorporated into control unit. In an aspect, data storage component includes a removable data storage component. Non-limiting aspects of a data storage component have been described above herein. In an aspect, the data storage component is at least partially disposed in the nipple component and/or the guard component. In an aspect, the data storage component is attached to an exterior surface of the nipple component and/or the guard component. In an aspect, the data storage component is incorporated into the wall of the nipple component and/or guard component.

In an aspect, the data storage component includes a breast milk supplement regimen. Non-limiting aspects of a breast milk supplement regimen have been described above herein.

In an aspect, the actuation circuitry includes circuitry configured to actuate the controllable valve of the supplement reservoir based on the breast milk supplement regimen. In an aspect, the control unit includes circuitry configured to update the breast milk supplement regimen in response to sensed analyte information received from the one or more analyte sensors.

In some embodiments, a breast milk supplement delivery device such as described in FIGS. 21A and 21B, 22, and 23 includes an infant presence detector. In an aspect, the infant presence detector is configured to detect the presence or absence of the infant in proximity to the breast milk supplement delivery device, and to provide an infant presence signal to the control unit. In an aspect, the actuation circuitry includes circuitry configured to actuate the controllable valve of the supplement reservoir based on the infant presence signal. In an aspect, the infant presence detector includes at least one of a temperature sensor, a pressure sensor, an electrical conductivity sensor, a radar sensor, an ultrasonic sensor, a microphone, a camera, a photodetector, and/or a strain sensor. Non-limiting examples of an infant presence detector have been described above herein.

In some embodiments, a breast milk supplement delivery device such as described in FIGS. 21A and 21B, 22, and 23 includes a temperature control component. In an aspect, the temperature control component is configured to control a temperature of at least a portion of the nipple component and the one or more supplement reservoirs. For example, the temperature control component can heat the contents of at least one of the one or more supplement reservoirs for the comfort of a nursing infant.

Figure 24:
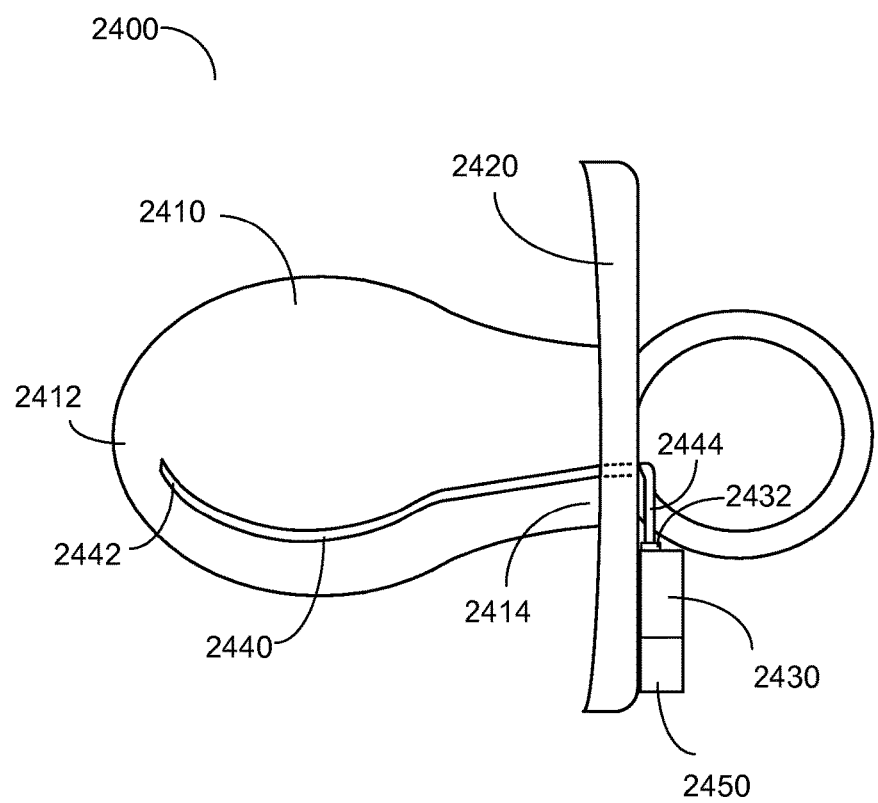
FIG. 24 illustrates an embodiment of a breast milk supplement delivery device having an external flow conduit.

FIG. 24 shows a side view of an embodiment of a breast milk supplement delivery device including an externally placed flow conduit. Breast milk supplement delivery device 2400 includes a nipple component 2410 having a first end 2412 and a second end 2414, the first end 2412 sized for placement in an infant's mouth; a guard component 2420 attached to the second end 2414 of the nipple component 2410; a supplement reservoir 2430 including a port 2432 with a controllable valve, the supplement reservoir 2430 adapted to contain one or more breast milk supplements; a flow conduit 2440 including a first end 2442 and a second end 2444, the first end 2442 of the flow conduit 2440 positioned proximal to the first end 2412 of the nipple component 2410, the second end 2444 in fluid communication with the port 2432 of the supplement reservoir 2430; and a control unit 2450 including a microprocessor and circuitry, the control unit operably coupled to the controllable valve, the circuitry including actuation circuitry configured to actuate the controllable valve. In an aspect, the breast milk supplement delivery device 2400 includes a data storage component including a breast milk supplement regimen. In an aspect, the breast milk supplement delivery device 2400 includes one or more analyte sensors configured to sense at least one analyte. In an aspect, breast milk supplement delivery device 2400 includes a delivery event sensor and delivery event circuitry. In an aspect, breast milk supplement delivery device 2400 includes reporting circuitry configure to report a delivery event. In an aspect, breast milk supplement delivery device 2400 includes a transmission unit. In an aspect, breast milk supplement delivery device 2400 includes an infant presence detector. In an aspect, breast milk supplement delivery device 2400 includes a temperature control component.

In an aspect, a breast milk supplement delivery system includes a delivery unit including a nipple component sized for placement in an infant's mouth, the nipple component having a first end and a second end, the first end of the nipple component including an aperture, a guard component attached to the second end of the nipple component; a supplement reservoir including a port with a controllable valve, the supplement reservoir adapted to contain one or more breast milk supplements; and a flow conduit disposed within at least a portion of the nipple component, a first end of the flow conduit in fluid communication with the aperture on the first end of the nipple component and a second end of the flow conduit in fluid communication with the port of the supplement reservoir; a breast milk supplement regimen; and a control unit including a microprocessor and circuitry, the control unit including actuation circuitry configured to wirelessly actuate the controllable valve of the supplement reservoir to modulate release of the one or more breast milk supplements based on the breast milk supplement regimen.

Figure 25:
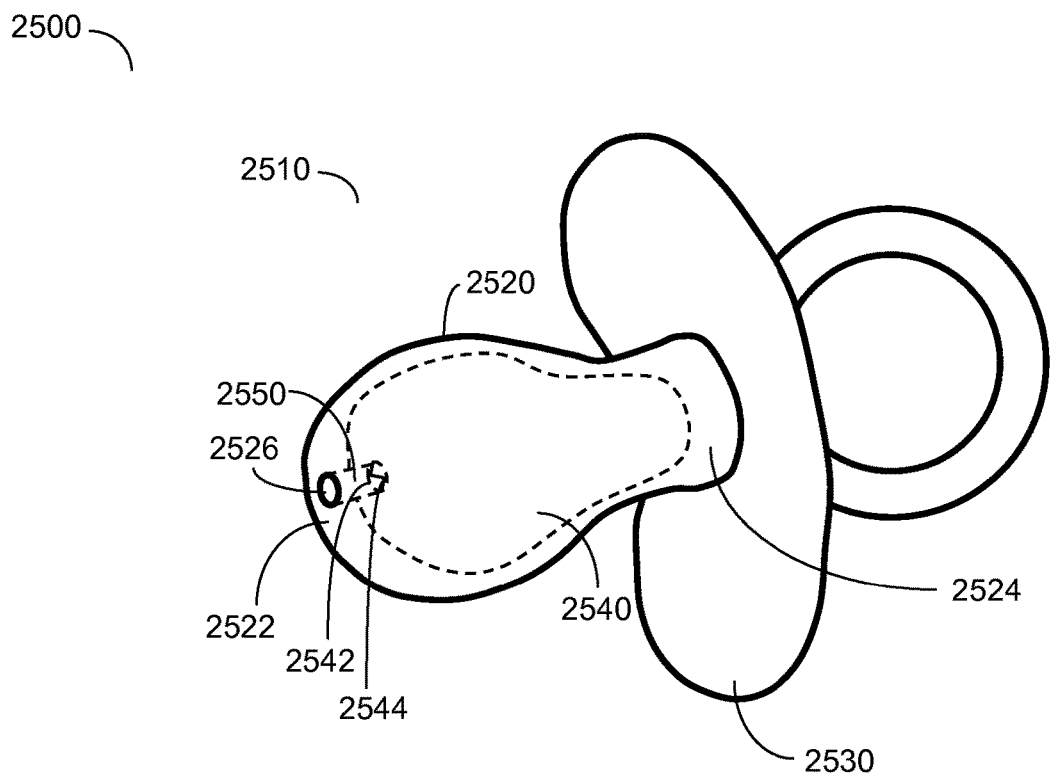
FIG. 25 illustrates an embodiment of a breast milk supplement delivery system.

FIG. 25 illustrates an embodiment of a breast milk supplement delivery system including a delivery unit, a breast milk supplement regimen, and a control unit. Breast milk supplement delivery system 2500 includes delivery unit 2510. Delivery unit 2510 includes a nipple component 2520 sized for placement in an infant's mouth, the nipple component 2520 including a first end 2522 and a second end 2524, the first end 2522 of the nipple component 2520 including an aperture 2526. Delivery unit 2510 includes a guard component 2530 attached to the second end 2524 of nipple component 2520. Delivery unit 2510 includes supplement reservoir 2540 including a port 2542 with a controllable valve 2544. Supplement reservoir 2540 is adapted to contain one or more breast milk supplements. Delivery unit 2510 includes flow conduit 2550 disposed within at least a portion of nipple component 2520. A first end of flow conduit 2550 is in fluid communication with aperture 2526 on the first end 2522 of nipple component 2520. A second end of flow conduit 2550 is in fluid communication with port 2542 of supplement reservoir 2540. In an aspect, the delivery unit includes a handle component attached to at least one of the nipple component and the guard component.

Breast milk supplement delivery system 2500 includes breast milk supplement regimen 2560. The breast milk supplement regimen includes at least one dosing regimen for one or more breast milk supplements. In an aspect, the breast milk supplement regimen includes a systematic or regulated plan for delivery of one or more breast milk supplements to a nursing infant. In an aspect, the breast milk supplement regimen includes one or more types of breast milk supplements and dosing and timing of said breast milk supplements.

Breast milk supplement delivery system 2500 includes control unit 2570 including a microprocessor 2572 and circuitry 2574. Control unit 2570 includes actuation circuitry 2576 configured to wirelessly actuate the controllable valve 2544 of the supplement reservoir 2540 to modulate release of the one or more breast milk supplements based on the breast milk supplement regimen 2560.

The delivery unit 2510 of breast milk supplement delivery system 2500 includes a nipple component 2520 sized for placement in an infant's mouth. In an aspect, the nipple component is formed from a flexible material. In an aspect, the nipple component is formed from at least one of silicone, latex, rubber, or plastic. In an aspect, the nipple component is hollow. For example, the nipple component may consist of a silicone or latex wall defining a hollow space into which other components of the delivery unit are placed. For example, the supplement reservoir, may be sized to fit within a hollow space of the nipple component.

The delivery unit 2510 of breast milk supplement delivery system 2500 includes guard 2530. Guard 2530 is configured to prevent the infant from drawing the nipple component 2520 too far into his/her mouth. In an aspect, the guard is about 1.5 to 2 inches across. The guard may be formed from hard plastic or latex. In an aspect, the guard includes one or more ventilation holes. In an aspect, the nipple component and the guard component comprise a one-piece unit.

The delivery unit 2510 of breast milk supplement delivery system 2500 includes supplement reservoir 2540. In an aspect, the supplement reservoir of the delivery unit is at least partially disposed in at least one of the nipple component and the guard component. In an aspect, the supplement reservoir is completely disposed in either the nipple component or the guard component. In an aspect, the supplement reservoir is attached to an exterior portion of the nipple component and/or the guard component, with a flow conduit attached to the supplement reservoir and extending towards the first end of the nipple component. In an aspect, the flow conduit attached to the exterior positioned supplement reservoir extends along an outer surface of the nipple component. In an aspect, the flow conduit attached to the exterior positioned supplement reservoir at least partially extends through the interior of the nipple component and through the aperture.

Supplement reservoir 2540 includes a port with a controllable valve. In an aspect, the controllable valve is formed from at least one of an electroactive material, a stimulus-responsive hydrogel, or a shape-memory allow. In an aspect, the controllable valve is a piezoelectric valve. In an aspect, the controllable valve includes at least one of a pneumatic valve, a solenoid valve, a poppet valve, a diaphragm valve, or a pinch valve. In an aspect, the controllable valve includes an actuator, the actuator wirelessly responsive to the actuation circuitry of the control unit. In an aspect, the actuator includes at least one of a pneumatic actuator, a hydraulic actuator, a magnetic actuator, or an electric actuator.

Supplement reservoir 2540 is adapted to contain one or more breast milk supplements. In an aspect, at least one of the one or more breast milk supplements includes a lipid, a protein, an oligosaccharide, a fatty acid, a carbohydrate, or a nucleotide, or any combination thereof. In an aspect, at least one of the one or more breast milk supplements includes a nutrient, a micronutrient, a vitamin, an amino acid, or a mineral. In an aspect, at least one of the one or more breast milk supplements includes a therapeutic agent, an antimicrobial agent, a prebiotic, or a probiotic. In an aspect, at least one of the one or more breast milk supplements includes an appetite stimulator or an appetite suppressant. In an aspect, at least one of the one or more breast milk supplements includes a flavoring. In an aspect, the flavoring includes a flavoring preferred by an infant. In an aspect, the flavoring includes a flavoring associated with a specific food type, the flavoring intended to acclimate an infant to the specific food type. Non-limiting examples of breast milk supplements have been described above herein.

In an aspect, a delivery unit includes two or more supplement reservoirs, each of the two or more supplement reservoirs including a port with a controllable valve. In an aspect, each of the two or more supplement reservoirs is adapted to contain the same one or more breast milk supplements. In an aspect, each of the two or more supplement reservoirs is adapted to contain different one or more breast milk supplements. In an aspect, each of the two or more supplement reservoirs is attached through a port to a flow conduit, each of the flow conduits in fluid communication with an aperture defined by a wall of the nipple component.

The delivery unit 2510 of breast milk supplement delivery system 2500 includes a flow conduit 2550 disposed within at least a portion of the nipple component. The flow conduit, e.g., a tube, is in fluid communication with an aperture in the nipple component and a port associated with the supplement reservoir. In response to actuation of the controllable valve of the port, fluid containing one or more breast milk supplements is able to flow from the supplement reservoir, through the flow conduit, and out the aperture at the end of the nipple component. In an aspect, the delivery unit includes two or more flow conduits, a first end of each of the two or more flow conduits in fluid communication with at least one aperture on the first end of the nipple component, a second end of each of the two or more flow conduits in fluid communication with a port associated with a supplement reservoir.

Breast milk supplement delivery system 2500 includes breast milk supplement regimen 2560. In an aspect, the breast milk supplement regimen is stored in a data storage component. In an aspect, the data storage component is incorporated into the control unit. In an aspect, the data storage component includes a removable data storage component. In an aspect, the breast milk supplement regimen is stored on a remote computing device. In an aspect, the breast milk supplement regimen is accessible to the control unit from a remote computing device. In an aspect, the breast milk supplement regimen stored on the remote computing device is wirelessly accessible to the control unit. For example, the breast milk supplement regimen can be stored on a remote computing device associated with a healthcare provider, e.g., a medical office, pediatrician, or lactation specialist. For example, the breast milk supplement regimen can be stored on a remote computing device associated with a breast milk supplement manufacturer or supplier.

In an aspect, breast milk supplement regimen 2560 includes a personalized breast milk supplement regimen. In an aspect, breast milk supplement regimen 2560 is personalized for an infant. In an aspect, the breast milk supplement regimen 2560 is personalized for at least one attribute of the infant. In an aspect, breast milk supplement regimen 2560 is personalized for at least one of age, weight, genome, gender, ethnicity, medical condition, or nutritional need of the infant. In an aspect, breast milk supplement regimen 2560 is personalized for a lactating female. In an aspect, the lactating female is the infant's mother. In an aspect, the lactating female is a nursemaid or surrogate for the infant. In an aspect, breast milk supplement regimen 2560 is personalized for a quality of breast milk of the lactating female. In an aspect, breast milk supplement regimen 2560 is personalized for at least one of a nutritional quality, a microbial quality, or an immunological quality of the breast milk of the lactating female. In an aspect, breast milk supplement regimen 2560 is adjustable. In an aspect, breast milk supplement regimen 2560 is adjustable based on a change in at least one of an attribute of an infant and/or a quality of breast milk of the lactating female.

Breast milk supplement delivery system includes control unit 2570 including microprocessor 2572 and circuitry 2574. Control unit 2570 includes actuation circuitry configured to wirelessly actuate the controllable valve of the supplement reservoir. In an aspect, the actuation circuitry includes circuitry configured to at least partially open or close the controllable valve. In an aspect, the actuation circuitry includes circuitry configured to at least one of open the controllable valve, close the controllable valve, change a pressure threshold of the controllable valve, increase an opening size of the controllable valve, decrease an opening size of the controllable valve, or alter a permeability or porosity of the controllable valve. In an aspect, the control unit includes at least one of a computer, a laptop computer, a personal electronic device, a dedicated computing device, a limited resource computing device, a wireless communication device, a mobile wireless communication device, a handheld electronic writing device, a tablet, a digital camera, a scanner, a cell phone, a PDA, or an electronic tablet device. In an aspect, the control unit includes a standalone device. For example, the control unit can be a handheld device designed for specific use with the delivery unit for controllable delivery of breast milk supplements. In an aspect, the control unit includes a special use computing device. For example, the control unit can include a computing device designed for specific use with the delivery unit. In an aspect, the control unit is associated with a personal electronic device. For example, the control unit can be associated with a smart phone or tablet device. For example, the control unit can take advantage of a microprocessor and circuitry associated with a smart phone or tablet device. In an aspect, the control unit is associated with a computing device. For example, the control unit can be associated with a home personal computer, e.g., a laptop or tablet computer. In an aspect, the standalone device, the special use computing device, the personal electronic device or computing device can include one or more instructions for remotely operating the breast milk supplement delivery device.

In an aspect, the delivery unit 2510 of breast milk supplement delivery system 2500 includes at least one delivery event sensor. In an aspect, the delivery event sensor includes at least one of a flow sensor, a pressure sensor, a strain sensor, a weight sensor, a conductivity sensor, an acoustic sensor, an optical transmission sensor, or a clock. In an aspect, the delivery event sensor senses that one or more breast milk supplements have been delivered based on fluid flow and or changes in the volume within the supplement reservoir. In an aspect, the control unit 2570 includes delivery event circuitry configured to wirelessly receive information associated with a delivery event from delivery unit 2510. In an aspect, the delivery event circuitry includes circuitry configured to wirelessly receive information associated with at least one of a breast milk supplement type, an infant identifier, a dosage, a time, or a date from delivery unit 2510.

In an aspect, the control unit 2570 of breast milk supplement delivery system 2500 includes reporting circuitry configured to report a delivery event. In an aspect, the reporting circuitry includes circuitry configured to report at least one of a breast milk supplement type, a dosage, an infant identifier, a time, or a date. In an aspect, the reporting circuitry includes circuitry configured to report the delivery event through a user interface. In an aspect, the reporting circuitry includes circuitry configured to report the delivery event to a second computing device.

In an aspect, breast milk supplement delivery system 2500 includes a user interface operably coupled to control unit 2570. In an aspect, the user interface includes one or more input components and one or more output components. Non-limiting examples of a user interface have been described above herein. The user interface can be used to enter information, e.g., infant identifier, age, weight, gender, ethnicity, nutritional need, or medical condition of an infant. The user interface can be used to report to a user an infant identifier, analyte information, a breast milk supplement type, a dosage, a time, or a date. In an aspect, the user interface is integrated into at least one of the delivery unit and the control unit or may be one or more peripheral devices operably connected through a wired or wireless connection to at least one of the delivery unit and the control unit. In some embodiments, the user interface is user driven. For example, the user inputs data or operating conditions at least one of the delivery unit and the control unit using the user interface, e.g., a touch-screen. In some embodiments, the user interface, e.g., a switch, is circuitry driven. For example, an on/off switch may be toggled based on proximity of a portion of the delivery unit to the infant.

In an aspect, breast milk supplement delivery system 2500 includes at least one transmission unit, the at least one transmission unit including circuitry and at least one antenna. In an aspect, the at least one transmission unit is operably coupled to the control unit 2570. For example, the control unit can include a transmission unit for transmitting one or more instructions or actuation signals to the delivery unit and for receiving information associated with delivery events. In an aspect, the at least one transmission unit is attached to the delivery unit 2510. For example, the delivery unit can include a transmission unit for transmitting delivery event information and for receiving operation instructions and actuation signals. In an aspect, the at least one transmission unit includes at least one transmitter and at least one receiver. In an aspect, the at least one transmission unit includes at least one of a radiofrequency transmission unit, a radiofrequency identification (RFID) transmission unit, an optical transmission unit, or an audio transmission unit. In an aspect, at least one transmission unit is associated with the control unit 2570 and at least one transmission unit is associated with the delivery unit 2510.

In an aspect, breast milk supplement delivery system 2500 includes at least one analyte sensor associated with delivery unit 2510, the at least one analyte sensor configured to sense at least one analyte. In an aspect, the at least one analyte sensor is associated with at least one surface of the nipple component 2520 of the delivery unit 2510. In an aspect, the at least one analyte sensor is associated with an outer surface of the guard component 2530 of the delivery unit 2510. In an aspect, the at least one analyte sensor includes a saliva analyte sensor. In an aspect, the at least one analyte sensor includes an exhaled breath analyte sensor. In an aspect, the control unit 2570 includes circuitry configured to wirelessly receive information associated with the at least one analyte from the at least one analyte sensor associated with the delivery unit 2510 and to wirelessly actuate the controllable valve 2544 of the supplement reservoir 2540 to modulate release of the one or more breast milk supplements in response to the received information associated with the at least one analyte.

In an aspect, delivery unit 2510 of breast milk supplement delivery system 2500 includes at least one power source. For example, the at least one power source can include one or more batteries, e.g., AAA batteries. Other non-limiting examples of power sources have been described above herein.

In an aspect, breast milk supplement delivery system 2500 includes an infant presence detector. In an aspect, the infant presence detector is configured to detect the presence or absence of the infant in proximity to the delivery unit, and to provide an infant presence signal to the control unit. In an aspect, the actuation circuitry includes circuitry configured to wirelessly actuate the controllable valve of the supplement reservoir based on the infant presence signal. In an aspect, the infant presence detector includes at least one of a temperature sensor, a pressure sensor, an electrical conductivity sensor, a radar sensor, an ultrasonic sensor, a microphone, a camera, a photodetector, or a strain sensor.

In an aspect, breast milk supplement delivery system 2500 includes a temperature control component. In an aspect, the temperature control component is configured to heat at least one of the nipple and the contents of the one or more supplement reservoirs for the comfort of the infant.

FIGS. 26 and 27 illustrate further aspects of a breast milk supplement delivery system. FIG. 26 shows breast milk supplement delivery system 2600 including delivery unit 2610 and control unit 2620, e.g., a smart phone. Delivery unit 2610 is shown placed in the mouth of infant 2630. Delivery unit 2610 includes at least one transmission unit including at least one transmitter and at least one receiver. The at least one transmission unit of delivery unit 2610 is configured to transmit signals 2640 to control unit 2620 and to receive signals 2650 from control unit 2620. Control unit 2620 includes at least one transmission unit including at least one transmitter and at least one receiver. The at least one transmission unit of control unit 2620 is configured to transmit signals 2650 to delivery unit 2610 and to receive signals 2640 from delivery unit 2610. FIG. 27 shows breast milk supplement delivery system 2700 including delivery unit 2710 and control unit 2720, e.g., a computer. Delivery unit 2710 is shown placed in the mouth of infant 2730. Delivery unit 2710 includes at least one transmission unit including at least one transmitter and at least one receiver. The at least one transmission unit of delivery unit 2710 is configured to transmit signals 2740 to control unit 2720 and to receive signals 2750 from control unit 2720. Control unit 2720 includes at least one transmission unit including at least one transmitter and at least one receiver. The at least one transmission unit of control unit 2720 is configured to transmit signals 2750 to delivery unit 2710 and to receive signals 2740 from delivery unit 2710.

FIGS. 28-30 illustrate aspects of method 2800 for controlling delivery of breast milk supplementation. Method 2800 includes in block 2810 receiving information associated with a breast milk supplement regimen with a breast milk supplement delivery device, the breast milk supplement delivery device including a substrate sized for placement one a surface of a breast region of a lactating female, at least one supplement reservoir associated with the substrate and adapted to contain one or more breast milk supplements, the at least one supplement reservoir including a port with a controllable valve, a data storage component configured to store the breast milk supplement regimen, and a control unit including a microprocessor and circuitry, the control operably coupled to the data storage component and to the controllable valve of the at least one supplement reservoir. Method 2800 includes in block 2820 actuating the controllable valve of the at least one supplement reservoir to modulate release of the one or more breast milk supplements based on the received breast milk supplement regimen.

FIG. 29 illustrates further aspects of a method such as shown in FIG. 28. Method 2800 includes in block 2810 receiving information associated with a breast milk supplement regimen with a breast milk supplement delivery device. In an aspect, method 2800 includes wirelessly receiving the information associated with the breast milk supplement regimen, as shown in block 2900. For example, the method can include wirelessly receiving the information associated with the breast milk supplement regimen from a remote computing device associated with an infant's healthcare provider, e.g., a pediatrician, family doctor, and/or lactation specialist. For example, the method can include wireless receiving the information from a website, the cloud, and/or a remote server. In an aspect, method 2800 includes receiving the information associated with the breast milk supplement regimen from a removable data storage component, as shown in block 2910. For example, the method can include receiving the information associated with the breast milk supplement regimen from a memory stick or card inserted into the breast milk supplement delivery device. In an aspect, the method includes receiving the information associated with the breast milk supplement regimen through a user interface associated with the breast milk supplement delivery device, as shown in block 2920. For example, the method can include using a user interface, e.g., a touchscreen display and/or buttons, to enter the breast milk supplement regimen into the breast milk supplement delivery device.

Method 2800 includes in block 2820 actuating the controllable valve of the at least one supplement reservoir to modulate release of one or more breast milk supplements based on the received breast milk supplement regimen. In an aspect, method 2800 includes actuating the controllable valve to at least partially open or close the controllable valve, as shown in block 2930. In an aspect, method 2800 includes actuating the controllable valve to at least one of open the controllable valve, close the controllable valve, change a pressure threshold of the controllable valve, increase an opening size of the controllable valve, decrease an opening size of the controllable valve, or alter a permeability or porosity of the controllable valve, as shown in block 2940. In an aspect, method 2800 includes actuating the controllable valve to modulate release of a specified amount of the one or more breast milk supplements during a feeding event, as shown in block 2950. In an aspect, method 2800 includes actuating the controllable valve to modulate release of a specified cumulative amount of the one or more breast milk supplements over a plurality of feeding events, as shown in block 2960. In an aspect, method 2800 includes actuating the controllable valve to modulate release of a specified cumulative amount of the one or more breast milk supplements over a plurality of feeding events within a specified time period, as shown in block 2970. In an aspect, method 2800 includes actuating the controllable valve to cease release of the one or more breast milk supplements once a specified amount of the one or more breast milk supplements has been delivered, as shown in block 2980.

FIG. 30 illustrates further aspects of a method such as shown in FIG. 28. In an aspect, method 2800 includes recording a delivery event with at least one delivery event sensor, as shown block 3000. For example, the method can include recording a delivery event using at least one of a flow sensor, a pressure sensor, a strain sensor, a weight sensor, a conductivity sensor, an acoustic sensor, an optical transmission sensor, or a clock. In an aspect, method 2800 includes recording at least one of a breast milk supplement type, a dosage, an infant identifier, a time, or a date, as shown in block 3005.

In an aspect, method 2800 includes reporting a delivery event, as shown in block 3010. In an aspect, method 2800 includes reporting at least one of a breast milk supplement type, a dosage, an infant identifier, a time, or a date, as shown in block 3015. In an aspect, method 2800 includes reporting the delivery event through at least one of a radiofrequency transmission, a radiofrequency identification (RFID) transmission, an optical transmission, or an audio transmission, as shown in block 3020. In an aspect, method 2800 includes reporting the delivery event through at least one of an electrical wire, an optical fiber, or a removable storage medium, as shown in block 3025. In an aspect, method 2800 includes reporting the delivery event to a computing device, as shown in block 3030. In an aspect, method 2800 includes reporting the delivery event to a personal electronic device, as shown in block 3035. In an aspect, method 2800 include reporting the delivery event to a user interface associated with the breast milk supplement delivery device, as shown in block 3040.

In an aspect, method 2800 includes adjusting the breast milk supplement regimen, as shown in block 3045. In an aspect, method 2800 includes adjusting the breast milk supplement regimen based on attributes of an infant, as shown in block 3050. In an aspect, method 2800 includes adjusting the breast milk supplement regimen based on at least one of age, weight, genome, gender, ethnicity, medical condition, or nutritional need of the infant, as shown in block 3055. In an aspect, method 2800 includes adjusting the breast milk supplement regimen based on a quality of breast milk of the lactating female, as shown in block 3060. In an aspect, method 2800 includes adjusting the breast milk supplement regimen based on at least one of a nutritional quality, a microbial quality, or immunological quality of the breast milk of the lactating female, as shown in block 3065.

FIG. 31 illustrates further aspects of a method such as shown in FIG. 28. In an aspect, method 2800 includes receiving information associated with at least one analyte from an analyte sensor associated with the breast milk supplement delivery device, as shown in block 3100. In an aspect, method 2800 includes receiving information associated with at least one saliva analyte, at least one breast milk analyte, or at least one exhaled breath analyte, as shown in block 3110. In an aspect, method 2800 includes receiving information associated with at least one analyte from at least one of a saliva analyte sensor, a breast milk analyte sensor, or an exhaled breath analyte sensor, as shown in block 3120. In an aspect, method 2800 includes adjusting the breast milk supplement regimen in response to the received information associated with the at least one analyte, as shown in block 3130. In an aspect, method 2800 includes actuating the controllable valve of the at least one supplement reservoir to modulate release of the one or more breast milk supplements based on the adjusted breast milk supplement regimen, as shown in block 3140. In an aspect, method 2800 includes receiving information associated with a proximity of an infant to the breast milk supplement delivery device with an infant presence detector and actuating the controllable valve of the at least one supplement reservoir in response to the received information associated with the proximity of the infant, as shown in block 3150. In an aspect, method 2800 includes vibrating at least a portion of the breast milk supplement delivery device, as shown in block 3160. In an aspect, method 2800 includes at least one of heating and cooling at least a portion of the breast milk supplement delivery device, as shown in block 3170.

FIGS. 32-34 illustrate aspects of method 3200 for controlling delivery of breast milk supplementation. With regard to FIG. 32, method 3200 includes in block 3210 receiving information associated with at least one analyte from an analyte sensor incorporated into a breast milk supplement delivery device, the breast milk supplement delivery device including the analyte sensor, a substrate sized for placement on a surface of a breast region of a lactating female, at least one supplement reservoir associated with the substrate and adapted to contain one or more breast milk supplements, the at least one supplement reservoir including a port with a controllable valve, and a control unit including a microprocessor and circuitry, the control unit operably coupled to the analyte sensor and the controllable valve of the at least one supplement reservoir. Method 3200 includes in block 3220 actuating the controllable valve of the at least one supplement reservoir to modulate release of the one or more breast milk supplements in response to the received information associated with the at least one analyte.

FIG. 33 illustrates further aspects of a method such as shown in FIG. 32. Method 3200 includes in block 3210 receiving information associated with at least one analyte from an analyte sensor. In an aspect, method 3200 includes receiving information associated with at least one breast milk analyte from a breast milk analyte sensor, as shown in block 3300. In an aspect, method 3200 includes receiving information associated with at least one saliva analyte from a saliva analyte sensor, as shown in block 3305. In an aspect, method 3200 includes receiving information associated with at least one exhaled breath analyte from an exhaled breath analyte sensor as shown in block 3310.

In an aspect, method 3200 includes in block 3315 recording a delivery event with at least one delivery event sensor. In an aspect, method 3200 includes recording at least one of a breast milk supplement type, a dosage, an infant identifier, a time, or a date, as shown in block 3320.

In an aspect, method 3200 includes in block 3325 reporting a delivery event. In an aspect, method 3200 includes reporting the delivery event through at least one of a radiofrequency transmission, a radiofrequency identification (RFID) transmission, an optical transmission, or an audio transmission, as shown in block 3330. In an aspect, method 3200 includes reporting the delivery event through at least one of an electrical wire, an optical fiber, or a removable storage medium, as shown in block 3335. In an aspect, method 3200 includes reporting the delivery event to a computing device, as shown in block 3340. In an aspect, method 3200 includes reporting the delivery event to a personal electronic device, as shown in block 3345. In an aspect, method 3200 includes reporting the delivery event to a user interface associated with the breast milk supplement delivery device, as shown in block 3350.

Method 3200 includes actuating the controllable valve of the at least one supplement reservoir. In an aspect, method 3200 includes actuating the controllable valve to at least partially open or close the controllable valve, as shown in block 3355. In an aspect, method 3200 includes actuating the controllable valve to at least one of open the controllable valve, close the controllable valve, change a pressure threshold of the controllable valve, increase an opening size of the controllable valve, decrease an opening size of the controllable valve, or alter a permeability or porosity of the controllable valve, as shown in block 3360.

FIG. 34 illustrates further aspects of method 3200. In an aspect, method 3200 includes in block 3400 receiving information associated with a breast milk supplement regimen. In an aspect, method 3200 includes wirelessly receiving the information associated with the breast milk supplement regimen, as shown in block 3410. In an aspect, method 3200 includes receiving the information associated with the breast milk supplement regimen from a removable data storage component, as shown in block 3420. In an aspect, method 3200 includes receiving the information associated with the breast milk supplement regimen through a user interface associated with the breast milk supplement regimen, as shown in block 3430. In an aspect, method 3200 includes receiving information associated with a breast milk supplement regimen personalized for attributes of at least one infant, as shown in block 3440. In an aspect, method 3200 includes receiving information associated with a breast milk supplement regimen personalized for a quality of breast milk of the lactating female, as shown in block 3450. In an aspect, method 3200 includes modifying the breast milk supplement regimen in response to the received information associated with the at least one analyte; and actuating the controllable valve of at least one of the one or more supplement reservoirs to modulate release of the one or more breast milk supplements in response to the modified breast milk supplement regimen, as shown in block 3460.

In an aspect, method 3200 includes receiving information associated with a proximity of an infant to the breast milk supplement delivery device with an infant presence detector and actuating the controllable valve of the at least one supplement reservoir in response to the received information associated with the proximity of the infant, as shown in block 3470. In an aspect, method 3200 includes vibrating at least a portion of the breast milk supplement delivery device, as shown in block 3480. In an aspect, method 3200 includes at least one heating and cooling at least a portion of the breast milk supplement delivery device, as shown in block 3490.

FIGS. 35 and 36 illustrate aspects of a system 3500 for controlling delivery of breast milk supplementation to an infant. FIG. 35 shows a block diagram of system 3500 including circuitry 3510 for receiving information associated with a breast milk supplement regimen; and circuitry 3520 for actuating a controllable valve of at least one of one or more supplement reservoirs associated with a breast milk supplement delivery device to modulate release of one or more breast milk supplements from the at least one of the one or more supplement reservoirs based on the received breast milk supplement regimen.

FIG. 36 illustrates further aspects of system 3500. In an aspect, system 3500 includes computing component 3600. In an aspect, the circuitry of system 3500 is incorporated into computing component 3600. In an aspect, circuitry 3510 for receiving the information associated with the breast milk supplement regimen includes circuitry 3610 for wirelessly receiving the information associated with the breast milk supplement regimen. In an aspect, system 3500 further includes circuitry 3620 for receiving information from a delivery event sensor. For example, the system can include circuitry for receiving information from at least one of a flow sensor, a conductivity sensor, an acoustic sensor, or an optical transmission sensor associated with the breast milk supplement delivery device. In an aspect, system 3500 includes circuitry 3630 for recording a delivery event with a delivery event sensor. In an aspect, circuitry 3630 includes circuitry for recording at least one of a breast milk supplement type, a dosage, an infant identifier, a time, or a date. In an aspect, system 3500 includes circuitry 3640 for reporting a delivery event. In an aspect, circuitry 3640 includes circuitry for reporting the delivery event includes circuitry for reporting the delivery event to at least one of a personal electronic device, a computing device, or a user interface. In an aspect, system 3500 includes circuitry 3660 for receiving information associated with at least one analyte from an analyte sensor. In an aspect, circuitry 3660 includes circuitry 3670 for modifying the breast milk supplement regimen in response to the received information associated with the at least one analyte; and circuitry for actuating the controllable valve of at least one of the one or more supplement reservoirs associated with the breast milk supplement delivery device to modulate release of the one or more breast milk supplements based on the modified breast milk supplement regimen.

In an aspect, computing component 3600 of system 3500 comprises a special use computing component. In an embodiment, the system is integrated in such a manner that the system operates as a unique system configured specifically for function of the breast milk supplement delivery device, and any associated computing devices of the system operate as specific use computers for purposes of the claimed system, and not general use computers. In an embodiment, at least one associated computing device of the system operate as specific use computers for purposes of the claimed system, and not general use computers. In an embodiment, at least one of the associated computing devices of the system are hardwired with a specific ROM to instruct the at least one computing device.

FIGS. 37 and 38 illustrate aspects of system 3700 for controlling delivery of breast milk supplementation to an infant. FIG. 37 shows a block diagram of system 3700 including circuitry 3710 for receiving information associated with at least one analyte from an analyte sensor incorporated into a breast milk supplement delivery device; and circuitry 3720 for actuating a controllable valve of at least one of one or more supplement reservoirs associated with the breast milk supplement delivery device to modulate release of one or more breast milk supplements in response to the received information associated with the at least one analyte.

FIG. 38 illustrates further aspects of system 3700. In an aspect, system 3700 includes a computing component 3800. In an aspect, the circuitry of system 3700 is incorporated into computing component 3800. In an aspect, computing component 3800 comprises a specific use computing component. In an aspect, circuitry 3710 for receiving the information associated with the at least one analyte from the analyte sensor includes circuitry 3810 for receiving information associated with at least one saliva analyte from a saliva analyte sensor. In an aspect, circuitry 3710 for receiving the information associated with the at least one analyte from the analyte sensor includes circuitry 3820 for receiving information associated with at least one breast milk analyte from a breast milk analyte sensor. In an aspect, circuitry 3710 for receiving the information associated with the at least one analyte from the analyte sensor includes circuitry 3830 for receiving information associated with at least one exhaled breath analyte from an exhaled breath analyte sensor. In an aspect, system 3700 includes circuitry 3840 for receiving information from a delivery event sensor. In an aspect, system 3700 includes circuitry 3850 for recording a delivery event from a delivery event sensor. In an aspect, circuitry 3850 for recording a delivery event from a delivery event sensor includes circuitry for recording at least one of a breast milk supplement type, a dosage, an infant identifier, a time, or a date. In an aspect, system 3700 includes circuitry 3860 for reporting a delivery event. In an aspect, circuitry 3860 for reporting the delivery event includes circuitry for reporting at least one of a breast milk supplement type, a dosage, an infant identifier, a time, or a date. In an aspect, circuitry 3860 for reporting the delivery event includes circuitry for reporting the delivery event to at least one of a personal electronic device, a computing device, or a user interface. In an aspect, circuitry 3700 includes circuitry 3870 for receiving information associated with a breast milk supplement regimen. In an aspect, system 3700 includes circuitry for modifying the received information associated with the breast milk supplement regimen in response to the received information associated with the at least one analyte; and circuitry for actuating the controllable valve of at least one of the one or more supplement reservoirs associated with the breast milk supplement delivery device to modulate release of the one or more breast milk supplements based on the modified breast milk supplement regimen.

Figure 39:
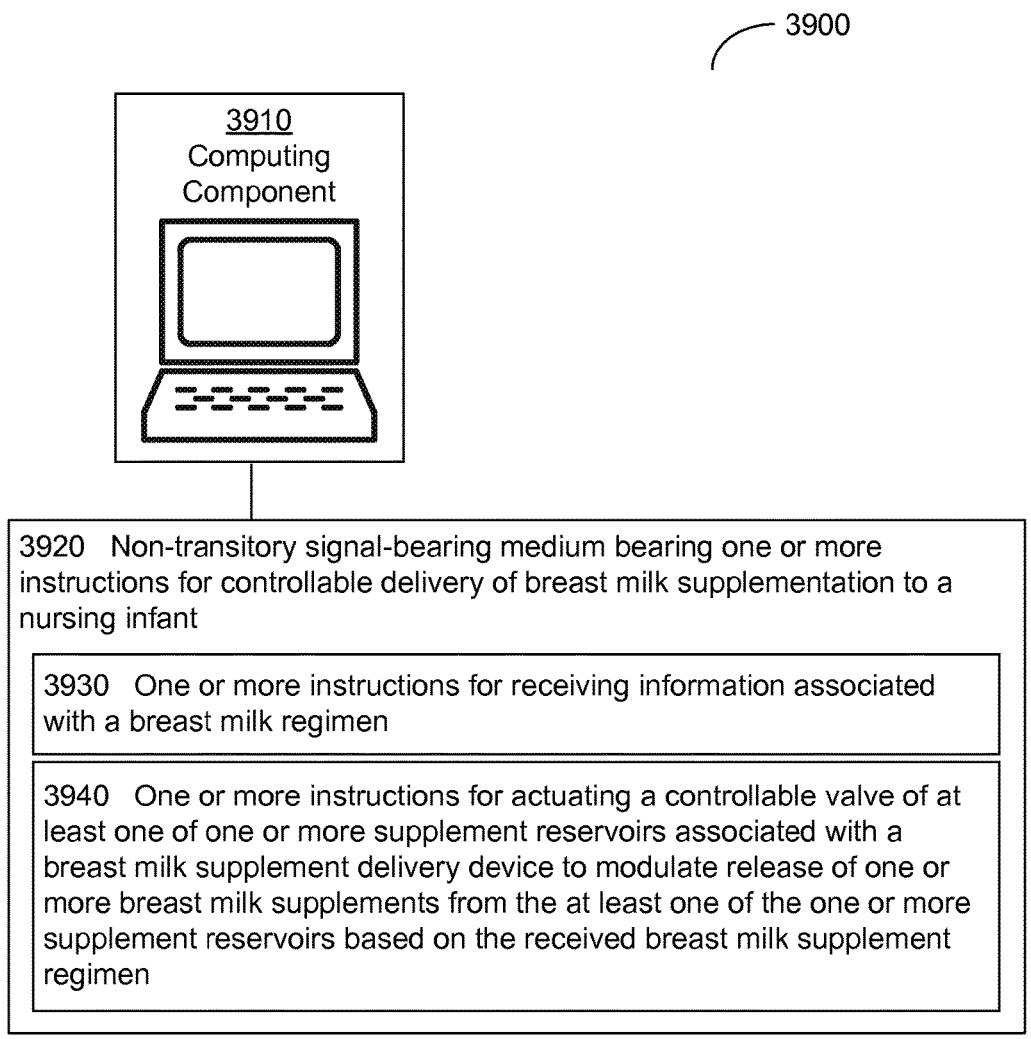
FIG. 39 illustrates an embodiment of a system for controlling delivery of breast milk supplementation.
Figure 40:
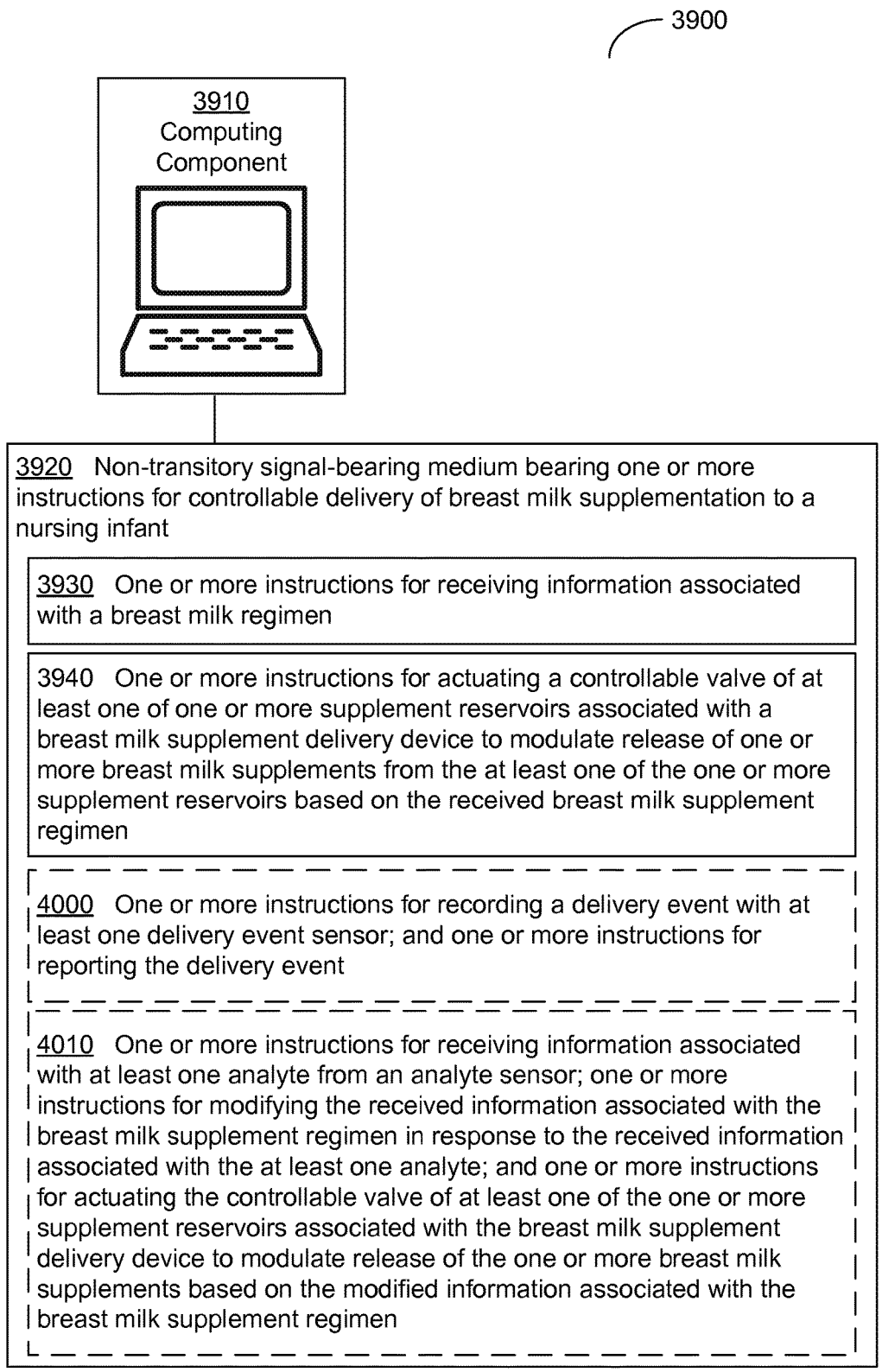
FIG. 40 illustrates further aspects of a system such as shown in FIG. 39.

FIGS. 39 and 40 illustrate aspects of a system 3900. With regard to FIG. 39, system 3900 includes computing component 3910 including a processor and non-transitory signal-bearing medium 3920 bearing one or more instructions for controllable delivery of breast milk supplementation to a nursing infant. In an aspect, computing component 3910 comprises a special use computing component. Non-transitory signal-bearing medium 3920 includes one or more instructions 3930 for receiving information associated with a breast milk supplement regimen; and one or more instructions 3940 for actuating a controllable valve of at least one of one or more supplement reservoirs associated with a breast milk supplement delivery device to modulate release of one or more breast milk supplements from the at least one of the one or more supplement reservoirs based on the received breast milk supplement regimen. FIG. 40 illustrates further aspects of system 3900. In an aspect, non-transitory signal bearing medium 3920 includes one or more instructions 4000 for recording a delivery event with at least one delivery event sensor; and one or more instructions for reporting the delivery event. In an aspect, non-transitory signal bearing medium 3920 includes one or more instructions 4010 for receiving information associated with at least one analyte from an analyte sensor; one or more instructions for modifying the received information associated with the breast milk supplement regimen in response to the received information associated with the at least one analyte; and one or more instructions for actuating the controllable valve of at least one of the one or more supplement reservoirs associated with the breast milk supplement delivery device to modulate release of the one or more breast milk supplements based on the modified information associated with the breast milk supplement regimen.

Various non-limiting embodiments are described herein as Prophetic Examples.

Prophetic Example 2: Smart Patch to Deliver Breast Milk Supplements

An embodiment of a breast milk supplement delivery device designed to adhere to a nursing mother's breast, deliver breast milk supplements, and to control the amounts of supplemental nutrients received by an infant is described. In this non-limiting example, the breast milk supplement delivery device takes the form of a flexible patch constructed with reservoirs, ports and valves to control the delivery of breast milk supplements to an infant. Electronic microcircuitry and microprocessors are incorporated in the flexible patch to control nutrient delivery according to a breast milk supplement regimen encoded in the device memory. Moreover the flexible patch includes: a transceiver to report a delivery event and to receive breast milk supplement regimen programs. Analyte sensors on the flexible patch detect supplements and metabolites in the infant's saliva and the mother's milk; analyte data is processed and used to adjust the breast milk supplement regimen, e.g., dosage, schedule, and composition.

A flexible, adherent breast patch that incorporates breast milk supplement reservoirs with valves to control the flow of supplements from the breast patch is based upon a multi-layer polymeric substrate. A skin-adhesive first layer of the breast patch is cast using an acrylate copolymer dissolved in a volatile organic solvent which is subsequently evaporated to leave a planar, pressure sensitive adhesive patch. For example, an acrylate copolymer adhesive, dissolved in ethyl acetate may be cast as a donut-shaped patch that adheres to skin surrounding a breast nipple (see FIG. 2D). A second layer of polymer, e.g., polyurethane, is cast in a donut shape to overlay the adhesive first layer. (See e.g., U.S. Patent Application No. 2003/0152612 by Pugliese et al. published on Aug. 14, 2003 which is incorporated herein by reference.) The polyurethane layer is cast with reservoirs which are embedded in sectors of the circular layer. Each reservoir is equipped with a conductivity meter to monitor the level of supplement in the reservoir. A thin film conductivity sensor approximately 1.5 cm in length is available from Innovative Sensor Technology USA, Las Vegas, Nev. (see the Info Sheet: Conductivity Sensor LFS155). The capacity of each reservoir is approximately 0.5 mL, and each reservoir has a port which permits influx or efflux of liquid supplements. Flow at each reservoir port is controlled by an electroactive polymer valve which is responsive to a microprocessor/controller. For example, an electroactive polymer valve may be constructed by electrochemically depositing polypyrrole-para-toluenesulfonate onto a PVDF substrate to create a membrane that selectively transports cations when a pulsed, square wave potential is applied to the membrane (see e.g., Price et al., Synthetic Metals 102: 1338-1341, 1999 which is incorporated herein by reference). Electroactive membranes with pores of preselected sizes may be created with an etching process using ion beam technology (see e.g., U.S. Pat. No. 7,632,406 issued to Wilson et al. on Dec. 15, 2009 which is incorporated herein by reference). Membranes comprised of electroactive polymers can act as valves with pores approximately 0.1-5.0 µm in diameter that open or close depending on the oxidation state of the polymers (see e.g., U.S. Patent Pub. No. 2006/0138371 by Gamier published on Jun. 29, 2006 which is incorporated herein by reference).

An absorbent polymer, e.g., hydrogel, is attached as a circular strip adjacent to the valve outlets on each reservoir port. For example the hydrogel may be composed of a polyvinyl alcohol (PVA)/polyethylene-co-vinyl alcohol (EVAL) copolymer combined with polyvinyl alcohol (PVA), and cast in an aluminum mold to create a planar, circular absorbent hydrogel surrounding the nipple. The hydrogel strip absorbs breast milk supplements from the reservoirs and presents them adjacent to the nipple for a breast feeding infant. Methods and materials for casting hydrogels are described (see e.g., U.S. Pat. No. 7,731,988 issued to Thomas et al. on Jun. 8, 2010 which is incorporated herein by reference).

The breast patch contains analyte sensors that monitor the levels of saliva analytes in the infant's saliva and/or breast milk analytes in the lactating female's breast milk in order to provide feedback to the control unit of the breast patch to control the delivery of breast milk supplements based on a breast milk supplement regimen personalized for the infant and mother. Analyte sensors are attached to the breast patch substrate, polyurethane layer, proximal to the nipple to allow sensing of nutrients, metabolites and biologicals in infant saliva and in breast milk. The levels of vitamins in infant saliva and breast milk are detected and reported to the control unit of the breast patch. For example, an analyte sensor to detect vitamin D may be used to monitor an infant's saliva and provide feedback to the control unit on the breast patch.

A biosensor based on a single-walled carbon nanotube (SWNT) with an aptamer recognition element for 25-hydroxy vitamin D (25-OH-D) is attached to the breast patch at a positioned adapted for placement in proximity to the nipple to sample saliva from the breast feeding infant.

Methods and materials to construct SWNT biosensors with selected aptamers are described (see e.g., So et al., *J. Am. Chem. Soc.* 127, 11906-11907 and U.S. Pat. No. 5,475,096 issued to Gold et al. on Dec. 12, 1995 which are incorporated herein by reference).

The recommended serum level for 25-OH-D in adults is approximately ≥50 nmoles/L, and similar minimum levels are likely to be recommended for infant sera and infant saliva (see e.g., Wagner et al., *Pediatrics* 122, 1142-1152, 2008 and Fairney and Saphier, British Journal of Nutrition 57, 13-25, 1987 which are both incorporated herein by reference). Biosensor data on saliva 25-OH-D levels are received and processed by microcircuitry on the patch, and if 25-OH-D levels are insufficient (e.g., below 50 nmoles/L) then vitamin D3 supplement is delivered from the supplement reservoir. For example, a supplement of vitamin D3 as an oral preparation is available from Biotics Research Laboratory, Rosenberg, Tex. A supplement reservoir may contain 0.5 mL of vitamin D3 at a concentration of approximately 4000 IU/mL which is delivered at a rate of approximately 0.100 mL (400 IU)/day. Feedback from the 25-OH-D biosensor may indicate more or less vitamin D3 is required to keep the infant's saliva level at ≥50 nmoles/L. The breast patch microcircuitry and processors may be programmed to adjust the regimen to maintain a predetermined level of salivary 25-OH-D (e.g., ≥50 nmoles/L), or to deliver a daily dose of vitamin D according to a preset regimen recommended by health authorities (see e.g., Wagner et al., Ibid.). Input and modification of breast milk supplement regimen in the breast patch is mediated by radio frequency identification (RFID) tags which receive information from a remote computer or mobile device (i.e., cell phone, tablet, etc.).

The breast patch incorporates a RFID tag that includes antennas and circuitry to receive and transmit radio frequency signals to communicate with external computers and or mobile devices. The RFID tag is fabricated on a microchip that is attached to the upper polyurethane layer of the breast patch. For example the RFID device may be constructed by printing conductive ink (e.g., polymer with flecks of silver) to create circuitry. Conductive ink is used to print RFID antennas and to connect electronic components on the device. An integrated circuit defining the RFID circuitry for the device is printed on the substrate with conductive epoxy in connection with the conductive ink. The antenna may be a dipole antenna with a capacitor built in to store some of the electrical energy harvested from incident radio waves. The device may have a transmit circuit and a receive circuit to control radio wave communications through the antenna, a power harvester circuit to provide power to the device and a control circuit. Encapsulating epoxy material is used to cover the integrated circuit, the conductive ink and conductive epoxy. Methods and materials to construct RFID tags connected to sensors are described (see e.g., U.S. Pat. No. 7,479,886 issued to Burr on Jan. 20, 2009; U.S. Pat. No. 6,693,513 issue to Tuttle on Feb. 17, 2004 and U.S. Pat. No. 7,411,505 issued to Smith et al. on Aug. 12, 2008 which are incorporated herein by reference). The RFID device with an antenna for transmitting signals to a RFID reader may be constructed with circuitry to send an identification signal, and to transmit an alert when a delivery event has occurred or a supplement reservoir is nearly empty as indicated by the conductivity sensor (see e.g., Sample et al., *IEEE Trans. Instr. Meas.* 57: 2608-2615, 2008 which is incorporated herein by reference).

Prophetic Example 2: Smart Breast Patch to Deliver Supplements and Flavorings

An embodiment of a breast milk supplement delivery device including supplement reservoirs, tubing, ports, controllable valves and a pump to deliver breast milk supplements and flavorings to a breastfeeding infant is described. In this non-limiting example, the breast milk supplement delivery device takes the form of a flexible patch adapted for placement on a breast region of a lactating female. The breast patch includes microcircuitry, microprocessors, data storage components, and wireless transmission and receiving elements and a battery power source. Controlled delivery of breast milk supplements and flavorings is executed according to programmed regimens, and recorded and transmitted remotely by the breast patch. The breast patch is designed to adhere to the breast and position a delivery/sampling tube near to the nipple for supplement feeding or saliva or breast milk sample acquisition.

An adherent breast patch is constructed with a flexible, adherent lower layer and a polyurethane upper layer that includes sites for: reservoirs, a peristaltic pump, tubing, microcircuitry and a power source. A skin-adhesive first layer of the breast patch is cast using an acrylate copolymer dissolved in a volatile organic solvent which is subsequently evaporated to leave a planar, pressure sensitive adhesive patch. For example, an acrylate copolymer adhesive, dissolved in ethyl acetate may be cast as a rectangular patch approximately 5.0 cm×2.5 cm that adheres to skin on the breast (see FIG. 2B). The adhesive layer is cast with indentations to receive supplement reservoirs, controllable valves, tubing and microcircuitry including a battery. A second layer, or housing, of polymer, e.g., polyurethane, is cast in a rectangular shape to overlay the adhesive first layer with corresponding aligned indentations to hold the supplement reservoirs and other components in place. (See e.g., U.S. Patent Application No. 2003/0152612 by Pugliese et al. published on Aug. 14, 2003 which is incorporated herein by reference.) The polyurethane housing can be removed for replacement of the supplement reservoirs or for repair/replacement of other components, e.g., the battery.

Disposable rectangular polyurethane supplement reservoirs, approximately 0.5 cm in width, 2.5 cm in length and 0.5 cm in depth are cast with a port at one end which accepts an electronic valve. Each disposable supplement reservoir docks in the adhesive first layer with its port connected to an electronic valve which connects to an intake manifold and lastly a micropump. Each supplement reservoir is equipped with a conductivity meter to monitor the level of supplement in the reservoir. A thin film conductivity sensor approximately 1.5 cm in length is available from Innovative Sensor Technology USA, Las Vegas, Nev. (see the Info Sheet: Conductivity Sensor LFS155).

A solenoid operated pinch valve is connected in line with each supplement reservoir to control the flow of supplements and/or flavorings from the supplement reservoirs. Compact pinch valves which employ approximately ⅛ inch inside diameter tubing are available from ASCO, Florham, N.J. (see e.g., Compact 2-Way Pinch Valve Info Sheet from ASCO which is incorporated herein by reference). A micropump is connected to the intake manifold and a delivery tube extends from the micropump to the nipple region. For example an electromagnetic micropump with a maximum flow rate of 70 µL/min is described (see e.g., Nisar et al., *Sensors and Actuators B* 130: 917-942, 2008 which is incorporated herein by reference). A lithium battery, incorporated in the patch provides power to drive the solenoid actuated pinch valves and the electromagnetic micropump.

Disposable supplement reservoirs are preloaded with flavorings to condition the breast feeding infant's taste preferences and ultimately the child's diet and nutrition. Flavors experienced during infancy influence taste preferences later in life (see e.g., Beauchamp and Mennella, *Digestion* 83 (suppl. 1): 1-6, 2011 and Ventura and Worobey, *Current Biology* 23: R401-R408, 2013 which are incorporated herein by reference). For example, the supplement reservoirs may be preloaded with flavorings from vegetables such as dark leafy greens (e.g., broccoli, spinach, and kale), carrots, peas, squash, cauliflower and peppers.

The supplement reservoirs may also contain nutrients and vitamins to supplement breast milk; for example, vitamin A, iron, vitamin C, folate, zinc, calcium, and vitamin D may be present alone or in combination in the supplement reservoirs. Recommended daily intake for nutrients and vitamins in infants are known (see e.g., USDA website, "Interactive DRI for Healthcare Professionals" online at http://fnic.nal.usda.gov/fnic/interactiveDRI/dri_results.php which is incorporated herein by reference). For example, a 3 month old infant weighing approximately 9 pounds has daily recommended intake (DRI) values: Vitamin A=400 mcg; Vitamin C=40 mg; iron=270 mcg; folate=65 mcg; zinc=2 mg; calcium=200 mg; Vitamin D=10 mcg. Dosing of nutrients and vitamins may be adjusted (i.e. decreased) to account for breast milk nutrients consumed by the infant.

The breast patch has a control unit with a data storage component to retain and execute a preset breast milk supplement regimen of flavorings, nutrients and vitamins to condition and supplement the infant's tastes and diet respectively. Microcircuitry, microprocessors and data storage components control the pinch valves and the pump to deliver selected flavorings and nutrients to the nipple when the child is breast feeding. The breast patch has a RFID transceiver that communicates with a remote computer or mobile device to receive data, e.g., a nutrient regimen, and report data, e.g., nutrient delivery, reservoir depletion, etc. Also a user interface is incorporated in the polyurethane housing to allow data input and control of the device. A projected capacitive touch controller is inserted in the surface of the polyurethane housing of the breast patch to allow gesture and tap control of device function. A projected capacitive touch controller is available from Microchip Technology, Inc., Chandler, Ariz. (see e.g., User Interface-Touchscreen Datasheet which is incorporated herein by reference). The delivery regimen, i.e., dose and schedule, may be adjusted by the control unit in response to analyte sensors on the device.

Analyte sensors are attached to the breast patch on an extension of the polyurethane substrate near to the nipple to sample infant saliva, and breast milk during infant feeding. For example, aptamer-based field effect transistor sensors capable of detecting small molecules, proteins and virus are sensitive and specific. Sensors with single walled carbon nanotubes (SWNT) with selected aptamers coupled to their surface to recognize and detect nutrients (e.g., folate, vitamin D) and biologicals (e.g., IgA antibodies) are attached to the breast patch and connected to the control unit. Methods and materials to select aptamers and construct SWNT sensors are described (see e.g., U.S. Pat. No. 5,475,096 issued to Gold et al. on Dec. 12, 1995 and Lee et al., *Analytical Bioanalytical Chemistry* 390: 1023-1032, 2008 which are incorporated herein by reference). Signals from the analyte sensors on nutrient levels or biologicals are processed by the control unit and the schedule and dose of nutrient delivery may be adjusted, continued as preset, or stopped. Signals (i.e., data) on analyte levels, delivery regimens and reservoir nutrient levels may also be transmitted to a remote computer or mobile device via a RFID transceiver on the breast patch device.

The breast patch incorporates an RFID transmission unit as described in Prophetic Example 1. The RFID transmission unit includes antennas and circuitry to receive and transmit radio frequency signals to communicate with external computers and or mobile devices.

Prophetic Example 3: Pacifier with Controlled Delivery of Breast Milk Supplements An embodiment of a breast milk supplement delivery device is described. In this non-limiting example, the breast milk supplement delivery device takes the form a pacifier constructed to deliver breast milk supplements in a controlled fashion to an infant. The pacifier contains supplement reservoirs which release breast milk supplements under the direction of a control unit which includes microcircuitry, microprocessors, and memory. The control unit also contains wireless communication elements to receive breast milk supplement regimen information and to report on nutrient and flavoring delivery and consumption. Analyte sensors on the pacifier may detect nutrient supplements, flavorings, biologicals and metabolites in infant saliva. Signaling from analyte sensors is processed by the control unit which may respond by adjusting the breast milk supplement regimen. Nutrient delivery from the supplement reservoirs is controlled by electronic valves which are actuated by the control unit. A tube connects each supplement reservoir port with the nipple opening and sucking by the infant draws nutrient supplements through the pacifier nipple.

Figure 41:
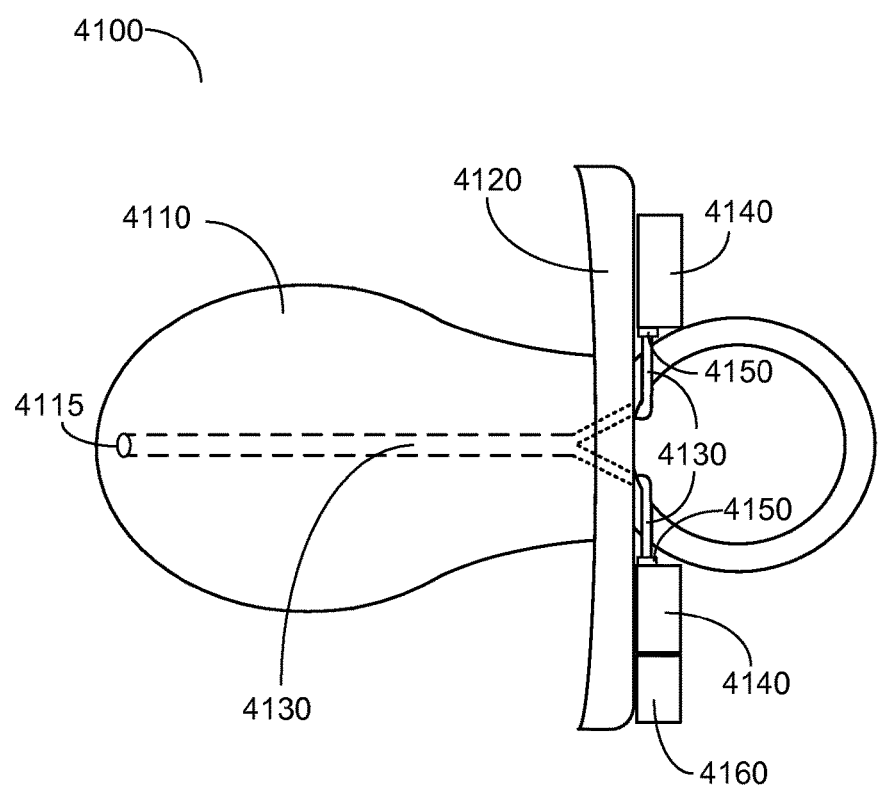
FIG. 41 illustrates an embodiment of a breast milk supplement delivery device.

FIG. 41 illustrates non-limiting aspects of a pacifier adapted to deliver one or more breast milk supplements. Pacifier 4100 includes nipple component 4110 including an aperture 4115, a guard component 4120, a flow conduit 4130 at least partially disposed within nipple component 4110 and guard component 4120, disposable supplement reservoirs 4140, a controllable valve 4150, and a control unit 4160. The disposable supplement reservoirs 4140 are in fluid communication with the flow conduit 4130 through the controllable valve 4150. In this non-limiting example, components of the disposable supplement reservoirs 4140 are attached to guard component 4120, with flow conduit 4130 passing through the guard component 4120 and connecting the disposable supplement reservoirs 4140 with aperture 4115 of the nipple component 4110.

Silicon rubber is cast in a mold to create a nipple component with an aperture (e.g., an opening), a flow conduit (e.g., a tube) connecting the nipple component to the guard component, and docking sites for the disposable supplement reservoirs, the controllable valves, and the control unit. Methods and materials to construct a device with a nipple and conduits are described (see e.g., U.S. Patent Appl. No. 2008/0167579 by Ezra et al. published on Jul. 10, 2008 which is incorporated herein by reference). Disposable supplement reservoirs may be molded from polyurethane with a complementary docking site and a port that accepts an electronic valve. For example, custom-molded polyurethane elastomer devices are available from Precision Engineering Products, East Providence, R.I. (see e.g., info sheet: PEP microPEP Drug Delivery Device Solutions available online at: http://www.pepmicropep.com/markets/medical-surgical/drug-delivery-device-solutions which is incorporated herein by reference). Disposable supplement reservoirs containing approximately 0.50 mL of a breast milk supplement are connected to electronic valves via their delivery ports and the combination, disposable supplement reservoir plus controllable valve, is attached to the pacifier at the reservoir docking site with the exit port of the valve connected to flow conduit near the guard component. Miniature electronic valves to control the flow of supplements from the disposable supplement reservoirs are available, for example, an 8 mm diaphragm isolation valve is available from ASCO, Florham, N.J. (See e.g., ASCO info sheet: 8 mm Diaphragm Isolation which is incorporated herein by reference.) Supplement delivery is initiated by opening an electronic valve at a reservoir port thus allowing an infant to suck the supplement through the valve and delivery tube which opens into the nipple opening and finally the infant's mouth. The reservoir also has an internal conductivity sensor to monitor the level of nutrient or flavoring remaining in the reservoir. Each reservoir is equipped with a conductivity sensor to monitor the level of supplement in the reservoir. A thin film conductivity sensor approximately 1.5 cm in length is available from Innovative Sensor Technology USA, Las Vegas, Nev. (see the Info Sheet: Conductivity Sensor LFS155). Supplement levels are reported to the control unit on the pacifier and they may be relayed to a remote computer or mobile device. For example, if a supplement reservoir is nearly empty, as reflected in its conductivity readings, then a parent or caregiver may be alerted to provide a new supplement reservoir filled with one or more breast milk supplements, or alternatively, a duplicate supplement reservoir on the pacifier may be activated automatically.

The pacifier is constructed with a control unit including microcircuitry, microprocessors, data storage component, and RFID transceivers that control the delivery of breast milk supplements to the infant and report delivery events to remote computers and mobile devices. A data storage component retains protocols for supplement delivery, i.e., one or more breast milk supplement regimens that include dose and schedule for specific nutrients. For example, a regimen for Vitamin D3 is executed by actuation circuitry that actuates (opens) the controllable valve for a vitamin D3 reservoir. Infant sucking on the pacifier results in vitamin D3 consumption and conductivity readings from the reservoir will reflect the amount remaining. The consumption of vitamin D3 is processed by the control unit to inform actuation of the controllable valve until a regimen is completed, e.g., 400 IU/day, for 5 days. Also the control unit reports on vitamin D3 consumption and reservoir depletion to remote computers and mobile devices.

The pacifier incorporates sensors to provide feedback control of supplement delivery. An infant presence detector, e.g., a pressure transducer, is located in the flow conduit of the pacifier that detects negative pressure when the infant is sucking on the pacifier. For example, a pressure sensor that detects and quantifies negative pressure from infant sucking is described (see e.g., Prieto et al., *J. Reproduction and Fertility* 108, 69-74, 1996 which is incorporated herein by reference). When sucking is detected, the control unit initiates supplement delivery by actuating the controllable valves as required. Analyte sensors located on the nipple component of the pacifier detect nutrients, metabolites, biologicals and flavorings in the infant's saliva, and analyte data is processed by the control unit to adjust the breast milk supplement regimen. For example, aptamer-based field effect transistor sensors capable of detecting small molecules, proteins and virus are sensitive and specific. Sensors with single walled carbon nanotubes (SWNT) with selected aptamers coupled to their surface to recognize and detect nutrients (e.g., folate, vitamin D) and biologicals (e.g., IgA antibodies) are attached to the nipple component and connected to the control unit. Methods and materials to select aptamers and construct SWNT sensors are described (see e.g., U.S. Pat. No. 5,475,096 issued to Gold et al. on Dec. 12, 1995 and Lee et al., Analytical Bioanalytical Chemistry 390: 1023-1032, 2008 which are incorporated herein by reference).

RFID transceivers on the pacifier receive data on supplement regimens and transmit data on supplement delivery and reservoir status. A RFID transceiver that includes antennas and circuitry to receive and transmit radio frequency signals communicates with external computers and or mobile devices as described in Prophetic Example 1.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors. A data processing system can be implemented utilizing suitable commercially available components, such as those typically found in data computing/communication and/or network computing/communication systems.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A breast milk supplement delivery device comprising:
 a nipple component sized for placement in an infant's mouth, the nipple component having a first end and a second end, the first end of the nipple component including an aperture;
 a guard component attached to the second end of the nipple component and including one or more ventilation apertures defined by the guard component;
 at least one exhaled breath analyte sensor associated with the one or more ventilation apertures defined by the guard component, the at least one exhaled breath analyte sensor positioned to sense at least one analyte in exhaled breath of the infant;
 a supplement reservoir disposed within the nipple component and including a port with a controllable valve, the supplement reservoir adapted to contain one or more breast milk supplements;

a flow conduit having a first end in fluid communication with the aperture on the first end of the nipple component and a second end in fluid communication with the port of the supplement reservoir disposed within the nipple component;

a breast milk supplement regimen stored in a data storage component the breast milk supplement regimen personalized based on a nutritional need of the infant and including dosage, timing, and composition of the one or more breast milk supplements; and a control unit including a microprocessor and circuitry, the control unit associated with at least one of the nipple component and the guard component and operably coupled to the controllable valve of the supplement reservoir, the at least one exhaled breath analyte sensor, and the data storage component, the circuitry including circuitry configured to receive the breast milk supplement regimen from the data storage component; actuation circuitry configured to actuate the controllable valve to modulate release of the one or more breast milk supplements from the supplement reservoir based on the breast milk supplement regimen; circuitry configured to receive information from the at least one exhaled breath analyte sensor regarding the sensed at least one analyte in the exhaled breath of the infant; and circuitry configured to modify at least one of the dosage, timing, and composition of the breast milk supplement regimen if the received information from the at least one exhaled breath analyte sensor is indicative of a change in the nutritional need of the infant.

2. The device of claim 1, wherein at least one of the one or more breast milk supplements comprises a lipid, a protein, an oligosaccharide, a fatty acid, a carbohydrate, a nutrient, a micronutrient, a vitamin, an amino acid, a mineral a therapeutic agent, an antimicrobial agent, a prebiotic, a probiotic, or a nucleotide.

3. The device of claim 1, wherein at least one of the one or more breast milk supplements comprises an appetite stimulator or an appetite suppressant.

4. The device of claim 1, wherein at least one of the one or more breast milk supplements comprises a flavoring associated with a specific food type, the flavoring intended to acclimate the infant to the specific food type.

5. The device of claim 1, wherein the controllable valve includes an actuator, the actuator operably coupled to the actuation circuitry.

6. The device of claim 1, wherein the actuation circuitry includes circuitry configured to at least one of open the controllable valve, close the controllable valve, change a pressure threshold of the controllable valve, increase an opening size of the controllable valve, decrease an opening size of the controllable valve, or alter a permeability or porosity of the controllable valve.

7. The device of claim 1, wherein the breast milk supplement regimen is personalized for the nutritional need of the infant and at least one of age, weight, genome, gender, ethnicity, and medical condition of the infant.

8. The device of claim 1, wherein the breast milk supplement regimen is personalized for the nutritional need of the infant and a quality of breast milk of a lactating female.

9. The device of claim 1, further comprising:

at least one delivery event sensor configured to sense a delivery event, wherein the delivery event includes controlled release of the one or more breast milk supplements from the supplement reservoir and to the infant; and wherein the control unit includes delivery event circuitry configured to receive information associated with the sensed delivery event from the at least one delivery event sensor, the received information including at least one of a breast milk supplement type, a dosage, an infant identifier, a time, and a date; and reporting circuitry configured to report the delivery event.

10. The device of claim 9, wherein the at least one delivery event sensor includes at least one of a flow sensor, a pressure sensor, a strain sensor, a conductivity sensor, an acoustic sensor, an optical transmission sensor, a clock, or a weight sensor.

11. The device of claim 9, wherein the reporting circuitry includes circuitry configured to report the delivery event including the at least one of the breast milk supplement type, the dosage, the infant identifier, the time, and the date to a mobile communication device.

12. The device of claim 1, further comprising:

a transmission unit including circuitry and at least one antenna, wherein the transmission unit is operably coupled to the control unit and configured to transmit information associated with a delivery event to a mobile communication device, the information associated with the delivery event including at least one of a breast milk supplement type, a dosage, an infant identifier, a time and a date.

13. The device of claim 1, further comprising:

a pressure transducer positioned in the flow conduit of the nipple component;

wherein the pressure transducer is configured to detect negative pressure associated with the infant sucking on the nipple component, and to provide an infant presence signal to the control unit; and wherein the actuation circuitry includes circuitry configured to actuate the controllable valve of the supplement reservoir based on the infant presence signal and the breast milk supplement regimen.

14. The device of claim 1, further comprising:

a temperature control component configured to control a temperature of at least one of a portion of the nipple component and the supplement reservoir.

15. The device of claim 1, wherein the at least one exhaled breath analyte sensor is incorporated into a meshwork spanning the one or more ventilation apertures defined by the guard component.

16. A pacifier device for controlled delivery of breast milk supplements comprising:

a nipple component sized for placement in an infant's mouth, the nipple component having a first end and a second end, the first end of the nipple component including an aperture;

a guard component attached to the second end of the nipple component and including one or more ventilation apertures defined by the guard component;

two or more disposable supplement reservoirs reversibly attachable to the guard component, each of the two or more disposable supplement reservoirs including a port with a controllable valve, each of the two or more disposable supplement reservoirs adapted to contain one or more breast milk supplements;

a flow conduit disposed within at least a portion of the nipple component, a first end of the flow conduit in fluid communication with the aperture on the first end of the nipple component and a second end of the flow conduit in fluid communication with the port of each of the two or more disposable supplement reservoirs;

one or more exhaled breath analyte sensors associated with the one or more ventilation apertures defined by the guard component, the one or more exhaled breath analyte sensors positioned to sense at least one analyte in exhaled breath of the infant; and a control unit including a microprocessor and circuitry, the control unit operably coupled to the controllable valve of each of the two or more disposable supplement reservoirs and to the one or more exhaled breath analyte sensors, the circuitry including actuation circuitry configured to actuate the controllable valve of each of the two or more disposable supplement reservoirs;

wherein the control unit includes circuitry configured to receive information associated with at least one analyte in the exhaled breath of the infant from at least one of the one or more exhaled breath analyte sensors and to actuate the controllable valve of at least one of the two or more disposable supplement reservoirs to modulate release of the one or more breast milk supplements from the at least one of the two or more disposable supplement reservoirs in response to the received information associated with the at least one analyte in the exhaled breath of the infant.

17. The device of claim 16, wherein the controllable valve includes an actuator, the actuator operably coupled to the actuation circuitry.

18. The device of claim 17, wherein the actuator includes at least one of a pneumatic actuator, a hydraulic actuator, a magnetic actuator, or an electric actuator.

19. The device of claim 16, wherein at least one of the one or more exhaled breath analyte sensors is configured to sense at least one of a lipid, a protein, an oligosaccharide, a fatty acid, a carbohydrate, a nutrient, a micronutrient, a vitamin, an amino acid, a mineral, or a nucleotide in the exhaled breath of the infant.

20. The device of claim 16, wherein at least one of the one or more exhaled breath analyte sensors is configured to sense a microorganism in the exhaled breath of the infant.

21. The device of claim 16, further comprising:
at least one delivery event sensor configured to sense a delivery event, wherein the delivery event includes controlled release of the one or more breast milk supplements from at least one of the one or more disposable supplement reservoirs to the infant; and
wherein the control unit includes delivery event circuitry configured to receive information associated with the sensed delivery event from the at least one delivery event sensor, the received information including at least one of a breast milk supplement type, a dosage, an infant identifier, a time, and a date; and reporting circuitry configured to report the delivery event including the at least one of the breast milk supplement type, the dosage, the infant identifier, the time, and the date to a mobile device.

22. The device of claim 21, wherein the reporting circuitry includes circuitry configured to report the delivery event through at least one of a radiofrequency transmission, a radiofrequency identification (RFID) transmission, an optical transmission, or an audio transmission.

23. The device of claim 16, further comprising:
a transmission unit including circuitry and at least one antenna, wherein the transmission unit is operably coupled to the control unit and configured to transmit one or more signals having information associated with a delivery event to a mobile device, the information associated with the delivery event including at least one of a breast milk supplement type, a dosage, an infant identifier, a time and a date.

24. The device of claim 16, further comprising:
a breast milk supplement regimen personalized based on a nutritional need of the infant and including dosage, timing and composition of the one or more breast milk supplements, wherein the breast milk supplement regimen is stored on a data storage component operably coupled to the control unit, wherein the control unit includes circuitry configured to update the personalized breast milk supplement regimen in response to the received information associated with the at least one exhaled breath analyte.

25. The device of claim 16, further comprising:
a temperature sensor associated with the nipple component;
wherein the temperature sensor is positioned to sense a change in temperature when the nipple component comes in contact with the infant's mouth, and configured to provide an infant presence signal to the control unit;
wherein the actuation circuitry includes circuitry configured to actuate the controllable valve of at least one of the two or more disposable supplement reservoirs based on the infant presence signal.

26. The device of claim 16, wherein the one or more exhaled breath analyte sensors are incorporated into a meshwork spanning the one or more ventilation apertures defined by the guard component.

27. A breast milk supplement delivery system comprising:
a delivery unit including
a nipple component sized for placement in an infant's mouth, the nipple component having a first end and a second end, the first end of the nipple component including an aperture;
a guard component attached to the second end of the nipple component and including one or more ventilation apertures defined by the guard component;
at least one exhaled breath analyte sensor associated with the one or more ventilation apertures defined by the guard component, the at least one exhaled breath analyte sensor positioned to sense at least one analyte in exhaled breath of the infant;
a supplement reservoir disposed within the nipple component and including a port with a controllable valve, the supplement reservoir adapted to contain one or more breast milk supplements;
a flow conduit having a first end in fluid communication with the aperture on the first end of the nipple component and a second end in fluid communication with the port of the supplement reservoir disposed within the nipple component; and
a transmission unit including an antenna;
a breast milk supplement regimen stored on a data storage component, wherein the breast milk supplement regimen is personalized based on a nutritional need of the infant and includes dosage, timing, and composition of the one or more breast milk supplements; and
a mobile device including
a second transmission unit including a second antenna, the second transmission unit configured to communicate with the transmission unit of the delivery unit;
a user interface including a display; and
a control unit including a microprocessor and circuitry, the control unit including circuitry configured to access the breast milk supplement regimen from the data storage component; actuation circuitry configured to wirelessly actuate the controllable valve of the supplement reservoir to modulate release of the one or more breast milk supplements based on the breast milk supplement regimen; circuitry configured to wirelessly receive information associated with the sensed at least one analyte in the exhaled breath of the infant from the at least one exhaled breath analyte sensor associated with the delivery unit; and circuitry configured to modify at least one of the dosage, timing, and composition of the breast milk supplement regimen if the received information associated with the sensed at least one analyte in the exhaled breast of the infant is indicative of a change in the nutritional need of the infant.

28. The delivery system of claim 27, wherein the data storage component including the breast milk supplement regimen is incorporated into the control unit of the mobile device.

29. The delivery system of claim 27, wherein the data storage component including the breast milk supplement regimen is on a remote computing device and accessible to the control unit of the mobile device.

30. The delivery system of claim 27, wherein the control unit of the mobile device includes
delivery event circuitry configured to wirelessly receive information associated with a delivery event from the delivery unit, wherein the received information associated with the delivery event includes at least one of a breast milk supplement type, a dosage, an infant identifier, a time, and a date; and
reporting circuitry configured to report the received information associated with the delivery event including the at least one of the breast milk supplement type, the dosage, the infant identifier, the time, and the date to the display of the mobile device.

31. The delivery system of claim 27, further comprising:
at least one pressure sensor positioned in proximity to the nipple component of the delivery unit to detect pressure on the nipple component of the delivery unit;
wherein the at least one pressure transducer is configured to provide an infant presence signal to the control unit of the mobile device in response to detected pressure on the nipple component of the delivery unit; and
wherein the actuation circuitry includes circuitry configured to wirelessly actuate the controllable valve of the supplement reservoir of the delivery unit based on the infant presence signal.

32. The delivery system of claim 27, further comprising:
at least one delivery event sensor configured to sense a delivery event, wherein the delivery event includes controlled release of the one or more breast milk supplements from the supplement reservoir and to the infant; and wherein the control unit includes delivery event circuitry configured to wirelessly receive information associated with sensed delivery event from the at least one delivery event sensor, the received information associated with the sensed delivery event including at least one of a breast milk supplement type, a dosage, an infant identifier, a time, and a date; and reporting circuitry configured to report the delivery event on the display of the mobile device.

33. The delivery system of claim 27, wherein at least one of the one or more exhaled breath analyte sensors is configured to sense at least one of a lipid, a protein, an oligosaccharide, a fatty acid, a carbohydrate, a nutrient, a micronutrient, a vitamin, an amino acid, a mineral, or a nucleotide in the exhaled breath of the infant.

34. The delivery system of claim 27, wherein at least one of the one or more exhaled breath analyte sensors is configured to sense at least one microorganism in the exhaled breath of the infant.

35. The delivery system of claim 27, wherein the at least one exhaled breath analyte sensor is incorporated into a meshwork spanning the one or more ventilation apertures defined by the guard component.

* * * * *